(12) United States Patent
Sigalov

(10) Patent No.: US 8,278,271 B2
(45) Date of Patent: Oct. 2, 2012

(54) INHIBITING COLLAGEN-INDUCED PLATELET AGGREGATION AND ACTIVATION WITH PEPTIDE VARIANTS

(75) Inventor: Alexander B. Sigalov, Worcester, MA (US)

(73) Assignee: University of Massachusetts, Boston, MA (US)

( * ) Notice: Subject to any disclaimer, the term of this patent is extended or adjusted under 35 U.S.C. 154(b) by 1166 days.

(21) Appl. No.: 12/001,258

(22) Filed: Dec. 11, 2007

(65) Prior Publication Data

US 2009/0075899 A1  Mar. 19, 2009

Related U.S. Application Data

(60) Provisional application No. 60/874,694, filed on Dec. 13, 2006.

(51) Int. Cl.
*A61K 38/10* (2006.01)
(52) U.S. Cl. .......................................... 514/9.7; 530/326
(58) Field of Classification Search ........................ None
See application file for complete search history.

(56) References Cited

U.S. PATENT DOCUMENTS

| | | | | |
|---|---|---|---|---|
| 6,589,992 | B2 | 7/2003 | Uckun | 514/626 |
| 6,989,144 | B1 | 1/2006 | Busfield et al. | 424/130.1 |
| 6,998,469 | B2 * | 2/2006 | Tandon et al. | 530/388.25 |
| 7,096,554 | B2 | 8/2006 | Austin et al. | 29/282 |
| 2004/0157300 | A1 | 8/2004 | Burger et al. | 435/69.7 |
| 2005/0142140 | A1 | 6/2005 | Massberg et al. | 424/178.1 |

OTHER PUBLICATIONS

Rudinger, Peptide Hormones, JA Parsons, Ed., 1976, pp. 1-7.*
Sigma. Designing custom peptides. hhtp://www.sigmaaldrich.com.*
Berendsen a glimpse of the Holy Grail? Science, 1998, vol. 282, pp. 642-643.*
Ali, M. et al., "Hydrophobic transmembrane-peptide lipid conjugations enhance membrane binding and functional activity in T-cells," *Bioconjug. Chem.* 16:1556-1563 (2005).
Amon, M.A. et al., "Lipidation and glycosylation of a T cell antigen receptor (TCR) transmembrane hydrophobic peptide dramatically enhances in vitro and in vivo function," *Biochim. Biophys. Acta.* 1763:879-888 (2006).
Arkin, M., "Protein-protein interactions and cancer: small molecules going in for the kill," *Curr. Opin. Chem. Biol.* 9:317-324 (2005).
Asai, K. et al., "Distinct aggregation of b- and g-chains of the high affinity IgE receptor on cross-linking," *J. Histochem. Cytochem.* 48:1705-1716 (2000).
Barnard et al., "Effects of platelet binding on whole blood flow cytometry assays of monocyte and neutrophil procoagulant activity," *J. Thromb. Haemost.* 3:2563-2570 (2005).
Bennasroune, A. et al., "Transmembrane peptides as inhibitors of ErbB receptor signaling," *Mol. Biol. Cell* 15:3464-3474 (2004).
Berg, T., "Modulation of protein-protein interactions with small organic molecules," *Angew. Chem. Int. Ed. Engl.* 42:2462-2481 (2003).
Berlanga et al., "The Fc Receptor g-Chain is Necessary and Sufficient to Initiate Signaling Through Glycoprotein VI in Transfected Cells by the Snake C-Type Lectin, Convulxin," *Eur J Biochem* 269:2951-2960 (2002).
Biassoni, R. et al., "Human natural killer cell activating receptors," *Mol. Immunol.* 37:1015-1024 (2000).
Borrego, F. et al., "Structure and function of major histocompatibility complex (MHC) class I specific receptors expressed on human natural killer (NK) cells," *Mol. Immunol.* 38:637-660 (2002).
Call, M.E. et al., "The organizing principle in the formation of the T cell receptor—CD3 complex," *Cell* 111:967-979 (2002).
Daeron, M., "Fc receptor biology," *Annu. Rev. Immunol.* 15:203-234 (1997).
Draberova, L. et al., "Signaling assemblies formed in mast cells activated via Fce receptor I dimers," *Eur. J. Immunol.* 34:2209-2219 (2004).
Dustin, M.L., "A dynamic view of the immunological synapse," *Semin. Immunol.* 17:400-410 (2005).
Enk, A.H. and Knop, J., "T cell receptor mimic peptides and their potential application in T-cell-mediated disease," *Int. Arch. Allergy Immunol.* 123, 275-281 (2000).
Farndale, P.W., "Collagen-induced platelet activation" *Blood Cells, Molecules, and Diseases* 36:162-165 (2006).
Garnier et al., "GOR method for predicting protein secondary structure from amino acid sequence," *Methods Enzymol.* 266:540-553 (1996).
Gawaz, M., "Role of platelets in coronary thrombosis and reperfusion of ischemic myocardium," *Cardiovascular Research* 61:498-511 (2004).
Geourjon and Deléage, "SOPMA: significant improvements in protein secondary structure prediction by consensus prediction from multiple alignments," *Comput. Appl. Biosci.* 11(6):681-4 (1995).
Gerber et al., "D-enantiomer peptide of the TCR-alpha transmembrane domain inhibits T-cell activation in vitro and in vivo," *FASEB Journal (FJ Express)* 19:1190-1192 (2005).
Harbury et al., "High-resolution protein design with backbone freedom," *Science* 282:1462-1467 (1998).
Jung et al., "Surface plasmon resonance imaging-based protein arrays for high-throughput screening of protein-protein interaction inhibitors," *Proteomics* 5:4427-4431 (2005).

(Continued)

Primary Examiner — Christopher R. Tate
Assistant Examiner — Roy Teller
(74) Attorney, Agent, or Firm — Medlen & Carroll, LLP

(57) ABSTRACT

The present invention provides peptides consisting of L- and/or D-amino acids and combinations thereof, which affect platelets by action on the collagen receptor, glycoprotein VI (GPVI). More specifically, however, the peptides act on the GPVI-FcRγ signaling complex. The invention also provides lipid and sugar conjugated peptides comprising L- or D-amino acids. The invention still further provides a method of designing of the peptides and lipid- and/or sugar-conjugated peptides comprising L- or D-amino acids. The present invention further relates to the therapy of various disease states involving the use of these peptides and compounds. Specifically, the peptides and compounds are useful in the treatment and/or prevention of a disease or condition involving platelet activation and aggregation, and more particularly, collagen-induced platelet activation and aggregation. They also are useful in the production of medical devices comprising peptide matrices (i.e., for example, cardiovascular stents).

2 Claims, 26 Drawing Sheets
(8 of 26 Drawing Sheet(s) Filed in Color)

OTHER PUBLICATIONS

Kay et al., "High-throughput screening strategies to identify inhibitors of protein-protein interactions," *Mol. Diversity* 1:139-140 (1996).

Keppler, O.T. et al., "Modulation of specific surface receptors and activation sensitization in primary resting CD4+ T lymphocytes by the Nef protein of HIV-1," *J. Leukoc. Biol.* 79:616-627 (2006).

Kim, J.H. et al., "Independent trafficking of Ig-a/Ig-b and m-heavy chain is facilitated by dissociation of the B cell antigen receptor complex," *J. Immunol.* 175:147-154 (2005).

Kliger et al., "Fusion peptides derived from the HIV type 1 glycoprotein 41 associate with Mn phospholipid membranes and inhibit cell-cell fusion. Structure-function study," *J. Biol. Chem.* 272:13496-13505 (1997).

Krummel, M.F. et al., "Differential clustering of CD4 and CD3z during T cell recognition," *Science* 289:1349-1352 (2000).

La Gruta, N.L. et al., "Architectural changes in the TCR:CD3 complex induced by MHC:peptide ligation," *J. Immunol.* 172:3662-3669 (2004).

Loregian, A. and Palu, G., "Disruption of protein-protein interactions: towards new targets for chemotherapy," *J. Cell. Physiol.* 204:750-762 (2005).

Manolios, N. et al., "Transmembrane helical interactions and the assembly of the T cell receptor complex," *Science* 249:274-277 (1990).

Matsumoto el al., "Highly potent anti-human GPVI monoclonal antibodies derived from GPVI knockout mouse immunization" *Thromb. Res.* 119:319-329 (2007).

Merrifield et al., "Synthesis of the antibacterial peptide cecropin A (1-33)," *Biochemistry* 21:5020-5031 (1982).

Michelson, Alan D. (ed.) Platelets. Academic Press (2002).

Michelson, A. D., "Evaluation of platelet function by flow cytometry," *Pathophysiol. Haemost. Thromb.* 35:67-82 (2006).

Michnoff, C.H. et aL, "Mutations within the NH2-terminal transmembrane domain of membrane immunoglobulin (Ig) M alters Iga and Igb association and signal transduction," *J. Biol. Chem.* 269:24237-24244 (1994).

Moroi et al., "Platelet glycoprotein VI: its structure and function," *Thromb. Res.* 114:221-233 (2004).

Nieswandt et al., "Glycoprotein VI but not alpha$_2$beta$_1$ integrin is essential for platelet interaction with collagen," *EMBO J.* 20:2120-2130 (2001).

Nieuwenhuijsen et al., "A dual luciferase multiplexed high-throughput screening platform for protein-protein interactions," *J. Biomol. Screen* 8:676-684 (2003).

Patrick, S.M. et al., "Dependence of T cell activation on area of contact and density of a ligand-coated surface," *J. Immunol. Methods* 241:97-108 (2000).

Pecht, I. et al., "Rotational dynamics of the Fce receptor on mast cells monitored by specific monoclonal antibodies and IgE," *Biochemistry* 30:3450-3458 (1991).

Pfleger et al., "Extended bioluminescence resonance energy transfer (eBRET) for monitoring prolonged protein-protein interactions in live cells," *Cell. Signaling* 18:1664-1670 (2006).

Pitcher, L.A. et al., "The CD3 ge/de signaling module provides normal T cell functions in the absence of the TCR z immunoreceptor tyrosine-based activation motifs," *Eur. J. Immunol.* 35:3643-3654 (2005).

Posner, R.G. et al., "Interaction of a monoclonal IgE-specific antibody with cell-surface IgE-FceR1: characterization of equilibrium binding and secretory response," *Biochemistry* 43:11352-11360 (2004).

Prunotto et al., "Stenting: biomaterials in mini-invasive cardiovascular applications," *Anal. Bioanal. Chem.* 381:531-533 (2005).

Quintana, F.J. et al., "HIV-1 fusion peptide targets the TCR and inhibits antigen-specific T cell activation," *J. Clin. Invest.* 115:2149-2158 (2005).

Risueno, R.M. et al., "Ligand-induced conformational change in the T-cell receptor associated with productive immune synapses," *Blood* 106:601-608 (2005).

Rudolph, M.G. and Wilson, I.A., "The specificity of TCR/pMHC interaction,". *Curr. Opin. Immunol.* 14:52-65 (2002).

Schamel, W.W. et al., "Coexistence of multivalent and monovalent TCRs explains high sensitivity and wide range of response," *J. Exp. Med.* 202:493-503 (2005).

Schrager, J.A. and Marsh, J.W. "HIV-1 Nef increases T cell activation in a stimulus-dependent manner," *Proc. Natl. Acad. Sci. U. S. A.* 96:8167-8172 (1999).

Shattil et al., "Changes in the platelet membrane glycoprotein IIb/IIIa complex during platelet activation," *J. Biol. Chem.* 260:11107-11114 (1985).

Siegel, R.M. et al., "SPOTS: signaling protein oligomeric transduction structures are early mediators of death receptor-induced apoptosis at the plasma membrane," *J. Cell Biol.* 167:735-744 (2004).

Sigalov, A.B., "Multichain immune recognition receptor signaling: different players, same game?" *Trends Immunol.* 25:583-589 (2004).

Sigalov, A.B. et al., "Homooligomerization of the cytoplasmic domain of the T cell receptor z chain and of other proteins containing the immunoreceptor tyrosine-based activation motif," *Biochemistry* 43:2049-2061 (2004).

Sigalov, A., "Multi-chain immune recognition receptors: spatial organization and signal transduction," *Semin. Immunol.* 17:51-64 (2005).

Simmons, A. et al., "Nef triggers a transcriptional program in T cells imitating single-signal T cell activation and inducing HIV virulence mediators," *Immunity* 14:763-777 (2001).

Stockwell, B. R., "Exploring biology with small organic molecules," *Nature* 432:846-854 (2004).

Suzuki et al., "Stent-based delivery of sirolimus reduces neointimal formation in a porcine coronary model," *Circulation* 104:1188-1193 (2001).

Swigut, T. et al., "Cooperative interactions of simian immunodeficiency virus Nef, AP-2, and CD3-z mediate the selective induction of T-cell receptor—CD3 endocytosis," *J. Virol.* 77:8116-8126 (2003).

Tsuji et al., "Biodegradable stents as a platform to drug loading," *Int. J. Cardiovasc. Intervent.* 5:13-16 (2003).

van Praag, R.M. et al., "OKT3 and IL-2 treatment for purging of the latent HIV-1 reservoir in vivo results in selective long-lasting CD4+ T cell depletion," *J. Clin. Immunol.* 21:218-226 (2001).

Wang, X.M. et al., "T-cell antigen receptor peptides inhibit signal transduction within the membrane bilayer," *Clin. Immunol.* 105:199-207 (2002).

Whelan et al., "Mechanisms of drug loading and release kinetics," *Semin. Interv. Cardiol.* 3:127-131 (1998).

Whittaker et al., "A gentle method for linking Tris to amino acids and peptides," *Peptide Research* 6:125-128 (1993).

Wilson, B.S. et al., "Distinct functions of the FceR1 g and b subunits in the control of FceR1-mediated tyrosine kinase activation and signaling responses in RBL-2H3 mast cells," *J. Biol. Chem.* 270:4013-4022 (1995).

Yamasaki, S. et al., "Mechanistic basis of pre-T cell receptormediated autonomous signaling critical for thymocyte development," *Nat. Immunol.* 7:67-75 (2006).

Zheng et al., "Expression of the Platelet Receptor GPVI Confers Signaling Via the Fc Receptor γ-Chain in Response to the Snake Venom Convulxin but not to Collagen," *J. Biol. Chem.* 276:12999-13006 (2001).

Zoldhelyi et al., "Inhibition of coronary thrombosis and local inflammation by a noncarbohydrate selectin inhibitor," *Am J Physiol Heart Circ Physiol* 279:H3065-H3075 (2000).

Bender, V. et al., "T Cell Antigen Reveptor Peptide-Lipid Membrane interactions Using Surface Plasmon Resonance," *J. Biol. Chem.* 279:54002-54007 (2004).

Buser, C.A. et al., "Membrane Binding of Myristylated Peptides Corresponding to the NH2 Terminus of Src," *Biochemistry* 33:13093-13101 (1994).

De Coupade, C. et al., "Novel Human-Derived Cell-Penetrating Peptides for Specific Subcellular Delivery of Therapeutic Biomolecules," *Biochem. J.* 390:407-418 (2005).

Drouillat, B. et al., "Novel Liposaccharide Conjugates for Drug and Peptide Delivery,"*J. Pharm. Sci.* 87:25-30 (1998).

Guermeur, Y. et al., "Improved Performance in Protein Secondary Structure Prediction by Inhomogeneous Score Combination," *Bioinformatics* 15:413-421 (1999).

Kyte, J. and Doolittle, R.F., "A Simple Method for Displaying the Hydropathic Character of a Protei," *J. Mol. Biol.* 157:105-32, 1982.

Laczko, I. et al., "Conformational Effect of Phosphorylation on T Cell Receptor/CD3 Zeta-Chain Sequences," *Biochem. Biophys. Res. Commun.* 242:474-479 (1998).

Langosch, D. et al., "Peptide Mimics of SNARE Transmembrane Segments Drive Membrane Fusion Depending on Their Conformational Plasticity," *J. Mol. Biol.* 311:709-721 (2001).

Peters, C. et al., "Bridging the Gap Between Cell Biology and Organic Chemistry: Chemical Synthesis and Biological Application of Lipidated Peptides and Proteins," *Naturwissenschaften* 89:381-390 (2002).

Sigalov, A.B., "Immune Cell Signaling: A Novel Mechanistic Model Reveals New Therapeutic Targets," *Trends Pharmacol. Sci.* 27:518-524 (2006).

Toth, I., "A Novel Chemical Approach to Drug Delivery: Lipid Amino Acid Conjugates," *J. Drug Target* 2:217-239 (1994).

Kato et al., *Effect of multimer size and a natural dimorphism on the binding of convulxin to platelet glycoprotein (GP)VI*, Journal of Thrombosis and Haemostasis, 4: 1107-1113, May 2006.

O'Connor et al., *Selective Blockade of Glycoprotein VI Clustering on Collagen Helices*, The Journal of Biological Chemistry, vol. 281, No. 44, pp. 33505-33510, Nov. 3, 2006.

European Search Report, Dated Apr. 26, 2011.

\* cited by examiner

INHIBITING COLLAGEN-INDUCED PLATELET AGGREGATION AND ACTIVATION WITH PEPTIDE VARIANTS

This application for patent under 35 U.S.C. §111(a) claims priority to Provisional Application(s) Ser. No. 60/874,694 filed on Dec. 13, 2006 under 35 U.S.C. §111(b).

This invention was made with government support under grant no. AI042845 awarded by the National Institutes Of Health. The government has certain rights in the invention.

FIELD OF THE INVENTION

The present invention relates to peptides and compounds which affect platelets by action on the collagen receptor, glycoprotein VI. The present invention further relates to the treatment or prevention of a disease or condition involving platelet activation and aggregation and, more particularly, collagen-induced platelet activation and aggregation. In one embodiment, GPVI-FcRγ signaling is inhibited by variant peptides binding to the transmembrane region of the FcRγ subunit.

BACKGROUND

Platelets are small, anucleated blood cells which have a seminal role in hemostasis and thrombosis. Cardiovascular disease, the major cause of death and morbidity in developed countries, is often a result of ischemic and/or thromboembolic events including chronic unstable angina transient ischemic attacks and strokes, myocardial infarction, chronic unstable angina, peripheral vascular disease, coronary thrombosis, restenosis and/or thrombosis following angioplasty and others. These events represent various stenotic and occlusive vascular disorders involving platelet aggregation on vessel walls or within the lumen. In: *Platelets*, Alan D. Michelson (ed.) Academic Press, (2002)(incorporated herein by reference).

Antibodies have been considered as clinically significant therapeutic agents for various platelet-mediated cardiovascular disorders. However, antibody therapy poses serious disadvantages. First, as antibodies are natural products they must be produced in cell lines or other live expression systems. This raises a that there could be contamination of antibody preparations by infectious agents such as prions or viruses. Although tight regulation and regulatory vigilance and surveillance can reduce this concern, the need for ongoing monitoring and testing for contamination contributes to the high cost of developing and administering antibody therapies. In addition, antibody-based therapies require considerable logistical support. As antibodies are proteins, they cannot be given orally, except for those used to treat certain types of mucosal infectious diseases, and therefore, systemic administration is required. Another serious disadvantage of antibody-based therapies is the high costs of production, storage, and administration. Moreover, long infusions (i.e., for example, an hour or longer) require a hospital environment and are often associated with mild to very severe side effects. For example, in one trial, in which four patients in the U.K. were given an anticancer antibody reactive against an important T-cell receptor (CD28) severe and life-threatening responses were observed; the cause is at present not understood. This makes large-scale clinical applications of a number of monoclonal antibodies with demonstrated therapeutic activity impossible or, at least, severely compromised. Fast degradation of the administered antibodies is another drawback of antibody-based therapy.

What is needed in the art is a broad-based therapy designed to disrupt protein-protein interactions that may be administered to treat various cardiovascular diseases having an underlying platelet etiology that is safe and effective.

SUMMARY

The present invention relates to peptides and compounds which affect platelets by action on the collagen receptor, glycoprotein VI. The present invention further relates to the treatment or prevention of a disease or condition involving platelet activation and aggregation and, more particularly, collagen-induced platelet activation and aggregation. In one embodiment, GPVI-FcRγ signaling is inhibited by variant peptides binding to the transmembrane region of the FcRγ subunit.

In one embodiment, the present invention contemplates a variant GPVI peptide inhibitor comprising at least one amino acid addition and/or substitution that optimizes binding to an FcRγ subunit relative to SEQ ID NO: 9. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate.

In one embodiment, the present invention contemplates a method comprising: a) providing; i) a patient having at least one symptom of a medical condition resulting from platelet activation; and ii) a variant GPVI peptide inhibitor comprising at least one amino acid addition and/or substitution that optimizes binding to an FcRγ subunit relative to SEQ ID NO: 9 capable of reducing said platelet activation; b) administering said inhibitor to said patient under conditions such that said at least one symptom is reduced. In one embodiment, the medical condition comprises a collagen-induced platelet disorder. In one embodiment, the platelet disorder is selected from the group consisting of atherosclerosis, coronary artery disease, ischemic cerebrovascular disease, peripheral vascular disease, diabetes mellitus, renal disease, inflammatory bowel disease, asthma, cystic fibrosis, rheumatoid arthritis, Kawasaki disease, tumor growth and metastasis, Alzheimer's disease, psychiatric disorders, thrombocytopenia, platelet function defects, von Willebrand disease, immune thrombocytopenia purpura, and inherited and acquired disorders of platelet function.

In one embodiment, the present invention contemplates a peptide inhibitor comprising an amino acid sequence consisting of G-N-L-V-R-I-$X_1$-$X_2$-$X_3$-A-$X_4$-$X_5$-$X_6$-$X_7$-I (SEQ ID NO:1), wherein $X_1$ is selected from the group consisting of consisting of C, L or G; $X_2$ is selected from the group consisting of L or A; $X_3$ is selected from the group consisting of G or R; $X_4$ is selected from the group consisting of V or I; $X_5$ is selected from the group consisting of I, L or R; $X_6$ is selected from the group consisting of I or L; and $X_7$ is selected from the group consisting of I or L. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide inhibitor includes amino acids selected from the group including, but not limited to, L-amino acids, or D-amino acids.

In one embodiment, the present invention contemplates a method comprising: a) providing; i) a patient having a medical condition resulting from platelet aggregation; and ii) a peptide inhibitor comprising an amino acid sequence consisting of G-N-L-V-R-I-$X_1$-$X_2$-$X_3$-A-$X_4$-$X_5$-$X_6$-$X_7$-I (SEQ ID NO:1), wherein $X_1$ is selected from the group consisting of consisting of C, L or G; $X_2$ is selected from the group consisting of L or A; $X_3$ is selected from the group consisting of G or R; $X_4$ is selected from the group consisting of V or I; $X_5$ is selected from the group consisting of I, L or R; $X_6$ is selected from the group consisting of I or L; and $X_7$ is selected from the group consisting of I or L capable of reducing said platelet aggregation; b) administering said inhibitor to said patient under conditions such that said aggregation is reduced. In one embodiment, the medical condition comprises a collagen-induced platelet disorder. In one embodiment, the platelet disorder is selected from the group consisting of atherosclerosis, coronary artery disease, ischemic cerebrovascular disease, peripheral vascular disease, diabetes mellitus, renal disease, inflammatory bowel disease, asthma, cystic fibrosis, rheumatoid arthritis, Kawasaki disease, tumor growth and metastasis, Alzheimer's disease, psychiatric disorders, thrombocytopenia, platelet function defects, von Willebrand disease, immune thrombocytopenia purpura, and inherited and acquired disorders of platelet function.

In one embodiment, the present invention contemplates a peptide inhibitor comprising an amino acid sequence consisting of X-$X_2$-$X_3$-$X_4$-$X_5$-Y-A-R-A-L-L-Y-G-L-R-A-V-G-Y-$X_6$-$X_7$-$X_8$ (SEQ ID NO:2), wherein $X_1$ consists of G or nothing; and $X_2$, $X_3$, $X_4$, $X_5$, $X_6$, $X_7$, and $X_8$ consist of K, R, or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide inhibitor includes amino acids selected from the group including, but not limited to, L-amino acids, or D-amino acids.

In one embodiment, the present invention contemplates a method comprising: a) providing; i) a patient having a medical condition resulting from platelet aggregation; and ii) a peptide inhibitor comprising an amino acid sequence consisting of $X_1$-$X_2$-$X_3$-$X_4$-$X_5$-Y-A-R-A-L-L-Y-G-L-R-A-V-G-Y-$X_6$-$X_7$-$X_8$ (SEQ ID NO: 2), wherein $X_1$ consists of G or nothing; and $X_2$, $X_3$, $X_4$, $X_5$, $X_6$, $X_7$, and $X_8$ consist of K, R, or nothing capable of reducing said platelet aggregation; b) administering said inhibitor to said patient under conditions such that said aggregation is reduced. In one embodiment, the medical condition comprises a collagen-induced platelet disorder. In one embodiment, the platelet disorder is selected from the group consisting of atherosclerosis, coronary artery disease, ischemic cerebrovascular disease, peripheral vascular disease, diabetes mellitus, renal disease, inflammatory bowel disease, asthma, cystic fibrosis, rheumatoid arthritis, Kawasaki disease, tumor growth and metastasis, Alzheimer's disease, psychiatric disorders, thrombocytopenia, platelet function defects, von Willebrand disease, immune thrombocytopenia purpura, and inherited and acquired disorders of platelet function.

In one embodiment, the present invention contemplates a peptide inhibitor comprising an amino acid sequence consisting of $X_1$-$X_2$-$X_3$-$X_4$-G-L-V-K-I-L-L-R-I-L-R-V-L-L-P-G-$X_5$-$X_6$ (SEQ ID NO: 3), wherein $X_1$ consists of G or nothing; and $X_2$, $X_3$, $X_4$, $X_5$, and $X_6$ consist of K, R, or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide inhibitor includes amino acids selected from the group including, but not limited to, L-amino acids, or D-amino acids.

In one embodiment, the present invention contemplates a method comprising: a) providing; i) a patient having a medical condition resulting from platelet aggregation; and ii) a peptide inhibitor comprising an amino acid sequence consisting of $X_1$-$X_2$-$X_3$-$X_4$-G-L-V-K-I-L-L-R-I-L-R-V-L-L-P-G-$X_5$-$X_6$ (SEQ ID NO: 3), wherein $X_1$ consists of G or nothing; and $X_2$, $X_3$, $X_4$, $X_5$, and $X_6$ consist of K, R, or nothing capable of reducing said platelet aggregation; b) administering said inhibitor to said patient under conditions such that said aggregation is reduced. In one embodiment, the medical condition comprises a collagen-induced platelet disorder. In one embodiment, the platelet disorder is selected from the group consisting of atherosclerosis, coronary artery disease, ischemic cerebrovascular disease, peripheral vascular disease, diabetes mellitus, renal disease, inflammatory bowel disease, asthma, cystic fibrosis, rheumatoid arthritis, Kawasaki disease, tumor growth and metastasis, Alzheimer's disease, psychiatric disorders, thrombocytopenia, platelet function defects, von Willebrand disease, immune thrombocytopenia purpura, and inherited and acquired disorders of platelet function.

In one embodiment, the present invention contemplates a peptide inhibitor comprising an amino acid sequence consisting of $X_1$-$X_2$-C-G-L-V-R-I-I-L-G-A-V-$X_3$-G-I-L-I-I-L-C-$X_4$-$X_5$-$X_6$ (SEQ ID NO:4), wherein $X_1$ and $X_2$ consist of K, R, or nothing; $X_3$ consists of I or R; and $X_4$, $X_5$, and $X_6$ consist of K, R, or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-amino-dodecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide inhibitor includes amino acids selected from the group including, but not limited to, L-amino acids, or D-amino acids.

In one embodiment, the present invention contemplates a method comprising: a) providing; i) a patient having a medical condition resulting from platelet aggregation; and ii) a peptide inhibitor comprising an amino acid sequence consisting of $X_1$-$X_2$-C-G-L-V-R-I-I-L-G-A-V-$X_3$-G-I-L-I-I-L-C-$X_4$-$X_5$-$X_6$ (SEQ ID NO: 4), wherein $X_1$ and $X_2$ consist of K, R, or nothing; $X_3$ consists of I or R; and $X_4$, $X_5$, and $X_6$ consist of K, R, or nothing capable of reducing said platelet aggregation; b) administering said inhibitor to said patient under conditions such that said aggregation is reduced. In one embodiment, the medical condition comprises a collagen-induced platelet disorder. In one embodiment, the platelet disorder is selected from the group consisting of atherosclerosis, coronary artery disease, ischemic cerebrovascular disease, peripheral vascular disease, diabetes mellitus, renal disease, inflammatory bowel disease, asthma, cystic fibrosis, rheumatoid arthritis, Kawasaki disease, tumor growth and metastasis, Alzheimer's disease, psychiatric disorders, thrombocytopenia, platelet function defects, von Willebrand disease, immune thrombocytopenia purpura, and inherited and acquired disorders of platelet function.

In one embodiment, the present invention contemplates a peptide inhibitor comprising an amino acid sequence consisting of $X_1$-$X_2$-$X_3$-$X_4$-Y-T-I-L-R-F-I-L-G-L-A-K-V-A-L-I-$X_5$-$X_6$ (SEQ ID NO: 5), wherein X1 consists of G or nothing; and $X_2$, $X_3$, $X_4$, $X_5$ and $X_6$ consist of K, R, or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide inhibitor includes amino acids selected from the group including, but not limited to, L-amino acids, or D-amino acids.

In one embodiment, the present invention contemplates a method comprising: a) providing; i) a patient having a medical condition resulting from platelet aggregation; and ii) a peptide inhibitor comprising an amino acid sequence consisting of $X_1$-$X_2$-$X_3$-$X_4$-Y-T-I-L-R-F-I-L-G-L-A-K-V-A-L-I-$X_5$-$X_6$ (SEQ ID NO: 5), wherein X1 consists of G or nothing; and $X_2$, $X_3$, $X_4$, $X_5$ and $X_6$ consist of K, R, or nothing capable of reducing said platelet aggregation; b) administering said inhibitor to said patient under conditions such that said platelet aggregation is reduced. In one embodiment, the medical condition comprises a collagen-induced platelet disorder. In one embodiment, the platelet disorder is selected from the group consisting of atherosclerosis, coronary artery disease, ischemic cerebrovascular disease, peripheral vascular disease, diabetes mellitus, renal disease, inflammatory bowel disease, asthma, cystic fibrosis, rheumatoid arthritis, Kawasaki disease, tumor growth and metastasis, Alzheimer's disease, psychiatric disorders, thrombocytopenia, platelet function defects, von Willebrand disease, immune thrombocytopenia purpura, and inherited and acquired disorders of platelet function.

In one embodiment, the present invention contemplates a drug delivery system comprising a variant GPVI transmembrane peptide conjugated to a therapeutic drug. In one embodiment, the variant peptide comprises substituted amino acids that optimize hydrophobicity relative to SEQ ID NO:9. In one embodiment, the variant peptide comprises additional amino acids that optimize hydrophobicity relative to SEQ ID NO:9. In one embodiment, the variant peptide comprises additional and substituted amino acids that optimize hydrophobicity relative to SEQ ID NO: 9. In one embodiment, the variant peptide comprises substituted amino acids that optimize helicity relative to SEQ ID NO:9. In one embodiment, the variant peptide comprises additional amino acids that optimize helicity relative to SEQ ID NO:9. In one embodiment, the variant peptide comprises additional and substituted amino acids that optimize helicity relative to SEQ ID NO: 9. In one embodiment, the helicity comprises inherent helicity. In one embodiment, the helicity comprises induced helicity. In one embodiment, the helicity comprises α-helices. In one embodiment, the therapeutic drug is selected from the group including, but not limited to, anti-cancer drugs, anti-inflammatory drugs, psychotropic drugs, anti-depressant drugs, stimulant drugs, anti-diabetic drugs, cardiovascular drugs, anti-thrombotic drugs, anti-proliferative drugs, or cytotoxic drugs.

In one embodiment, the present invention contemplates a protease-resistance immunotherapeutic peptide comprising a variant GPVI transmembrane peptide. In one embodiment, the variant peptide comprises at least one D-amino acid.

In one embodiment, the present invention contemplates a medical device comprising a coating, wherein said coating comprises the peptide derivative of Claim 1. In one embodiment, the coating further comprises a polymer. In one embodiment, the polymer is selected from the group including, but not limited to, phosphorylcholine, polyvinyl pyrrolidone, poly(acrylic acid), poly(vinyl acetamide), poly(propylene glycol), poly(ethylene co-vinyl acetate), poly(n-butyl methacrylate) or poly(styrene-b-isobutylene-b-styrene). In one embodiment, the medical device is selected from the group including, but not limited to, stents, grafts, catheters, endoscopes (i.e., for example, laparoscopes), atrial/venous fistulas, or cannulae.

Definitions

The term "platelet aggregation", as used herein, refers to the clumping together of platelets or red blood cells.

The term "inhibiting platelet aggregation", as used herein, refers to the slowing of platelet aggregation, as well as completely eliminating and/or preventing platelet aggregation.

The term, "inhibiting platelet function", as used herein, refers to decreasing platelet function, as well as completely eliminating and/or preventing the platelet function.

The term, "treating a disease or condition", as used herein, refers to modulating platelet aggregation including, but not limited to, decreasing the amount of platelet aggregation and/or slowing platelet aggregation, as well as completely eliminating and/or preventing platelet aggregation. Diseases and/or conditions treatable by modulating platelet aggregation include, but are not limited to, embolus formation, thrombolytic complications, thrombosis, coronary heart disease, thromboembolic complications, myocardial infarction, restenosis, atrial thrombosis induction of atrial fibrillation, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic exposure to cardiovascular devices. Such conditions may also result from thromboembolism and re-occlusion during and after thrombolytic therapy, after angioplasty, and after coronary artery bypass.

The term "collagen-induced platelet aggregation", as used herein, refers to platelet aggregation in response to the presence of the protein collagen.

The term, "subject" or "patient", as used herein, refers to any individual organism. For example, the organism may be a mammal such as a primate (i.e., for example, a human). Further, the organism may be a domesticated animal (i.e., for example, cats, dogs, etc.), livestock (i.e., for example, cattle, horses, pigs, sheep, goats, etc.), or a laboratory animal (i.e., for example, mouse, rabbit, rat, guinea pig, etc.).

The term, "therapeutically effective amount", "therapeutically effective dose" or "effective amount", as used herein, refers to an amount needed to achieve a desired clinical result or results (treating or preventing platelet aggregation) based upon trained medical observation and/or quantitative test results. The potency of any administered peptide or compound determines the "effective amount" which can vary for the various compounds that inhibit platelet aggregation (i.e., for example, compounds inhibiting collagen-induced platelet aggregation). Additionally, the "effective amount" of a compound may vary depending on the desired result, for example, the level of platelet aggregation inhibition desired. The "therapeutically effective amount" necessary for inhibiting platelet aggregation may differ from the "therapeutically effective amount" necessary for preventing platelet aggregation.

The term, "agent", as used herein, refers to any natural or synthetic compound (I.e., for example, a peptide, a peptide variant, or a small molecule).

The term, "composition", as used herein, refers to any mixture of substances comprising a peptide and/or compound contemplated by the present invention. Such a composition may include the substances individually or in any combination.

The term, "intrinsic helicity", as used herein, refers to the helicity which is adopted by a peptide in an aqueous solution.

The term, "induced helicity", as used herein, refers to the helicity which is adopted by a peptide when in the presence of a helicity inducer, including, but not limited to, trifluoroethanol (TFE), detergents (i.e., for example, sodium dodecyl sulfate (SDS)), or lipids (i.e., for example, lipid vesicles (SUVs and/or LUVs as described herein).

The term "therapeutic drug", as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars. Drugs or compounds may have any of a variety of activities, which may be stimulatory or inhibitory, such as antibiotic activity, antiviral activity, antifungal activity, steroidal activity, cytotoxic, cytostatic, anti-proliferative, anti-inflammatory, analgesic or anesthetic activity, or can be useful as contrast or other diagnostic agents.

The term "effective dose" as used herein refers to the concentration of any compound or drug contemplated herein that results in a favorable clinical response. In solution, an effective dose may range between approximately 1 ng/ml-100 mg/ml, preferably between 100 ng/ml-10 mg/ml, but more preferably between 500 ng/ml-1 mg/ml.

The term "administered" or "administering" a drug or compound, as used herein, refers to any method of providing a drug or compound to a patient such that the drug or compound has its intended effect on the patient. For example, one method of administering is by an indirect mechanism using a medical device such as, but not limited to a catheter, syringe etc. A second exemplary method of administering is by a direct mechanism such as, local tissue administration (i.e., for example, extravascular placement), oral ingestion, transdermal patch, topical, inhalation, suppository etc.

The term "antiplatelets" or "antiplatelet drug" as used herein, refers to any drug that prevents aggregation of platelets or fibrin formation (i.e., for example as a prior event to adhesion formation). For example, an antiplatelet drug comprises an inhibitor of either glycoprotein VI (GPVI) or glycoprotein IIb/IIIba (GPIIb/IIIa). A GPVI inhibitor includes variant peptide inhibitors as described herein. Further, a GPIIb/IIIa inhibitor includes, but is not limited to, xemilofiban, abciximab (ReoPro®) cromafiban, elarofiban, orbofiban, roxifiban, sibrafiban, RPR 109891, tirofiban (Aggrastat®), eptifibatide (Integrilin®), UR-4033, UR-3216 or UR-2922.

The term, "antithrombins" or "antithrombin drug" as used herein, refers to any drug that inhibits or reduces thrombi formation and include, but are not limited to, bivalirudin, ximelagatran, hirudin, hirulog, argatroban, inogatran, efegatran, or thrombomodulin.

The term, "anticoagulants" or "anticoagulant drug" as used herein, refers to any drug that inhibits the blood coagulation cascade. A typical anticoagulant comprises heparin, including but not limited to, low molecular weight heparin (LMWH) or unfractionated heparin (UFH). Other anticoagulants include, but are not limited to, tinzaparin, certoparin, pamaparin, nadroparin, ardeparin, enoxaparin, reviparin or dalteparin. Specific inhibitors of the blood coagulation cascade include, but are not limited to, Factor Xa (FXa) inhibitors (i.e., for example, fondaparinux), Factor IXa (FIXa) inhibitors, Factor XIIIa (FXIIIa) inhibitors, and Factor VIIa (FVIIa) inhibitors.

The term "medical device", as used herein, refers broadly to any apparatus used in relation to a medical procedure. Specifically, any apparatus that contacts a patient during a medical procedure or therapy is contemplated herein as a medical device. Similarly, any apparatus that administers a drug or compound to a patient during a medical procedure or therapy is contemplated herein as a medical device. "Direct medical implants" include, but are not limited to, urinary and intravascular catheters, dialysis catheters, wound drain tubes, skin sutures, vascular grafts and implantable meshes, intraocular devices, implantable drug delivery systems and heart valves, and the like. "Wound care devices" include, but are not limited to, general wound dressings, non-adherent dressings, burn dressings, biological graft materials, tape closures and dressings, surgical drapes, sponges and absorbable hemostats. "Surgical devices" include, but are not limited to, surgical instruments, endoscope systems (i.e., catheters, vascular catheters, surgical tools such as scalpels, retractors, and the like) and temporary drug delivery devices such as drug ports, injection needles etc. to administer the medium. A medical device is "coated" when a medium comprising an antiplatelet drug (i.e., for example, a variant GPVI peptide) becomes attached to the surface of the medical device. This attachment may be permanent or temporary. When temporary, the attachment may result in a controlled release of a variant GPVI peptide.

The term "endoscope" refers to any medical device that is capable of being inserted into a living body and used for tasks including, but not limited to, observing surgical procedures, performing surgical procedures, or applying medium to a surgical site. An endoscope is illustrated by instruments including, but not limited to, an arthroscope, a laparoscope, hysteroscope, cytoscope, etc. It is not intended to limit the use of an endoscope to hollow organs. It is specifically contemplated that endoscopes, such as an arthroscope or a laparoscope is inserted through the skin and courses to a closed surgical site.

The term "vascular access site" is defined herein as referring to any percutaneous insertion of a medical device into the vasculature. For example, a hemodialysis catheter placement comprises a vascular access site. Such sites may be temporary (i.e., placed for a matter of hours) or permanent (i.e., placed for days, months or years).

The term "vascular graft" as used herein, refers to any conduit or portion thereof intended as a prosthetic device for conveying blood and, therefore, having a blood contacting surface (i.e., "luminal"). While usually in a tubular form, the graft may also be a sheet of material useful for patching portions of the circumference of living blood vessels (these materials are generally referred to as surgical wraps). Likewise, the term vascular graft includes intraluminal grafts for use within living blood vessels. The inventive grafts as such may also be used as a stent covering on the exterior, luminal or both surfaces of an implantable vascular stent.

The term "synthetic vascular graft" as used herein, refers to any artificial tube or cannula designed for insertion into a blood vessel. Such grafts may be constructed from polytetrafluoroethylene (PTFE).

The term "syringe" or "catheter" as used herein, refers to any device or apparatus designed for liquid administration, as defined herein. A syringe or catheter may comprise at least one storage vessel (i.e., for example, a barrel) wherein a single medium resides prior to administration. A syringe or catheter comprising two or more barrels, each containing a separate medium, may mix the media from each barrel prior to administration or the media of each barrel may be administered separately. One of skill in the art will recognize that any catheter designed to perform dialysis, as defined herein, may also administer liquids.

The term "dialysis/apheresis catheter" as used herein, refers to any multi-lumen catheter (i.e., for example, a triple lumen catheter) capable of providing a simultaneous withdrawal and return of blood to a patient undergoing a blood treatment process. Apheresis (called also pheresis) comprises a blood treatment process involving separation of blood elements that can remove soluble drugs or cellular elements from the circulation. Deisseroth et al., "Use Of Blood And Blood Products", Cancer: Principles And Practice Of Oncology, Devita, V. T. Jr. et al. Editors, Philadelphia: J. B. Lippincott Company 1989, p. 2045-2059. For example, blood is withdrawn from a donor, some blood elements (i.e., for example, plasma, leukocytes, platelets, etc.) are separated and retained. The unretained blood elements are then retransfused into the donor.

The term "dialysis catheter" as used herein, refers to any device capable of removing toxic substances (impurities or wastes) from the body when the kidneys are unable to do so. A dialysis catheter may comprise a single catheter having at least a dual lumen (i.e., one lumen withdraws arterial blood and a second lumen returns the dialyzed blood to the venous system) or involve placing two catheters—one that is placed in an artery, and one in an adjacent vein. Dialysis catheters are most frequently used for patients who have kidney failure, but may also be used to quickly remove drugs or poisons in acute situations.

The term "peritoneal dialysis catheter" as used herein, refers to any continuous flow catheters with at least two lumens, one of which is a short lumen (used to infuse a dialysis solution into the peritoneum), and the other of which is a long coiled lumen having a plurality of openings, generally located on the inside of the coil. It is believed that peritoneal solutes enter into the coiled lumen openings and are thereby removed from the peritoneum. One hypothesis suggests that peritoneal dialysis works by using the peritoneal membrane inside the abdomen as the semipermeable membrane. Special solutions that facilitate removal of toxins may be infused in, remain in the abdomen for a time, and then drained out.

The term "fixed split-tip dialysis catheter" as used herein, refers to any catheter having at least two distinct elongated end portions that extend substantially parallel to the longitudinal axis of the catheter and are flexible to the lateral displacement of an infused fluid. It is believed that this flexibility prevents a permanent catheter tip splay that is known to injure tissue. Usually a fixed-tip dialysis catheter provides indwelling vascular access for patients undergoing long-term renal dialysis care (i.e., for example, end-stage renal disease).

The term "femoral catheter" as used herein, refers to any catheter that is inserted into the femoral vein. Femoral catheters are typically provided for intermediate term blood access because the superior vena cava is relatively close to the right atrium of the heart, the minimal range of shape changes of these veins with natural movements of the patient (to minimize the damage to the vessel intima), and because of good acceptance by the patients of the skin exit on the thoracic wall. Further, the femoral veins are easy to cannulate, so that catheters of this invention may be inserted into the femoral veins at the bed side.

The term "attached" as used herein, refers to any interaction between a medium (or carrier) and a therapeutic drug. Attachment may be reversible or irreversible. Such attachment includes, but is not limited to, covalent bonding, and non-covalent bonding including, but not limited to, ionic bonding, Van der Waals forces or friction, and the like. A drug is attached to a medium (or carrier) if it is impregnated, incorporated, coated, in suspension with, in solution with, mixed with, etc.

The term "covalent bonding" as used herein, refers to an attachment between two compounds (I.e., for example, a medium and a drug) that comprising a sharing of electrons.

The term "placing" as used herein, refers to any physical relationship (i.e., secured or unsecured) between a patient's biological tissue and a surgical material, wherein the surgical material comprises a pharmaceutical drug that may be, optionally, attached to a medium. Such a physical relationship may be secured by methods such as, but not limited to, gluing, suturing, stapling, spraying, laying, impregnating, and the like.

The term "parts by weight", as used herein, when used in reference to a particular component in a composition denotes the weight relationship between the component and any other components in the composition for which a pan by weight is expressed.

The term "protecting groups", as used herein, refer to those groups which prevent undesirable reactions (such as proteolysis) involving unprotected functional groups. In one embodiment, the present invention contemplates that the protecting group is an acyl or an amide. In one embodiment, the acyl is acetate. In another embodiment, the protecting group is a benzyl group. In another embodiment, the protecting group is a benzoyl group. The present invention also contemplates combinations of such protecting groups.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 5B shows one embodiment of a fluorescence resonance energy transfer (FRET) assay that could be used in high-throughput screening strategies to identify both peptide and nonpeptide inhibitors of protein-protein interaction between GPVI and FcRγ subunits of the GPVI-FcRγ signaling complex. CFP: cyan fluorescent protein; YFP: yellow fluorescent protein.

FIG. 5C shows one embodiment of an enzyme-linked immunosorbent assay (ELISA) that could be used in high-throughput screening strategies to identify both peptide and nonpeptide inhibitors of protein-protein interaction between GPVI and FcRγ subunits of the GPVI-FcRγ signaling complex. HRP: horseradish peroxidase.

DETAILED DESCRIPTION OF THE INVENTION

Figure 1A:
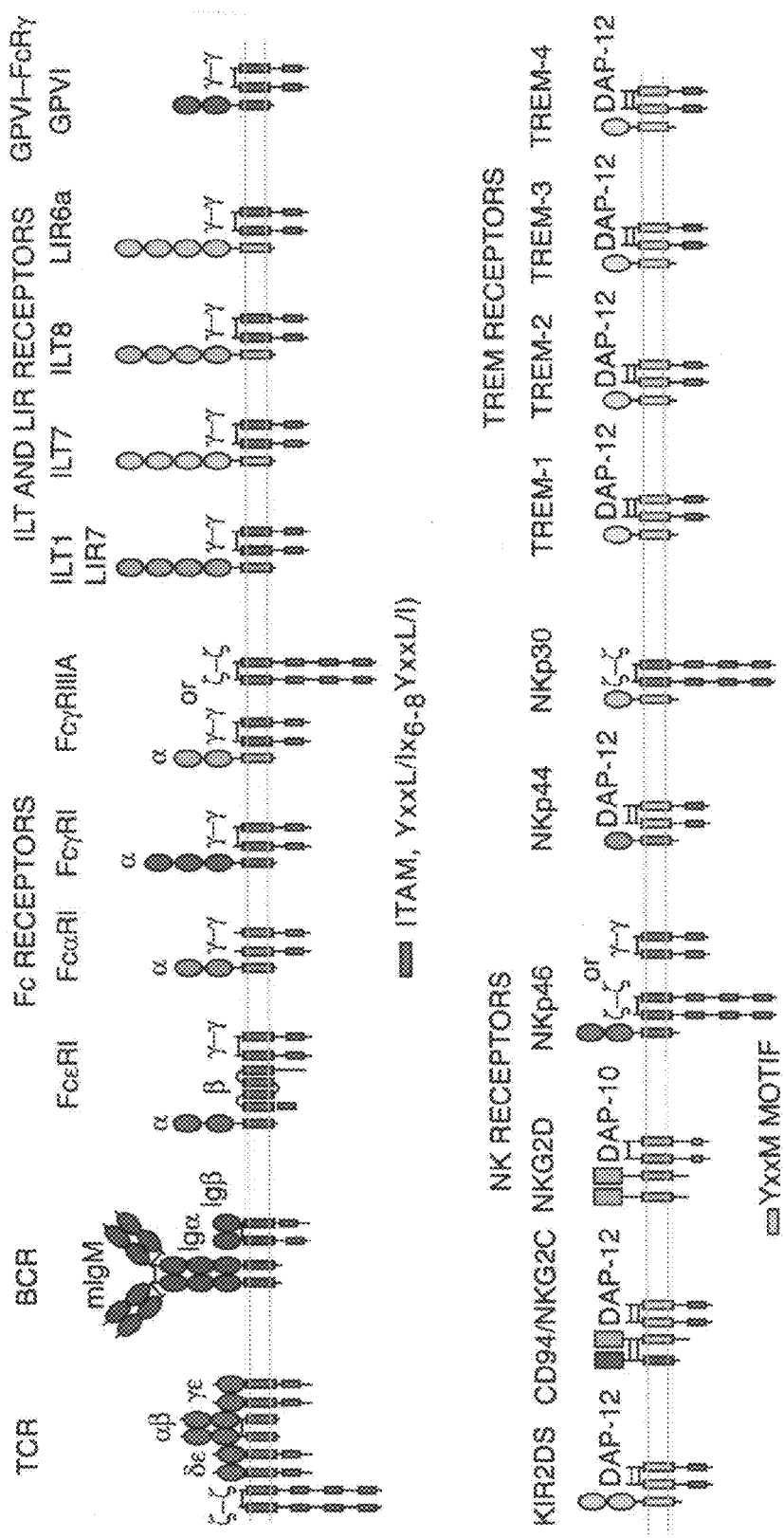
FIG. 1A presents a schematic representation of one embodiment of a Multichain Immune Recognition Receptor (MIRR) expressed on many different immune cells—including T and B cells, natural killer cells, mast cells, macrophages, basophils, neutrophils, eosinophils and dendritic cells—and on platelets. Position of MIRRs relative to the cell membrane is indicated by blue lines. Abbreviations: BCR, B-cell receptor; GPVI, glycoprotein VI; ILT, Ig-like transcript; KIR, killer cell Ig-like receptor; LIR, leukocyte Ig-like receptor; NK, natural killer cell; TREM, triggering receptor expressed on myeloid cells.

The present invention relates to peptides and compounds which affect platelets by action on the collagen receptor, glycoprotein VI. The present invention further relates to the treatment or prevention of a disease or condition involving platelet activation and aggregation and, more particularly, collagen-induced platelet activation and aggregation. In one embodiment, GPVI-FcRγ signaling is inhibited by variant peptides binding to the transmembrane region of the FcRγ subunit.

Various methods of application are proposed to use these protein variants including, but not limited to; i) treating diseases or other medical conditions involving platelet activation and aggregation; ii) drug delivery systems; iii) a sequence-based rational drug design method; iv) protease-resistance immunotherapeutic peptides; v) coatings of medical devices, such as cardiovascular stents.

The present invention contemplates constructing a series of variant peptides homologous to a transmembrane core sequence of the glycoprotein VI (GPVI) receptor. The GPVI-FcRγ-coupled collagen receptor signaling pathway resident within blood platelet membranes represents but one mechanism responsible for platelet activation. Although it is not necessary to understand the mechanism of an invention, it is believed that these variant peptides insert themselves into the platelet membrane and act as a "receptor decoy" for collagen molecules. It is further believed that GPVI-FcRγ platelet activation requires the bridging of multiple GPVI-FcRγ-coupled collagen receptors that generates an intracellular activation signal (i.e., for example, by inositol triphosphate stimulated $Ca^{2+}$ entry) by bringing membrane-embedded FcRγ subunits into close proximity. These GPVI-like peptide variants may prevent platelet activation by reducing FcRγ-FcRγ aggregation by generating GPVI-FcRγ/peptide variant bridges in the presence of collagen. It is further believed that the molecular basis for the prevention of platelet activation is based upon protein-protein interactions.

Protein-protein interactions are involved in most biological processes and thus represent an appealing target for innovative drug development. These interactions can be targeted by small molecule inhibitors, peptides, and peptidomimetics. Consequently, indirect protein therapy that alters protein-protein interactions represents an alternative to direct protein therapeutics (i.e., for example, immunotherapy) and avoids dangerous side effects. Indirectly acting peptides may serve as active regulators and participate in molecular cross talk, which drives metabolic processes. These indirectly acting peptides are also extremely potent, showing high specificity, and have few toxicological problems. Moreover, these indirectly acting peptides do not accumulate in organs or suffer from drug-drug interactions as many small molecules do. They can be used as therapeutic agents, or as a starting point for developing peptidomimetics and small molecular weight inhibitors.

I. The Role of Collagen in Vascular Homeostasis

Thrombus formation following platelet aggregation can lead to vasoclusion, ischemia, or infarction. In healthy, undamaged tissues, collagens which support the blood vessel wall and surrounding tissue are concealed by endothelial cell layers and cannot come into contact with the circulating platelets. However, should the endothelial cell layer be removed, either in disease or upon tissue injury, then collagens are exposed which can interact with the cellular components of the blood as well as with proteins in blood plasma. The platelet surface contains a series of protein receptors which sense the presence in the extracellular medium of specific molecules, including hormones, cytokines, and other species. Collagen can bind directly to several such receptors on the platelet surface.

Only recently, glycoprotein VI (GPVI) has been established as a platelet collagen receptor that mediates platelet adhesion and aggregation on immobilized collagen in vitro, and the activation of different adhesive receptors. Nieswandt et al., "Glycoprotein V1 but not alpha$_2$beta$_1$ integrin is essential for platelet interaction with collagen" *EMBO J.* 20:2120-2130 (2001). Signaling by the GPVI receptor has been shown to be involved in the activation of platelets by collagen.

Platelet collagen receptors are attractive targets for anti-thrombotic therapy. GPVI seems particularly attractive in this respect since its expression is confined to the platelet and its precursor, the megakaryocyte. Since its detection, the function of GPVI in platelet-collagen interactions and the signal transduction pathway induced by GPVI has been extensively studied. The selective inhibition of GPVI and/or its signaling is thought by most workers in the field to inhibit thrombosis without affecting hemostatic plug formation, thus providing new therapeutic strategies to fight platelet-mediated disease. In: *Platelets*, Alan D. Michelson (ed.) Academic Press (2002); Farndale, P. W. "Collagen-induced platelet activation" *Blood Cells, Molecules, and Diseases* 36:162-165 (2006); Moroi et al., "Platelet glycoprotein VI: its structure and function" *Thrombosis Research* 114:221-233 (2004); and Gawaz, M., "Role of platelets in coronary thrombosis and reperfusion of ischemic myocardium" *Cardiovascular Research* 61:498-511 (2004).

Currently, very few approaches have pursued an inhibition of GPVI-mediated transmembrane signaling. Antibodies that specifically recognize GPVI binding to its receptor have been used to prevent collagen binding and initiation of platelet aggregation. Busfield et al., "Glycoprotein VI antibodies and uses thereof" U.S. Pat. No. 6,989,144 (herein incorporated by reference in its entirety); and Matsumoto et al., "Highly potent anti-human GPVI monoclonal antibodies derived from GPVI knockout mouse immunization" *Thromb. Res.*

E-pub: dx.doi.org/10.1016/j.thromres.2006.01.023. One chemosensitizing antileukemic agent with antithrombotic properties, LFM-A13, has been suggested as a potential inhibitor of collagen-induced platelet aggregation. This compound, however, poses serious disadvantages such as toxicity and other side effects. Uckun F., "Inhibiting collagen-induced platelet aggregation" U.S. Pat. No. 6,589,992 (herein incorporated by reference in its entirety).

II. Multichain Immune Recognition Receptors (MIRRs)

Figure 1B:
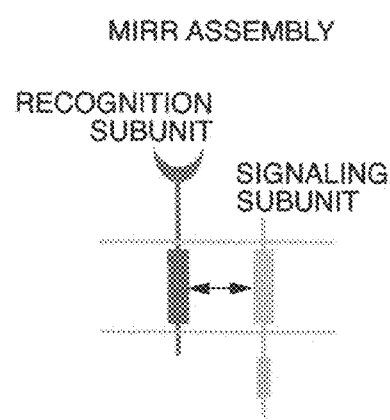
FIG. 1B presents a schematic representation of one possible structural and functional organization of MIERs. Although it is not necessary to understand the mechanism of an invention, it is believed that transmembrane intersubunit heterointeractions between MIRR recognition and signaling components (shown by arrows) have a role in receptor assembly and integrity on resting cells.

Multichain immune recognition receptors (MIRRs) are believed to recognize foreign antigens and initiate many biological responses. MIRR-mediated signal transduction plays a role in health and disease, making these receptors attractive targets for rational drug design efforts in the treatment of several immune disorders. Thus, therapeutic strategies contemplated herein involve MIRR triggering and subsequent transmembrane signaling. Most members of the MIRR family are believed to be multisubunit complexes that are formed by the association of recognition subunits with signal-transducing subunits. Usually, MIRR subunits have a cytoplasmic domain comprising an Immunoreceptor Tyrosine-Based Activation Motif (ITAM) or an YxxM motif, which is found in the DAP-10 cytoplasmic domain. See, FIG. 1A. In resting cells, this association is driven mostly by the noncovalent transmembrane interactions between recognition and signaling components and plays a role in receptor assembly and integrity (See, FIG. 1B). [1-7]. Ligand binding, however, induces receptor crosslinking thereby resulting in the phosphorylation of the ITAM or YxxM tyrosines and triggering an elaborate intracellular signaling cascade. The sequence of biochemical events that ensues after the phosphorylation of ITAMs or YxxM is understood in significant detail; however, the molecular mechanism linking the extracellular clustering of ligand-binding MIRR subunits to the intracellular phosphorylation of signaling subunits remains to be identified.

In one embodiment, the present invention contemplates therapeutic targets compatible with a model of MIRR triggering and subsequent transmembrane signal transduction; the Signaling Chain HomO-OLigomerization (SCHOOL) model. Although it is not necessary to understand the mechanism of an invention, it is believed that the structural similarity of the MIRRs provides the basis for the similarity in the mechanisms of MIRR-mediated signaling. It is further believed that a general pharmaceutical approach based upon this SCHOOL model can be used to treat diverse immune-mediated diseases.

1. SCHOOL Model of MIRR Signaling

Recently, a novel model of MIRR-mediated transmembrane signal transduction mechanism has been suggested. Sigalov, A. B., "Multichain immune recognition receptor signaling: different players, same game?" *Trends Immunol.* 25:583-589 (2004); and Sigalov, A., "Multi-chain immune recognition receptors: spatial organization and signal transduction" *Semin. Immunol.* 17:51-64 (2005); and [8]. This model is fundamentally different from those previously suggested since it is based on specific protein-protein interactions. These interactions reflect biochemical processes that can be influenced and controlled, thus revealing new therapeutic targets. See, FIG. 1C. According to this novel mechanistic model, the Signaling Chain HOmoOLigomerization (SCHOOL) model, inhibition of MIRR signaling can be achieved by disruption of transmembrane interactions between MIRR. recognition and signaling subunits. See, FIG. 1D.

Figure 1C:
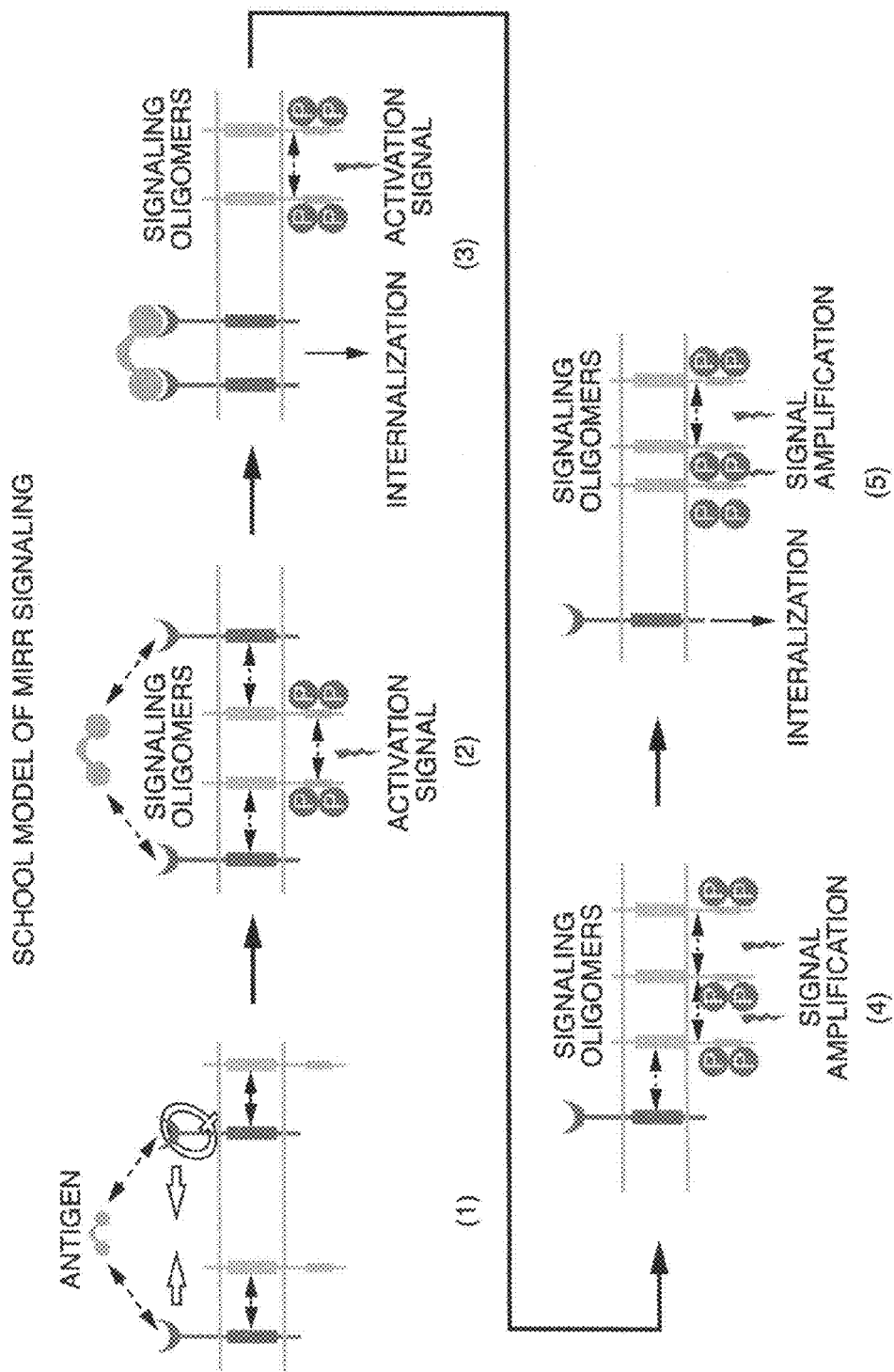
FIG. 1C illustrates one embodiment of a MIRR-mediated transmembrane signal transduction utilizing the signaling chain homooligomerization (SCHOOL) model. c) The SCHOOL model, which indicates that the homo-oligomerization of signaling subunits has a role in triggering MIRR-mediated transmembrane signal transduction. Ligand-binding chains and signaling subunits are shown in red and orange, respectively. Small unbroken black arrows indicate specific intersubunit hetero- and homointeractions between transmembrane and cytoplasmic domains. Although it is not necessary to understand the mechanism of an invention, it is believed that ligand-induced MIRR clustering leads to receptor reorientation and formation of a dimeric or oligomeric intermediate in which signaling chains from different receptor units start to trans-homointeract and form signaling oligomers (steps 1,2). All interchain interactions in this intermediate are denoted by broken black arrows, reflecting their transition state. It is further believed that upon the formation of signaling oligomers, protein tyrosine kinases phosphorylate the tyrosine residues in the ITAMs (green rectangles) or the YxxM motif of DAP-10 (blue rectangles), leading to transmembrane transduction of activation signal, dissociation of signaling oligomers and internalization of the engaged MIRR-binding domains (steps 2,3). Next, the signaling oligomers are believed to sequentially homointeract with the relevant signaling subunits of non-engaged receptors, resulting in the formation of higher signaling oligomers, thus propagating and amplifying the signals (steps 4,5). This may lead to the release and subsequent internalization of the non-engaged ligand-binding domains. A similar general scheme can be considered for the pathway induced by receptor crosslinking, using antibodies to signaling subunits (e.g. anti-CD3e or anti-Igb antibodies for TCRs and BCRs, respectively). Abbreviation: P, phosphate.
Figure 1D:
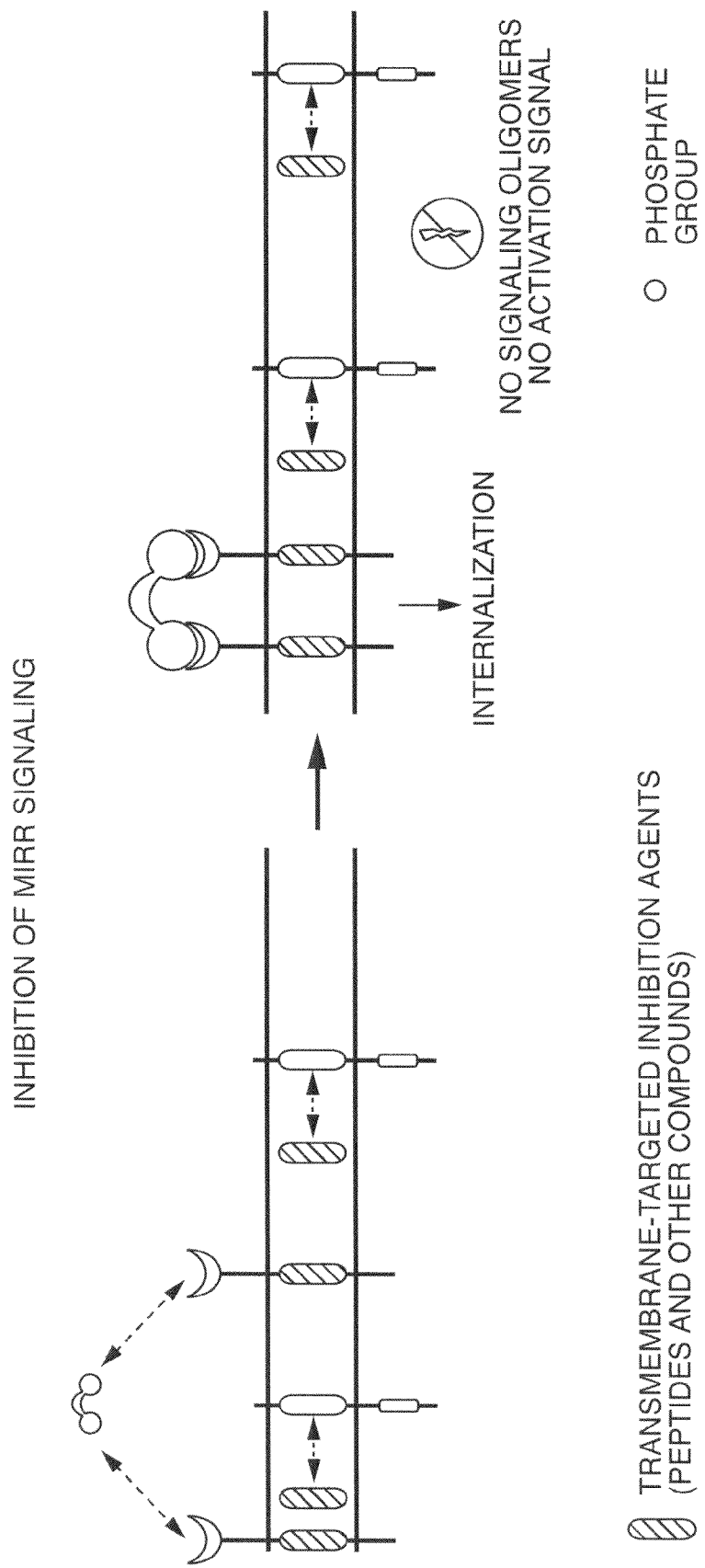
FIG. 1D illustrates one embodiment of a specific blockade of transmembrane interactions between recognition and signaling subunits resulting in "pre-dissociation" of the receptor complex, thus preventing formation of signaling oligomers and inhibiting antigen-dependent immune cell activation.

Hypotheses regarding possible physiological roles of these unique homointeractions indicates that MIRR engagement leads to receptor oligomerization coupled with a multistep structural reorganization driven by the homo-oligomerization of MIRR signaling subunits. FIG. 1C, and [9,10] One possibility is that MIRR triggering may be a result of ligand-induced interplay between intra-receptor transmembrane interactions that stabilize and maintain receptor integrity. Further, inter-receptor homointeractions between the cytoplasmic domains of MIRR signaling subunits may lead to the formation of oligomeric signaling structures, thus triggering the phosphorylation of ITAMs and initiating the signaling cascade. It is believed that this model is based on specific protein-protein interactions—biochemical processes that can be influenced and controlled—and assumes that the general principles underlying MIRR-mediated transmembrane signaling mechanisms are similar. [11] In one embodiment, the present invention contemplates that the SCHOOL model may be used to develop similar therapeutic strategies targeting protein-protein interactions that are involved in MIRR triggering and transmembrane signaling can be used to treat diverse immune-mediated diseases.

2. SCHOOL Model: Trinity of Description, Explanation and Prediction

Although it is not necessary to understand the mechanism of an invention, it is believed that the SCHOOL model describes molecular mechanisms of transmembrane signal transduction for functionally unrelated receptors that share a common structural and organizing principle—extracellular recognition module(s) and intracellular signaling module(s) are found on separate subunits and are noncovalently associated through their transmembrane domains. Thus, it is further believed that the basic principles of transmembrane signaling predicted by the SCHOOL model can be used in different fields of immunology and cell biology to describe processes that are mediated by structurally related but functionally different membrane receptors. The SCHOOL model provides a mechanistic explanation for specific processes behind 'outside-in' MIRR signaling that the art has presently been unable to solve. Selected examples of these 'outside-in' processes are:

(i) the role of proper orientation and suitable proximity of receptors in antigen-crosslinked MIRR clusters in initiating transmembrane signaling [12-15];
(ii) the observation that different MIRR signaling subunits within the receptor engage partially distinct signaling pathways [16,17];
(iii) the dissociation of MIRR signaling chains from the remaining receptor subunits in activated cells [18-20];
(iv) the exposure of the CD3e cytoplasmic epitope during T-cell activation [21];
(v) lateral signal propagation and amplification in the immunological synapse [22, 23];
(vi) the action of the HIV-1 gp41 fusion peptide (FP) and synthetic transmembrane peptides inhibiting antigen-stimulated T-cell receptor (TCR) signaling [24,25].

Further, the SCHOOL model could have been used to predict several experimental observations following its initial disclosure: [9]: (i) in T cells, the dimerization of CD3e is sufficient to stimulate pre-TCR function [26]; (ii) in B cells, antigen stimulation physically separates the Iga-b signaling heterodimer from the m-heavy chain [19]; and (iii) FceRI-activated mast cells propagate signals from small signaling domains formed around dimerized or oligomerized receptors [27].

Further development of effective anti-thrombotic agents which prevent collagen-induced platelet aggregation and activation depends on an improved understanding of the glycoprotein GPVI-FcRγ-coupled collagen receptor signaling pathway. Upon stimulation by collagen, GPVI signals through a noncovalently associated immune receptor adaptor FcRγ, a transmembrane protein that mediates signaling by several immune receptors through an immunoreceptor tyrosine activation motif (ITAM).

In this regard, a GPVI receptor is structurally homologous to multichain immune recognition receptors (MIRRs). Most members of the MIRR family are multisubunit complexes formed by the association of recognition subunits with ITAM-containing signal-transducing subunits. This association in resting cells is mostly driven by the noncovalent transmembrane interactions between recognition and signaling components and plays a role in receptor assembly and integrity. Crosslinking of the receptors after ligand binding results in phosphorylation of the ITAM tyrosines, which triggers the elaborate intracellular signaling cascade. The molecular mechanism linking extracellular clustering of MIRR ligand-binding subunits to intracellular phosphorylation of signaling subunits remains to be identified. In this regard, the mechanisms of GPVI transmembrane signaling has been also elusive, thus hindering the further development of promising therapeutic strategies for the treatment/prophylaxis of platelet-mediated disease.

The SCHOOL model suggests that therapeutic strategies, aiming to inhibit MIRR signaling, can be applied to treat and/or prevent many functionally unrelated, immune cell-mediated diseases. Ligand-induced MIRR clustering leads to receptor reorientation and formation of a dimeric/oligomeric intermediate in which signaling chains from different receptor units start to transhomeointeract and form signaling oligomers. Upon formation of signaling oligomers, protein tyrosine kinases phosphorylate the tyrosine residues in the ITAMs that lead to transmembrane transduction of activation signal, dissociation of signaling oligomers, and internalization of the engaged MIRR binding domains.

Figure 2A:
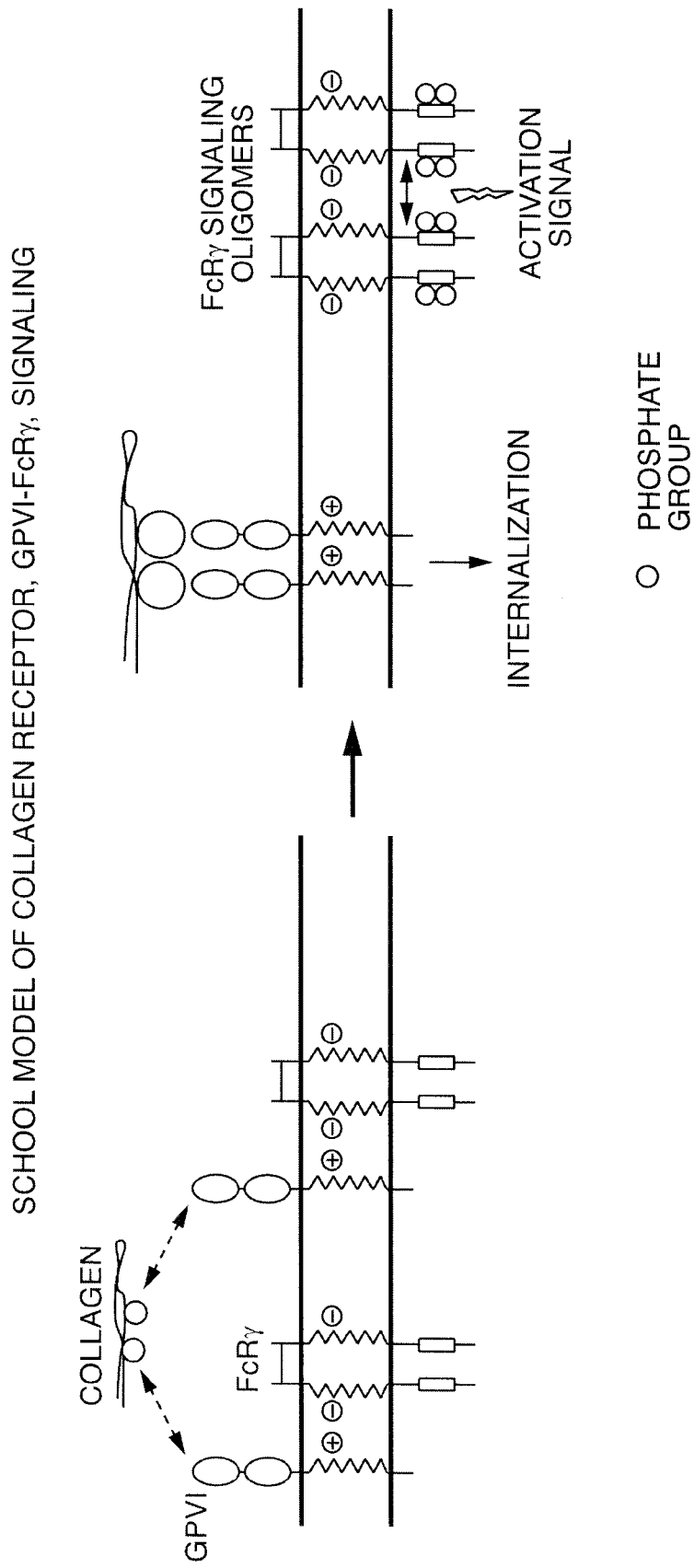
FIG. 2A illustrates one embodiment of a SCHOOL model of GPVI-mediated transmembrane signal transduction and its inhibition. Solid arrows: Specific subunit homointeractions between cytoplasmic domains.
Figure 2B:
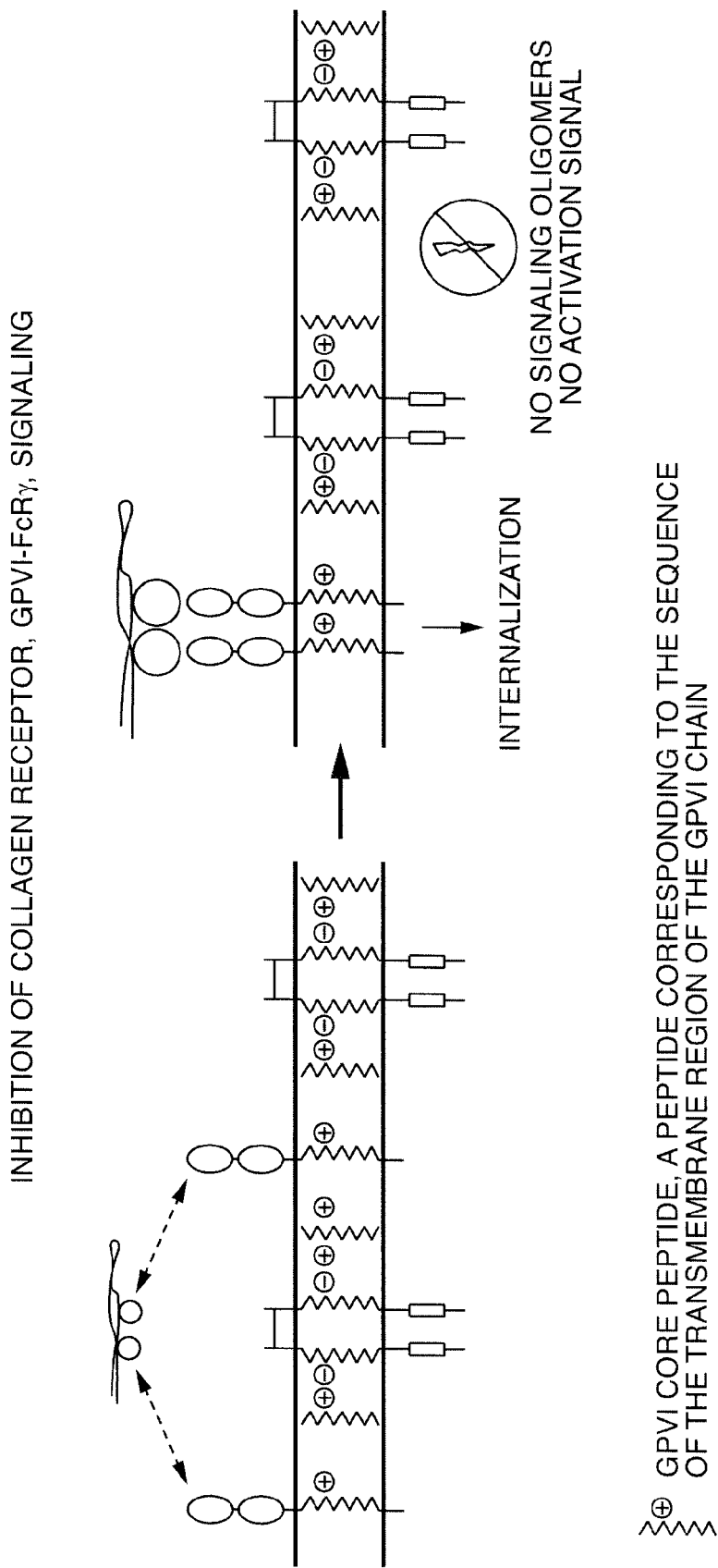
FIG. 2B illustrates one embodiment of a specific blockade of transmembrane interactions between GPVI and FcRγ signaling subunits resulting in "pre-dissociation" of a receptor complex.

Application of the SCHOOL model to the transmembrane signal transduction mediated by a collagen receptor (i.e., for example, glycoprotein VI) suggested that an inhibition of GPVI-FcRγ, signaling may be achieved by using transmembrane-targeted agents which specifically disrupt transmembrane interactions between GPVI and FcRγ subunits. For example, the simplest agents would be synthetic peptides corresponding to the GPVI transmembrane domain. Without being limited by a particular theory, the basic principles of one proposed mechanism by which peptides and other compound of the present invention may work by GPVI-mediated transmembrane signaling. See, FIGS. 2A & 2B.

It is believed that collagen-induced clustering of a GPVI-FcRγ receptor complex leads to formation of FcRγ signaling oligomers with subsequent phosphorylation of the ITAM-Tyr residues and transmembrane transduction of the platelet activation signal. See, FIG. 2A. This hypothesis suggests that a GPVI Core Peptide (GPVI-CP), a peptide corresponding to the transmembrane region of GPVI, penetrates the platelet membrane and competitively binds to the transmembrane domain of FcRγ chain, thus displacing a GPVI receptor from interacting with a signaling FcRγ subunit, thereby resulting in a "pre-dissociation" of a GPVI-FcRγ receptor complex. As a consequence, collagen-induced GPVI clustering does not lead to formation of FcRγ signaling oligomers and subsequent platelet activation and aggregation. See, FIG. 2B.

Normal transmembrane (TM) interactions between the GPVI and the FcRγ dimer forming a functional GPVI-FcRγ receptor complex comprise positively charged arginine amino acids within the GPVI transmembrane portion and negatively charged aspartic acid pairs in a FcRγ dimer, thereby allowing subunit association. See FIG. 3A. Although it is not necessary to understand the mechanism of an invention, it is believed that interactions between an arginine residue of a GPVI core peptide inhibitor and an aspartic acid residue of a FcRγ dimer disrupt the transmembrane interactions between the GPVI subunit and the dimeric FcRγ signaling chain, thereby "disconnecting" GPVI and result in a non-functioning collagen receptor. See FIG. 3B.

A. GPVI Peptides and Variants Thereof

Although it is not necessary to understand the mechanism of an invention, it is believed that a hydrophobic/polar/charged amino acid sequence patterning, rather than sequence similarity, within a TM GPVI domain plays a dominant role in the development of effective peptide-based inhibitors of platelet activation and aggregation. For example, despite the lack of sequence similarity, the fusion peptide (FP) in the N terminus of the HIV envelope glycoprotein, gp41, has been shown to inhibit T cell antigen receptor (TCR)-mediated T cell activation in vitro and in vivo more effectively than the transmembrane TCR core peptide (CP) with 100-fold lower the 50% inhibitory concentration (IC50) values for FP than those observed for CP.

In some embodiments, as contemplated by the present invention, optimal peptide inhibitors and peptide inhibitor analogues are designed using hydrophobic/polar/charged sequence pattern criteria and associated evaluation techniques. These peptide inhibitors may then be synthesized and tested in platelet function inhibition assays.

Listed below in Table 1 are reported transmembrane sequences of GPVI and FcRγ in a number of species. These regions are highly conserved and the substitutions between species are very conservative. This suggests a functional role for the transmembrane regions of both, GPVI and FcRγ, constituents of the complex. These regions strongly interact between themselves, thus maintaining the integrity of the collagen receptor signaling complex in resting platelets. These transmembrane domains are short and should be easily mimicked by synthetic peptides and compounds. Based on these features, and taking advantage of the SCHOOL model of MIRR signaling to explain GPVI-mediated platelet activation, the present invention contemplates a new approach of intervening and modulating GPVI function. In some embodiments, synthetic peptides and compounds are contemplated that may provide successful treatment options in the clinical setting.

TABLE 1

Sequence comparisons of glycoprotein VI and FcRγ transmembrane regions

| SPECIES | GPVI SEQUENCE | FcRγ SEQUENCE |
| --- | --- | --- |
| HUMAN | GNLVRICLGAVILIILAGFLA (SEQ ID NO: 8) | LCYILDAILFLYGIVLTLLYC (SEQ ID NO: 29) |
| MOUSE | GNLVRICLGATIIIILLGLLA (SEQ ID NO: 30) | LCYILDAVLFLYGIVLTLLYC (SEQ ID NO: 31) |
| BOVINE | Not Known | LCYILDAILFLYGIVLTLLYC (SEQ ID NO: 29) |
| MONKEY | Not Known | LCYILDAILFLYGIVLTLLYC (SEQ ID NO: 29) |
| RAT | Not Known | LCYILDAILFLYGIVLTLLYC (SEQ ID NO: 29) |
| PIG | Not Known | LCYILDAILFLYGIVLTLLYC (SEQ ID NO: 29) |

In one embodiment, the present invention contemplates a series of peptides that are inhibitors of a collagen receptor (i.e., for example, a GPVI-FcRγ complex) Although it is not necessary to understand the mechanism of an invention, it is believed that this inhibition is mediated by disrupting the transmembrane interactions between the recognition, GPVI, signaling, and FcRγ subunits. In other embodiments, these peptide inhibitors treat and/or prevent diseases and/or conditions comprising platelet activation and/or aggregation. In one embodiment, the peptide inhibitors mediate collagen-induced platelet activation and aggregation. In another embodiment, the present invention contemplates a drug delivery system comprising peptide inhibitors of the present invention. Although it is not necessary to understand the mechanism of an invention, it is believed that the peptide inhibitor drug delivery system functions by penetrating the platelet membrane.

Sequence-based rational design can be used as a tool in order to increase the effectiveness of the peptides to inhibit the function of the GPVI-FcRγ collagen receptor complex. For example, a conservative amino acid substitution of arginine for lysine or insertion of at least one supplemental positively charged amino acid residue (i.e., for example, arginine and/or lysine) may be made in certain locations on alpha-helixes of GPVI core or extended peptides. Although it is not necessary to understand the mechanism of an invention, it is believed that these changes should result in increased binding activity to the transmembrane domain of the FcRγ receptor complex signaling subunit dimer, thus enhancing the effectiveness of the peptides to inhibit the function of an GPVI-FcRγ receptor complex.

GPVI peptide inhibitors and variants thereof contemplated herein may be modified at the carboxy terminal without loss of activity. Accordingly, it is intended that the present invention includes within its scope, peptides which include additional amino acids to the "core" sequence of the peptide of the present invention and which affect the interaction of GPVI and FcRγ subunits of the GPVI-FcRγ signaling complex (i.e., for example, an Extended Peptide).

In some embodiments, the peptide inhibitors comprise D-stereoisomeric amino acids, thereby allowing the formation of immunotherapeutic peptides with increased resistance to protease degradation. In one embodiment, the D-amino acid peptide inhibitors are used for the clinical treatment in platelet-mediated disorders. Although it is not necessary to understand the mechanism of an invention, it is believed that these peptide inhibitors prevent platelet adhesion, aggregation and activation.

In some embodiments, the present invention contemplate peptide inhibitors that are protease resistant. In one embodiment, such protease-resistant peptide inhibitors are peptides comprising protecting groups. For example, a peptide may be protected from exoproteinase degradation by N-terminal acetylation ("Ac") and/or C-terminal amidation.

In some embodiments, the peptide inhibitors comprise conjugated lipids and/or sugars. In other embodiments, the peptide inhibitors comprise hydrophobic amino acid motifs, wherein said motifs are known to increase the membrane penetrating ability of peptides and proteins. Although it is not necessary to understand the mechanism of an invention, it is believed that either lipid/sugar conjugation and/or hydrophobic amino acid motifs increase the efficacy of GPVI-FcRγ collagen receptor complex inhibition using either GPVI Core Peptides and/or Extended Peptides.

In some embodiment, the peptides and compounds contemplated by the present invention may be used for production of peptide/compound-containing cardiovascular stents for local therapy and/or prevention of cardiovascular thrombosis.

III. GPVI Transmembrane Segments

An $Arg^{272}$-$Leu^{272}$ mutation within the GPVI transmembrane domain uncouples the GPVI receptor from the FcRγ protein. This uncoupling results in the concomitant elimination of platelet activation in response to GPVI-FcRγ mediated intracellular signaling in response to collagen. It is reported that this reduced GPVI signaling inhibits platelet activation. Zheng et al., "Expression Of The Platelet Receptor GPVI Confers Signaling Via The Fc Receptor γ-Chain In Response To The Snake Venom Convulxin But Not To Collagen" *J Biol Chem* 276:12999-13006 (2001). Further, an $Arg^{272}$-$Ala^{272}$ mutation within the GPVI transmembrane domain also uncouples the GPVI receptor from the FcRγ protein and might reduce GPVI signaling and inhibit platelet activation. Berlanga et al., "The Fc Receptor g-Chain Is Necessary And Sufficient To Initiate Signaling Through Glycoprotein VI In Transfected Cells By The Snake C-Type Lectin, Convulxin" *Eur J Biochem* 269:2951-2960 (2002). These disclosed mutations are not consistent with the general formula for the presently described GPVI peptide variants.

The construction of fusion proteins comprising a GPVI peptide and an immunoglobulin included truncated and mutated GPVI peptides. The GPVI extracellular domain must be present to retain biological activity ($Glu^{21}$-$Asp^{269}$). These fusion proteins may reduce collagen-induced platelet activation and be useful in the treatment of thrombotic and/or cardiovascular disorders and/or coatings for medical devices. Burger et al., "Glycoprotein VI Fusion Proteins" United States Patent Appln Publ No. 2004/0157300. This disclosed mutation is not consistent with the general formula for the presently described GPVI peptide variants.

The construction of fusion proteins comprising a GPVI peptide and an immunoglobulin, wherein the immunoprotein binds to exposed collagen matrix due to cardiovascular injury, thereby preventing platelet attachment and activation. As part of these fusion proteins, the GPVI extracellular domain must be present and retain biological activity (GPVI residues 1-269). These fusion proteins are suggested to be useful in the treatment of thrombosis and/or atherosclerosis. Massberg et al., "Immunoadhesion Comprising A Glycoprotein VI Domain" US Pat Appln Publ No. 2005/0142140. The reference does not teach mutation sequences in the GPVI peptide transmembrane domain.

An organic molecule inhibitor of Bruton's tyrosine kinase (BTK) participates in the collagen receptor glycoprotein VI (GPVI)-FcRγ coupled signaling pathway. Dibromophenyl-propenamide derivatives are disclosed as effective in inhibiting BTK, thereby inhibiting GPVI-collagen induced platelet activation. Consequently, these inhibitors would be effective in treating medical conditions related to platelet activation and aggregation. Uckun, F. M., "Inhibiting Collagen-Induced Platelet Aggregation" U.S. Pat. No. 6,589,992. The reference does not teach mutation sequences in the GPVI peptide transmembrane domain.

Fragmentary sequences of GPVI-derived peptides were identified by using a specific purification process comprising the extracellular collagen-binding domain but not the GPVI transmembrane core sequence. Tandon et al., "Platelet Membrane Glycoprotein VI (GPVI) DNA And Protein Sequences, And Uses Thereof" U.S. Pat. No. 6,998,469. Consequently, the reference does not teach mutation sequences in the GPVI peptide transmembrane domain.

A. Transmembrane Peptide Variant GPVI-FcRγ Complex Inhibitors

The present invention described herein relates to unknown synthetic peptides and derivatives thereof, which may be useful in the clinical treatment and/or prevention of platelet-mediated disorders.

In one embodiment, the present invention contemplates a peptide derivative having the general formula $R_1$-A-B-C-D-E-F-$R_2$ or a di-sulfide bridged, linear dimer thereof, wherein;

A is absent, Gly, or 1 to 2 hydrophobic uncharged D- or L-amino acid following 1 to 2 non-hydrophobic uncharged and/or negatively charged D- or L-amino acids;

B is a positively charged D- or L-amino acid;

C is absent or 1 to 3 hydrophobic D- or L-amino acids, including D- or L-cysteine or a D- or L-cysteine homologue;

D is, Gly, 1 or 2 non-hydrophobic uncharged and/or positively charged D- or L-amino acids;

E is absent or a peptide comprising 3 to 6 hydrophobic D- or L-amino acids, or a peptide consisting of 3 to 6 highly polar or positively charged D- or L-amino acids, or a peptide consisting of 3 to 6 hydrophobic D- or L-amino acids surrounding a positively charged D- or L-amino acid residue which is spaced 6-9 amino acids from B;

F is absent or 1 or 2 non-hydrophobic D- and L-amino acids;

$R_1$ is absent (i.e., for example, —H) or 1-amino-glucose succinate, 2-aminododecanoate, or myristoylate; and $R_2$ is absent (i.e, for example, —H) or Gly-Tris-monopalmitate, -dipalmitate and -tripalmitate.

In some embodiments, peptide derivatives are created wherein;

A is selected from the group comprising Gly, Asn, Cys, Val, Leu, Ile, and Met;

B is selected from Arg or Lys;

C is selected from the group comprising Ala, Val, Leu, Ile, Met, and Cys;

D is selected from the group comprising Gly, Ser, Thr, Cys, Tyr, Arg and Lys; and F is selected from the group comprising Gly, Ser, Cys, Tyr, and Thr.

In one embodiment, the present invention contemplates a peptide derivative having the general formula $R_1$-[Arg and/or Lys]$_{n=0-4}$-A-B-C-D-E-F-[Arg and/or Lys]$_{n=0-4}$-$R_2$ or a di-sulfide bridged, linear dimer thereof, wherein;

A may be i) absent; ii) 1-2 amino acids selected from the group including, but not limited to, Gln, Ser, Gly, Tyr, Cys, Thr, Asn, Glu, or Asp; or iii) 1-2 amino acids selected from the group including, but not limited to, Pro, Phe, Leu, Ala, Val, Ile, Met, or Trp;

B may be selected from the group including, but not limited to, Arg, Lys, or His;

C may be absent or selected from the group including, but not limited to, Pro, Phe, Leu, Ala, Val, Ile, Met, Trp, or Cys.

D may be 1-2 amino acids selected from the group including, but not limited to, Gln, Ser, Gly, Tyr, Cys, Ile, Asn, Arg, or Lys.

E may be i) absent; ii) 3-6 amino acids selected from the group including, but not limited to, Pro, Phe, Leu, Ala, Val, Ile, Met, or Trp; iii) 3-6 amino acids selected from the group including, but not limited to, Gly, Ser, Thr, Pro, Arg, Lys, or His; or iv) two sets of 1-6 amino acids selected from the group including, but not limited to, Pro, Phe, Leu, Ala, Val, Ile, Met, or Trp, wherein an Arg, Lys, or His may separate the two sets, and wherein the Arg, Lys or His is between 6-9 amino acids from B;

F may be i) absent or ii) 1-2 amino acids selected from the group including, but not limited to, Gln, Ser, Gly, Tyr, Cys, Thr, or Asn.

Figure 11:
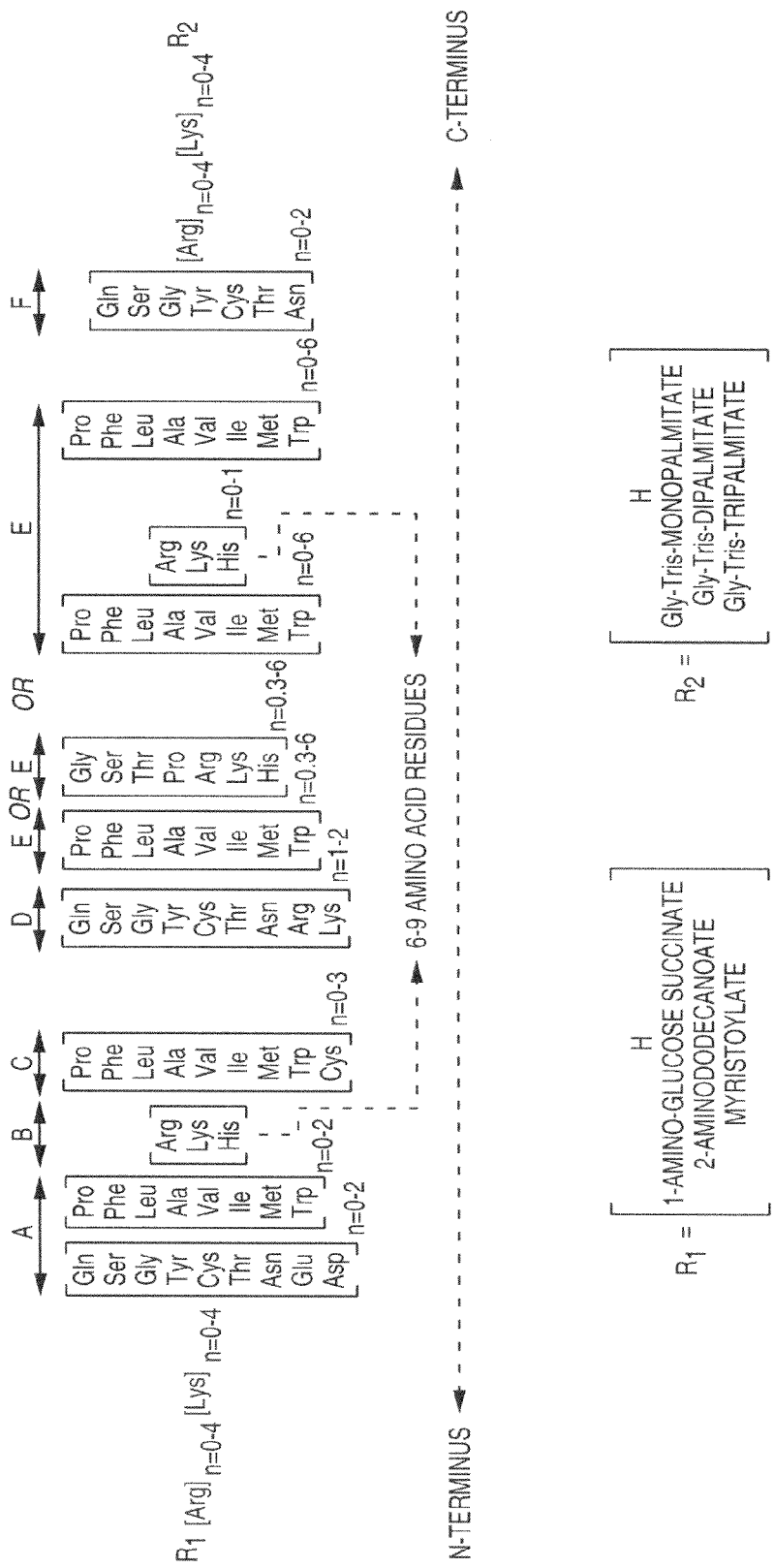
FIG. 11 presents various embodiments of GPVI peptide inhibitor sequences based upon a general formula, wherein in the general formula describes variants of the parent SEQ ID NO:8.

R1 and R2 may be either i) absent; ii) a conjugated lipid selected from the group including, but not limited to, Gly-Tris-monopalmitate, -dipalmitate and -tripalmitate; or iii) a conjugated sugar selected from the group including, but not limited to, 1-amino-glucose succinate, 2-aminododecanoate, or myristoylate. See, FIG. 11.

As referred to herein, hydrophobic amino acids include, but are not limited to, Ala, Val, Leu, Ile, Pro, Phe, Trp, and Met; positively charged amino acids include, but are not limited to, Lys, Arg and His; and negatively charged amino acids include, but are not limited to, Asp and Glu.

The above general formula represents one embodiment of a GPVI transmembrane segment comprising at least one conserved domain that contains highly homologous sequences between species. In one embodiment, a GPVI transmembrane segment comprises GNLVRICLGA (Gly-Asn-Lys-Val-Arg-Ile-Cys-Lys-Gly-Ala; human amino acid residues 268-277; Accession No. Q9HCN6; SEQ ID NO:32) along with various lipid and/or sugar derivatives that may, or may not, have a disulfide bridged dimer. In another embodiment, a GPVI transmembrane segment comprises VVAGRCCISS-LLLKKKPP (SEQ ID NO:33), wherein said sequence meets the criteria for the above outlined general formula.

In one embodiment, the present invention contemplates a method of rational designing of the peptides and lipid- and/or sugar-conjugated peptides consisting of L- or D-stereoisomeric amino acids in order to increase effectiveness of the peptides in inhibiting the function of a GPVI-FcRγ receptor complex. In one embodiment, the method comprises substituting at least one amino acid of a GPVI transmembrane core peptide (i.e., for example, and arginine or a lysine into at least one alpha-helix of the Peptide Core and/or Extended Peptide), thereby increasing binding to the transmembrane domain of FcRγ chain. See, FIGS. 4A-C.

In another embodiment, the method comprises conjugating at least one lipid and/or at least one sugar to the C- and/or N-termini of the peptide, thereby increasing binding to the transmembrane domain of the FcRγ chain and/or improving the penetration of the peptide variant into the platelet membrane. In one embodiment, the lipid- and/or sugar-conjugated peptide variants comprise D-amino acids, thereby increasing resistance to protease degradation. In one embodiment, a protease resistant peptide variant is useful clinically for inhibiting platelet adhesion, aggregation and activation in platelet-mediated disorders.

In some embodiments, conjugated peptide variants are synthesized using the standard procedures. Amon et al., "Lipidation and Glycosylation of a T-cell Antigen Receptor (TCR) Transmembrane Hydrophobic Peptide Dramatically Enhances in vitro and in vivo Function" *BBA Molecular Cell Research.* 1763:879-888 (2006); Whittaker et al., "A gentle method for linking Tris to amino acids and peptides" *Peptide Research* 6: 125-128 (1993); In: *Chemistry of Peptide Synthesis*, N. Leo Benoiton (ed.), CRC, (2005); Gerber et al., "D-enantiomer peptide of the TCR-alpha transmembrane domain inhibits T-cell activation in vitro and in vivo" *FASEB Journal (FJ Express)* 19:1190-1192 (2005); Kliger et al., "Fusion peptides derived from the HIV type I glycoprotein 41 associate with Mn phospholipid membranes and inhibit cell-cell fusion. Structure-function study" *J. Biol. Chem.* 272: 13496-13505 (1997); and Merrifield et al., "Synthesis of the antibacterial peptide cecropin A (1-33)" *Biochemistry* 21:5020-5031 (1982).

In one embodiment, the rational design method comprises inserting at least one polyarginine and/or polylysine sequence into a GPVI transmembrane sequence, thereby increasing binding to a transmembrane domain of an FcRγ chain and/or improving the penetration of the peptide variant into the platelet membrane. Other modifications of the peptides contemplated herein include, but are not limited to, modifications to side chains, incorporation of unnatural amino acids and/or their derivatives during peptide synthesis and the use of crosslinkers and other methods which impose conformational constraints on the peptides. It may also be possible to add various groups to the peptide of the present invention to confer advantages such as increased potency or extended half life in vivo without substantially decreasing the biological activity of the peptide. It is intended that such modifications to the peptide of the present invention which do not result in a decrease in biological activity are within the scope of the present invention.

Any combination of the above embodiments may be used together in order to increase effectiveness of the peptide variants to inhibit the function of a GPVI-FcRγ receptor complex. The most effective inhibitory peptides and derivatives thereof may be identified by typical screening assay procedures for evaluation of inhibition of platelet adhesion, aggregation and activation. In: *Platelets*, Alan D. Michelson (ed.) Academic Press, (2002).

B. Peptide-Based Inhibitors

Although it is not necessary to understand the mechanism of an invention, it is believed that inhibition of a platelet collagen receptor (i.e., for example, GPVI-FcRγ) signaling can be achieved by binding of a peptide-based inhibitor to the transmembrane (TM) domain of the FcRγ chain, thus substituting the GPVI subunit and abolishing the interaction between the TM domains of the GPVI and FcRγ chains. One possible result is the inhibition of GPVI-mediated transmembrane signaling because collagen binding to the extracellular domain of a GPVI collagen recognition subunit does not lead to FcRγ signaling subunit clustering (i.e., for example, oligomerization). It is further believed that this clustering induces the phosphorylation of tyrosine residues in the intracellular FcRγ domain and initiates downstream signaling.

The TM domains of GPVI and FcRγ subunits comprise hydrophobic sequences that may adopt a stable alpha-helical structure within a platelet plasma membrane lipid bilayer. It is hypothesized that electrostatic interactions between these TM domains maintain the integrity of the platelet collagen receptor GPVI-FcRγ complex and are provided by the interaction between positively charged Arg residue of the GPVI TM domain and two negatively charged Asp residues of the TM domains of the FcRγ dimer.

It might be suggested that, theoretically, the simplest and the most selective and effective peptide inhibitor would be a synthetic peptide corresponding to the TM domain of GPVI subunit. However, as several embodiments of the present invention contemplate, peptide inhibitor sequence, alone, is not the only relevant consideration. In one embodiment, a peptide inhibitor targeted to the transmembrane interactions should be optimized for cell membrane binding. In one embodiment, a peptide inhibitor should be optimized for membrane insertion, thereby attaining a close spatial proximity and/or proper orientation to an interacting partner (i.e., for example, a TM domain of an FcRγ dimer). In one embodiment, a peptide inhibitor should be optimized for binding effectiveness to an interacting partner.

Although it is not necessary to understand the mechanism of an invention, it is believed that a peptide inhibitor comprising the wild type TM domain of GPVI is not optimized for each of the above three factors. Other embodiments, however, are contemplated by the present invention by using extracellularly administered synthetic peptides which are optimized for at least one of the above three considerations. Thus, the 30-60% inhibition of platelet activation observed for the GPVI core peptide (Examples 4 and 5) can be significantly improved in terms of efficiency by rational design of the peptide-based inhibitors. For example, the inhibition activity the T cell antigen receptor core peptide has been reported to increase from 30 to 80% by lipidation of the relevant peptide inhibitors.

In summary, the present invention contemplates optimizing the effectiveness and selectivity of peptide inhibitors for GPVI-FcRγ-mediated signaling, by adhering to at least one of these guidelines:

1) ability to effectively bind to the platelet plasma membrane and insert into the membrane (i.e., for example, increasing hydrophobicity);
2) ability to adopt helical conformation upon membrane binding and penetration (i.e., for example, increasing intrinsic helicity);
3) ability to selectively and effectively bind to the TM domain of the FcRγ subunit, thus effectively competing with the GPVI subunit for the binding to the FcRγ subunit (i.e., for example, by increasing stable α-helixes).

These guidelines were used to develop a method of rational designing of the peptides in order to increase effectiveness of the peptides in inhibition of function of the GPVI-FcRγ receptor complex.

1. Hydrophobicity

The hydrophobicity (or lipophilicity) of peptides and peptide analogues may be increased by i) inserting hydrophobic regions; ii) improving the ability of a peptide-based inhibitors to bind the membrane; and/or iii) improving the ability of a peptide-based inhibitor to insert into a membrane. In one embodiment, hydrophobic regions may be inserted into a peptide inhibitor sequence by using lipophilic groups including, but not limited to, myristoylate-, 1-amino-glucose succinate, 2-aminododecanoate, or Gly-Tris-palmitate, -dipalmitate or -tripalmitate, coupled to the N- and/or C-termini of a peptide. In one embodiment, the membrane binding/insertion ability of a peptide inhibitor may be improved by using highly positively charged poly-Lys or poly-Arg sequences coupled to an N- and/or C-terminus. A general formula summarizing many suggested inhibitory peptides and/or compositions is presented that incorporates both approaches that are expected to increase the effectiveness of the peptides to inhibit the function of a GPVI-FcRγ receptor complex. See, FIG. 11.

Lipid-binding activity of the test peptide-based inhibitors can be predicted using ProtParam® software (us.expasy.org/tools/protparam.html) and experimentally evaluated by different techniques such as, for example, surface plasmon resonance (SPR) or sucrose-loaded vesicle binding assay. Based on the obtained results, a peptide-based inhibitor with optimal membrane-binding activity can be chosen. For example, 'Grand Average Of Hydropathy' (GRAVY) scores for peptides can be obtained using ProtParam®, in which a score $>-0.4$ (=mean score for cytosolic proteins) indicates the probability for membrane association (i.e., for example, the higher the score, the greater the probability for membrane association).

2. Helicity

As discussed above, the primary sequence of the parent inhibitory peptide, the GPVI core peptide, can be modified to improve the ability of various peptide-based inhibitors contemplated herein to adopt helical conformation upon membrane binding and penetration. See, FIG. 11. Overall protein folding may be specified by hydrophobic-polar residue patterning, whereas the bundle oligomerization state, detailed main-chain conformation, and interior side-chain rotamers may be engineered by computational enumerations of packing in alternate backbone structures. Main-chain flexibility is incorporated through an algebraic parameterization of the backbone. Harbury et al., "High-resolution protein design with backbone freedom" *Science* 282:1462-1467 (1998).

Peptide helicity of the designed primary sequences of various peptide-based inhibitors contemplated herein can be first evaluated computationally using secondary structure prediction programs. (i.e., for example, Expasy Proteomics Tools; expasy.org/tools). The most promising inhibitors can be measured experimentally for intrinsic and/or induced helicity using circular dichroism (CD) spectroscopy. Circular dicroism spectroscopy is used to analyze the secondary structure of a protein and/or peptide. Specifically, CD spectroscopy measures differences in the absorption of left-handed polarized light versus right-handed polarized light which arise due to structural asymmetry. The absence of regular structure results in zero CD intensity, while an ordered structure results in a spectrum which can contain both positive and negative signals. α-helix, β-sheet, and random coil structures each give rise to a characteristic shape and magnitude of CD spectrum. The approximate fraction of each secondary structure type that is present in any peptide or protein can thus be determined by analyzing its far-UV CD spectrum as a sum of fractional multiples of such reference spectra for each structural type. Like all spectroscopic techniques, the CD signal reflects an average of the entire molecular population. Thus, while CD can determine that a peptide or protein contains about 50% α-helix, it cannot determine which specific residues are involved in the α-helical portion. Based on the obtained results, a peptide-based inhibitor optimized with the predicted and/or observed, intrinsic and/or induced optimal helicity can be chosen.

Alternatively, secondary structure prediction programs may be used to accurately predict the peptide helicity based on primary sequence of the computationally designed peptide-based inhibitors. A few of the available programs include, but are not limited to:

a. AGADIR—An algorithm to predict the helical content of peptides
 b. APSSP—Advanced Protein Secondary Structure Prediction Server
 c. GOR—Garnier et al, 1996
 d. HNN—Hierarchical Neural Network method (Guermeur, 1997)
 e. Jpred—A consensus method for protein secondary structure prediction at University of Dundee
 f. JUFO—Protein secondary structure prediction from sequence (neural network)
 g. nnPredict—University of California at San Francisco (UCSF)
 h. Porter—University College Dublin
 i. PredictProtein—PHDsec, PHDacc, PHDhtm, PHDtopology, PHDthreader, MaxHom, EvalSec from Columbia University
 j. Prof—Cascaded Multiple Classifiers for Secondary Structure Prediction
 k. PSA—BioMolecular Engineering Research Center (BMERC)/Boston
 l. PSIpred—Various protein structure prediction methods at Brunel University
 m. SOPMA—Geourjon and Deleage, 1995
 n. SSpro—Secondary structure prediction using bidirectional recurrent neural networks at University of California
 o. DLP—Domain linker prediction at RIKEN 3. α-Helix Stability Although it is not necessary to understand the mechanism of an invention, it is believed that the TM domains of the GPVI and the FcRγ subunits represent stable alpha-helixes and, thus, the interactions can be presented using helix-wheel diagrams. See, FIG. 3A. These diagrams are based on the primary peptide/protein sequence and can be created using commercially and publicly available programs (i.e., including, but not limited to, Antheprot v.6.0; antheprotpbil.ibcp.fr; or Helical Wheel Custom Images and Interactive Java Applets; cti.itc.virginia.edu/~cmg/Demo/wheel/wheelApp.html and http://kael.net/helical.htm). These diagrams can be used for evaluation of close proximity and/or proper orientation of positively charged amino acid residue(s) of the peptide or peptide analogue of interest towards an interacting partner (i.e., for example, negatively charged TM residues of a FcRγ dimer).

Figure 3A:
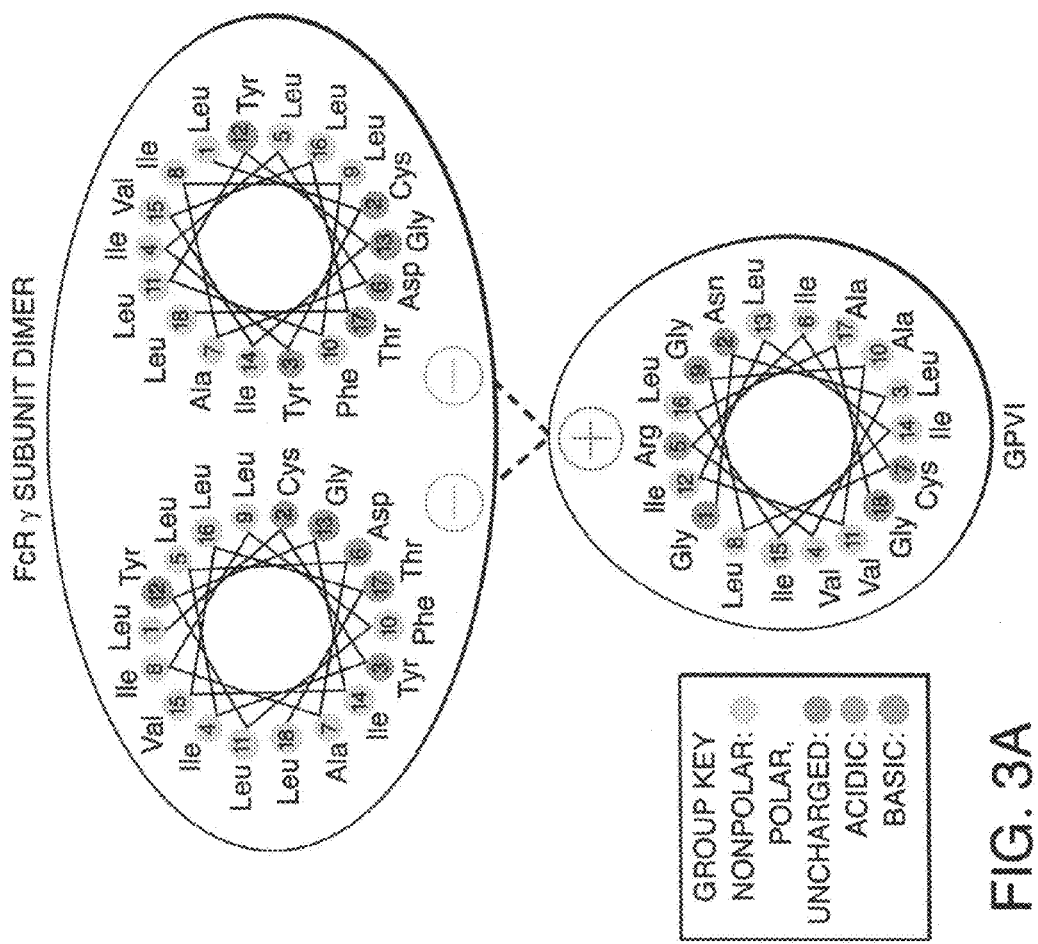
FIG. 3A illustrates one embodiment of normal interactions between a GPVI subunit and a FcRγ subunit to form a functional collagen receptor.
Figure 3A:
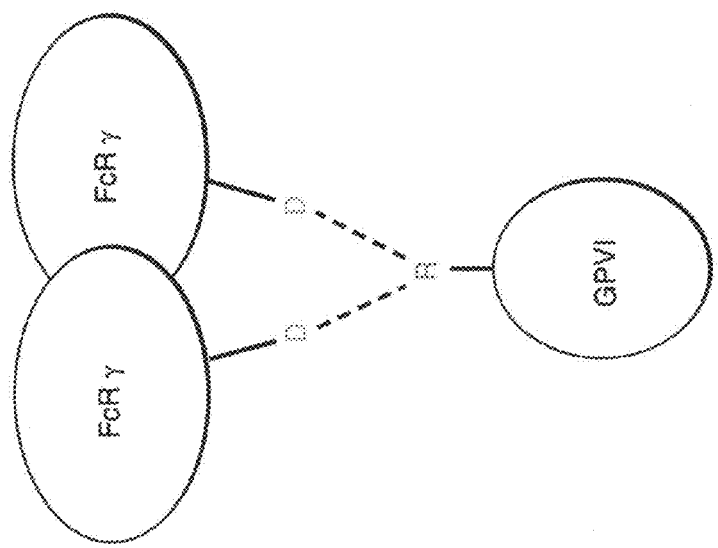
Figure 3B:
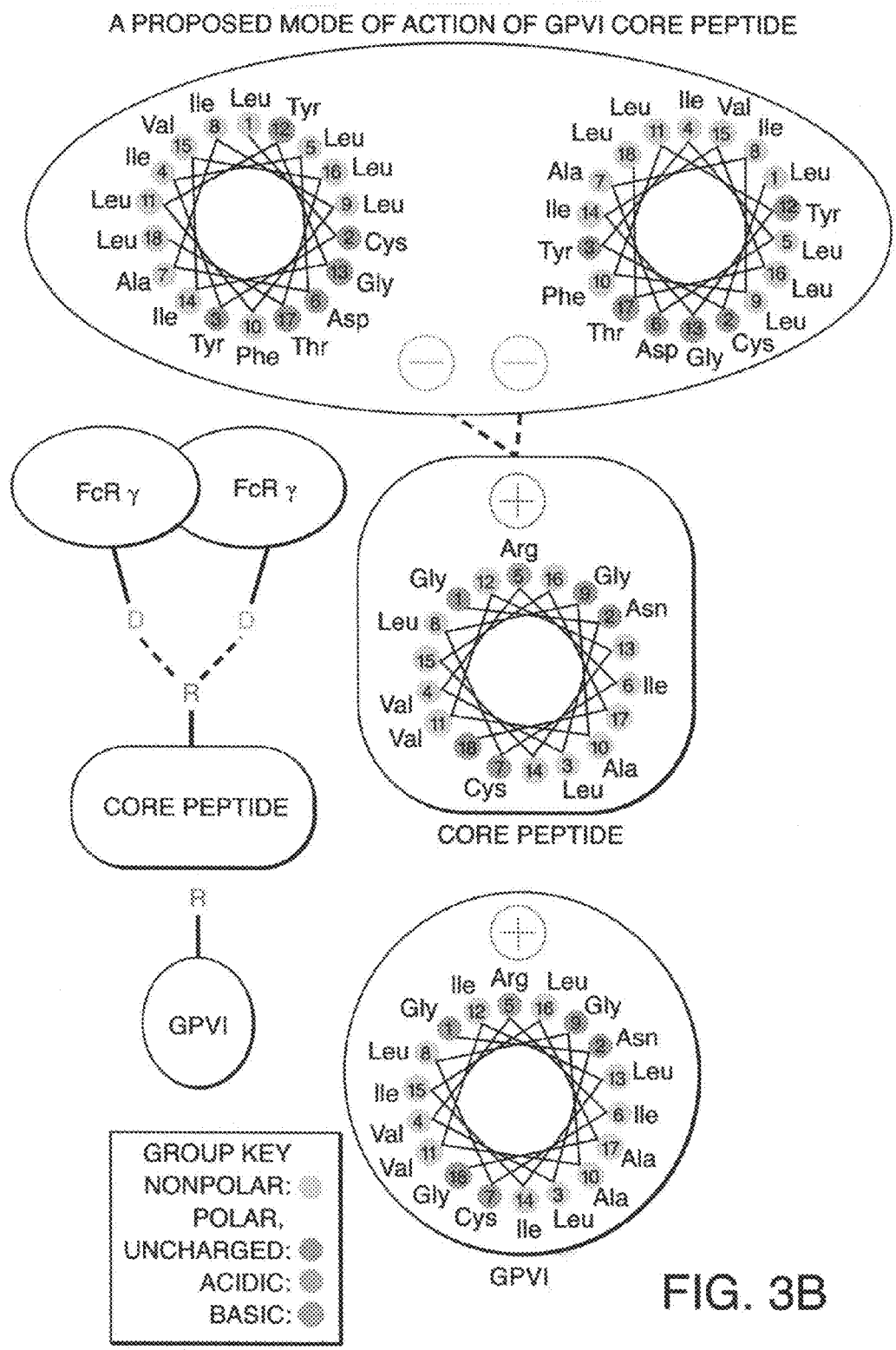
FIG. 3B illustrates one embodiment of disrupted interactions between a GPVI subunit and a FcRγ subunit resulting in a non-functional collagen receptor.
Figure 4A:
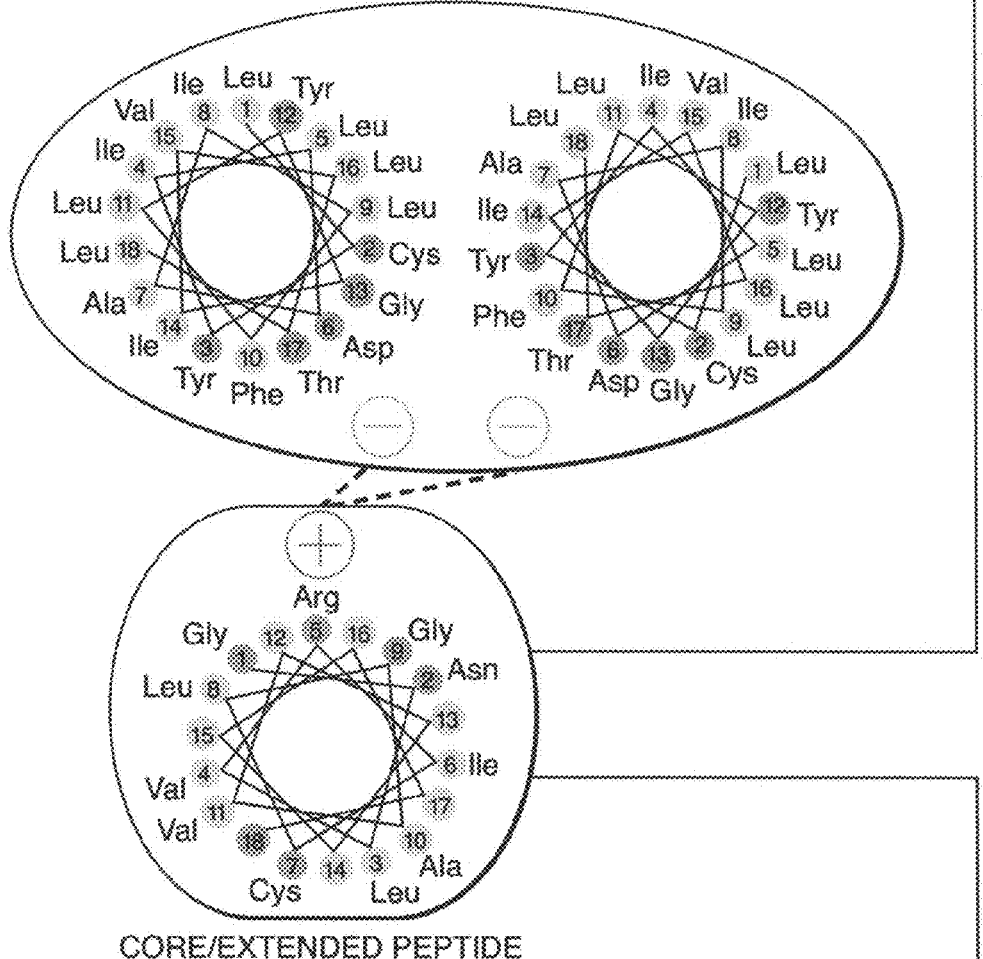
FIGS. 4A, 4B, and 4C illustrate one embodiment of modulation of binding of the GPVI Core and/or Extended peptides to the transmembrane domain of the FcRγ subunit dimer.
Figure 4B:
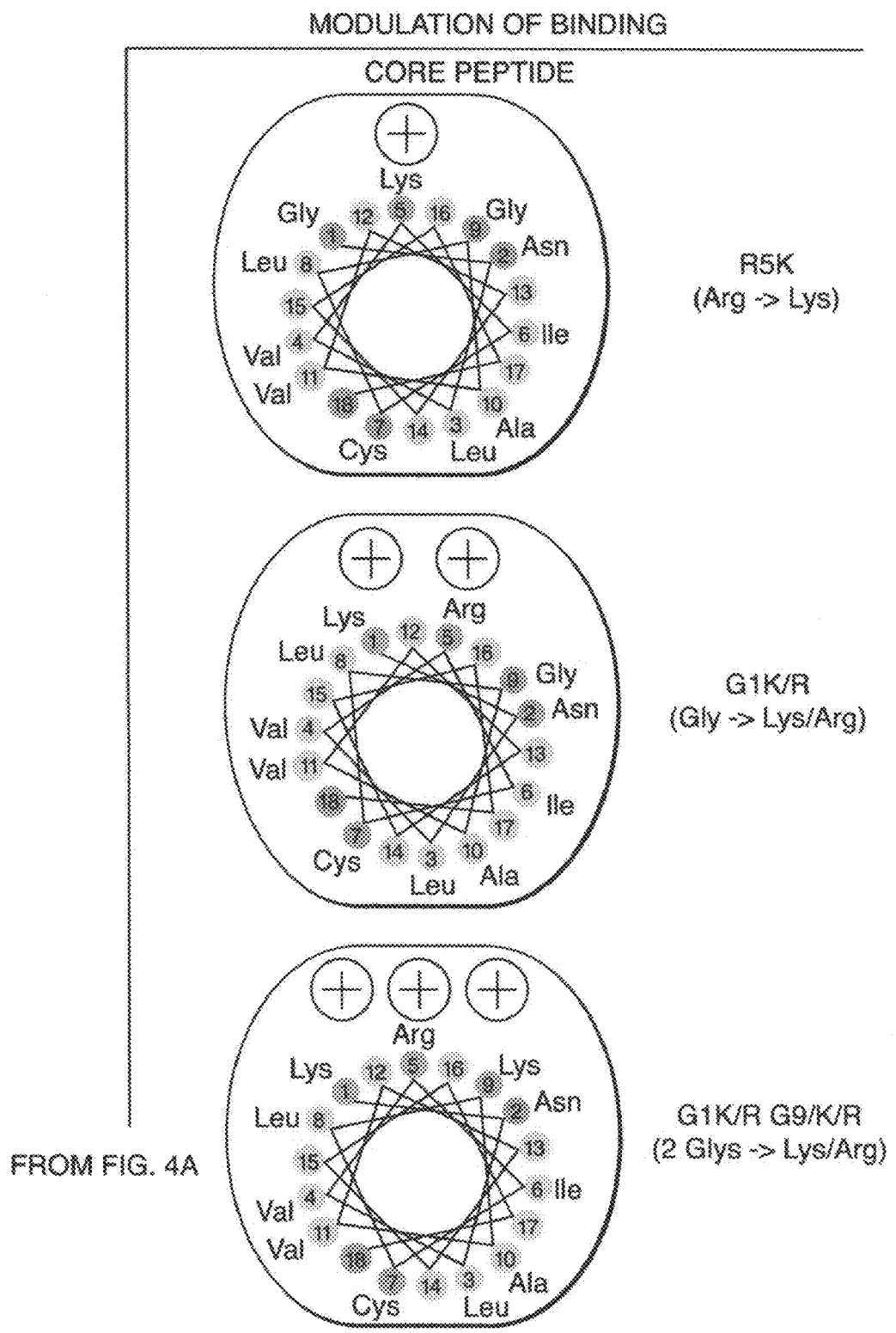
Figure 4C:
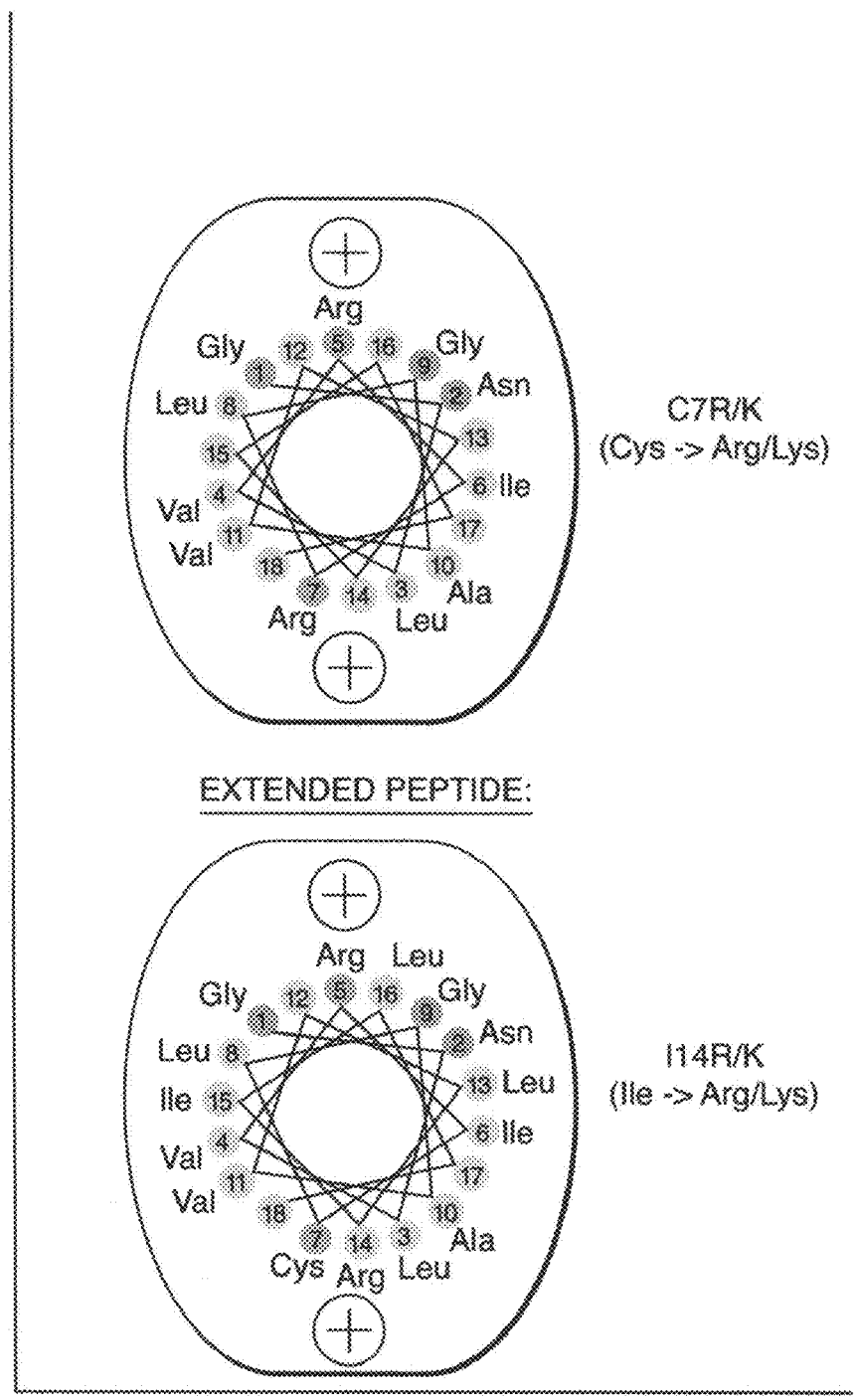

As shown in the FIG. 3A, the electrostatic interaction between the GPVI TM positively charged arginine (R, blue) and the negatively charged aspartic acid pair (D, pink) in the FcRγ dimer stabilize the association of these respective subunits, thereby playing a role in collagen-induced GPVI-mediated platelet activation and aggregation. Some embodiments of peptide-based inhibitors contemplated by the present invention aim to interrupt this interaction and replace the GPVI subunit of the GPVI- FcRγ receptor complex. In one embodiment, peptide-based inhibitors can be computationally designed to increase their competitiveness with the GPVI subunit. In one embodiment, competitiveness may be increased by using a conservative amino acid substitution of arginine for lysine. In another embodiment, competitiveness may be increased by inserting a positively charged amino acid residue (i.e., for example, arginine and/or lysine). In one embodiment, the insertion and/or substitution is located within an alpha-helix of the peptide-based inhibitors (i.e., for example, a GPVI core or Extended Peptides; FIGS. 4A-C), thereby increasing the binding activity to transmembrane domains of the FcRγ signaling subunit dimer and enhancing the effectiveness of the peptides to inhibit the function of the a GPVI-FcRγ receptor complex.

4. Peptide-Based Inhibitor Sequence Listings

A list of the sequences of the peptides and peptide analogues shown below includes, but is not limited to, peptide-based inhibitors predicted to be effective in inhibiting the PGVI-FcRγ signaling mechanism. See, Table 2.

Accordingly, it is intended that the present invention includes within its scope peptides which include additional amino acids to the "core" sequence of the peptide of the present invention and which affect the transmembrane interactions between the GPVI subunit and FcRγ dimer

TABLE 2

Exemplary Peptide-Based GPVI-FcRγ Complex Inhibitor Sequences

| ## | R1[a] | Sequence (the "core" sequence of the peptide of the present invention is underlined) | R2[b] | % helicity[c] A | % helicity[c] H | GRAVY score[d] | Helix Wheel[e] |
|---|---|---|---|---|---|---|---|
| 1 | — | <u>GNLVRICLGAVILIILAGFLA</u> (GPVI TM peptide) (SEQ ID NO: 8) | — | 13 | 48 | 2.233 | + |
| 2 | — | <u>GNLVRICLGAV</u> (GPVI TM core peptide) (SEQ ID NO: 9) | — | 1 | 0 | 1.455 | + |
| 3 | — | <u>GNLVRICLRAVILIILAGFLA</u> (SEQ ID NO: 10) | — | 23 | 57 | 2.038 | ++ |
| 4 | — | <u>GNLVRIGLRAVILIILAGFLA</u> (SEQ ID NO: 11) | — | 22 | 52 | 1.900 | ++ |
| 5 | — | <u>GNLVRIGLRAVILIILAGFLA</u> (SEQ ID NO: 11) | + | 22 | 52 | (1.900) | ++ |
| 6 | — | <u>GNLVRICLRAVRLIILAGFLA</u> (SEQ ID NO: 12) | — | 9 | 67 | 1.610 | +++ |
| 7 | LA | <u>GNLVRICLRAVRLIILAGFLA</u> (SEQ ID NO: 12) | — | 9 | 67 | (1.610) | +++ |
| 8 | — | RRKK<u>YARALLYGLRAVGY</u>RKK (SEQ ID NO: 13) | — | 2 | 62 | -1.038 | +++ |
| 9 | Myr | GRRKK<u>YARALLYGLRAVGY</u>RKK (SEQ ID NO: 14) | — | 2 | 64 | (-1.009) | +++ |
| 10 | — | KKR<u>GLVKILLRILRVLLPGKR</u> (SEQ ID NO: 15) | — | 23 | 71 | 0.200 | +++ |
| 11 | Myr | GKKR<u>GLVKILLRILRVLLPGKR</u> (SEQ ID NO: 16) | — | 23 | 68 | (0.173) | +++ |
| 12 | — | KKR<u>GLVKILLRILRVLLPGKR</u> (SEQ ID NO: 15) | + | 23 | 71 | (0.200) | +++ |
| 13 | LA | KKR<u>GLVKILLRILRVLLPGKR</u> (SEQ ID NO: 15) | — | 23 | 71 | (0.200) | +++ |
| 14 | — | <u>CGLVRIILGAVIGILIIL</u>KKK (SEQ ID NO: 17) | — | 8 | 76 | 1.786 | + |
| 15 | — | (<u>CGLVRIILGAVIGILIIL</u>KKK)₂[f] (SEQ ID NO: 18) | — | 8 | 76 | 1.786 | (++) |
| 16 | — | RK<u>CGLVRIILGAVRGILIILC</u>KKK (SEQ ID NO: 19) | — | 6 | 71 | 0.942 | ++ |
| 17 | LA | RK<u>CGLVRIILGAVRGILIILC</u>KKK (SEQ ID NO: 19) | — | 6 | 71 | (0.942) | ++ |
| 18 | — | RK<u>CGLVRIILGAVRGILIILC</u>KKK (SEQ ID NO: 19) | + | 6 | 71 | (0.942) | ++ |
| 19 | — | (RK<u>CGLVRIILGAVRGILIILC</u>KKK)₂[g] (SEQ ID NO: 20) | — | 6 | 71 | 0.942 | (++++) |
| 20 | — | <u>YTILRFILGLAKVALI</u> (SEQ ID NO: 21) | — | 2 | 75 | 1.781 | ++ |
| 21 | — | KRK<u>YTILRFILGLAKVALI</u>KR (SEQ ID NO: 22) | — | 5 | 81 | 0.371 | ++ |
| 22 | LA | KRK<u>YTILRFILGLAKVALI</u>KR (SEQ ID NO: 22) | — | 5 | 81 | (0.371) | ++ |
| 23 | — | KRK<u>YTILRFILGLAKVALI</u>KR (SEQ ID NO: 22) | + | 5 | 81 | (0.371) | ++ |
| 24 | Myr | GKRK<u>YTILRFILGLAKVALI</u>KR (SEQ ID NO: 23) | — | 5 | 77 | (0.336) | ++ |

TABLE 2-continued

Exemplary Peptide-Based GPVI-FcRγ Complex Inhibitor Sequences

| ## | R1[a] | Sequence (the "core" sequence of the peptide of the present invention is underlined) | R2[b] | % helicity[c] A | % helicity[c] H | GRAVY score[d] | Helix Wheel[e] |
|---|---|---|---|---|---|---|---|
| 25 | — | GNLVRICLGAVILIILAGFLA (parent) (SEQ ID NO: 8) | + | 13 | 48 | (2.233) | + |
| 26 | Myr | GNLVRICLGAVILIILAGFLA (parent) (SEQ ID NO: 8) | − | 13 | 48 | (2.233) | + |
| 27 | LA | GNLVRICLGAVILIILAGFLA (parent) (SEQ ID NO: 8) | − | 13 | 48 | (2.233) | + |
| 28 | — | GNLVRILARAILILIKILAG (SEQ ID NO: 24) | − | 50 | 80 | 1.695 | +++ |
| 29 | — | GNLVRILARAILILIKILAG (SEQ ID NO: 24) | + | 50 | 80 | (1.695) | +++ |
| 30 | LA | GNLVRILARAILILIKILAG (SEQ ID NO: 24) | − | 50 | 80 | (1.695) | +++ |
| 31 | — | KKGNLVRILARAILILIKILAGKK (SEQ ID NO: 25) | − | 67 | 75 | 0.762 | +++ |
| 32 | — | KKGNLVRILARAILILIKILAGKK (SEQ ID NO: 25) | + | 67 | 75 | (0.762) | +++ |
| 33 | LA | KKGNLVRILARAILILIKILAGKK (SEQ ID NO: 25) | − | 67 | 75 | (0.762) | +++ |
| 34 | — | YEALKILRRILRVILAGG (SEQ ID NO: 26) | − | 21 | 78 | 0.750 | ++++ |
| 35 | LA | YEALKILRRILRVILAGG (SEQ ID NO: 26) | − | 21 | 78 | (0.750) | ++++ |
| 36 | — | YEALKILRRILRVILAGG (SEQ ID NO: 26) | + | 21 | 78 | (0.750) | ++++ |
| 37 | — | YEALRILRRILRVILAGG (SEQ ID NO: 26) | − | 26 | 78 | 0.717 | ++++ |
| 38 | LA | YEALRILRRILRVILAGG (SEQ ID NO: 26) | − | 26 | 78 | (0.717) | ++++ |
| 39 | — | NALRAVAGAALAAVAAG (SEQ ID NO: 27) | − | 2 | 82 | 1.376 | + |
| 40 | — | NALRAVAGAALAAVAAGKKK (SEQ ID NO: 28) | − | 5 | 80 | 0.585 | + |

[a]N-terminal group: LA, lipoamino acid, 2-aminododecanoate; Myr, myristoylate.
[b]C-terminal group: Gly-Tris-tripalmitate.
[c]Peptide helicity is calculated in % using secondary structure prediction programs AGADIR (A) and HNN (H) available on the Expasy Proteomics Tools website (www.expasy.org/tools).
[d]Peptides grand average hydropathicity (GRAVY) score is calculated using the Web-available ProtParam program (www.expasy.org/tools/protparam.html). Each amino acid is assigned a hydropathy index, a value reflecting its relative hydrophilicity and hydrophobicity. The sum of the hydropathy indices of a given sequence divided by the number of residues in the sequence generates the GRAVY score. The higher the score the greater is the probability for membrane association. For lipidated peptides, the GRAVY score is indicated only for the peptide sequence.
[e]Helix Wheel is plotted using the Helical Wheel Custom Images and Interactive Java Applet (cti.itc.virginia.edu/~cmg/Demo/wheel/wheelApp.html) to evaluate proximity and/or orientation of positively charged amino acid residue(s) of the peptide or peptide analogue of interest towards its(their) interacting partner-negatively charged TM residues of the FcRγ dimer. "+" means one positively charged amino acid residue in close proximity and orientation towards TM Asp residues of FcRγ dimer, "++" means two residues, etc.
[f]Disulfide-linked dimer.
[g]Disulfide-linked cyclic dimer.

5. Core Peptide Variant Consensus Sequences

Based upon the specific sequences contemplated in Table 2, the following consensus sequences may be constructed:

SEQ ID NO: 1: G-N-L-V-R-I-$X_1$-$X_2$-$X_3$-A-$X_4$-$X_5$-$X_6$-$X_7$-I, wherein $X_1$ consists of C, L or G; $X_2$ consists of A; $X_3$ consists of G or R; $X_4$ consists of V or I: and $X_5$ consists of I, L or R: $X_6$ consists of I or L; and $X_7$ consists of I or L.

SEQ ID NO:2: $X_1$-$X_2$-$X_3$-$X_4$-$X_5$-Y-A-R-A-L-L-Y-G-L-R-A-V-G-Y-$X_6$-$X_7$-$X_8$, wherein $X_1$ consists of G or nothing; and $X_2$, $X_3$, $X_4$, $X_5$, $X_6$, $X_7$, and $X_8$ consist of K, R, or nothing.

SEQ ID NO:3: $X_1$-$X_2$-$X_3$-$X_4$-G-L-V-K-I-L-L-R-I-L-R-V-L-L-P-G-$X_5$-$X_6$, wherein $X_1$ consists of G or nothing; and $X_2$, $X_3$, $X_4$, $X_5$, and $X_6$ consist of K, R, or nothing.

SEQ ID NO:4: $X_1$-$X_2$-C-G-L-V-R-I-I-L-G-A-V-$X_3$-G-I-L-I-I-L-C-$X_4$-$X_5$-$X_6$, wherein $X_1$ and $X_2$ consist of K, R, or nothing; $X_3$ consists of I or R; and $X_4$, $X_5$, and $X_6$ consist of K, R, or nothing.

SEQ ID NO:5: $X_1$-$X_2$-$X_3$-$X_4$-Y-T-I-L-R-F-I-L-G-L-A-K-V-A-L-I-$X_5$-$X_6$, wherein $X_1$ consists of G or nothing; and $X_2$, $X_3$, $X_4$, $X_5$ and $X_6$ consist of K, R, or nothing.

SEQ ID NO:6: Y-E-A-L-$X_1$-I-L-R-R-I-L-R-V-I-L-A-G-G, wherein $X_1$ consist of K or R.

SEQ ID NO:7: N-A-L-R-A-V-A-G-A-A-L-A-A-V-A-A-G-$X_1$-$X_2$-$X_3$, wherein $X_1$, $X_2$, or $X_3$ may consist of K or nothing.

IV. Therapeutic Applications of GPVI-FcRγ Peptide Inhibitors

The invention further provides clinically therapeutic methods of intervening and modulating GPVI function comprising using an agent selected from the group of agents or compositions that block/inhibit/prevent/disrupt interaction of GPVI and FcRγ subunits of the GPVI-FcRγ signaling complex.

1. Targeting MIRRs in Human Disease

Protein-protein interactions constitute the foundation of most cell recognition and signal-transduction processes in health and disease. Thus, specific inhibition and/or modulation of these interactions provides a promising novel approach for rational drug design, as revealed by recent progress in the design of inhibitory antibodies, peptides and small molecules [28].

a. Transmembrane Interactions Between Recognition and Signaling Subunits

Figure 9A:
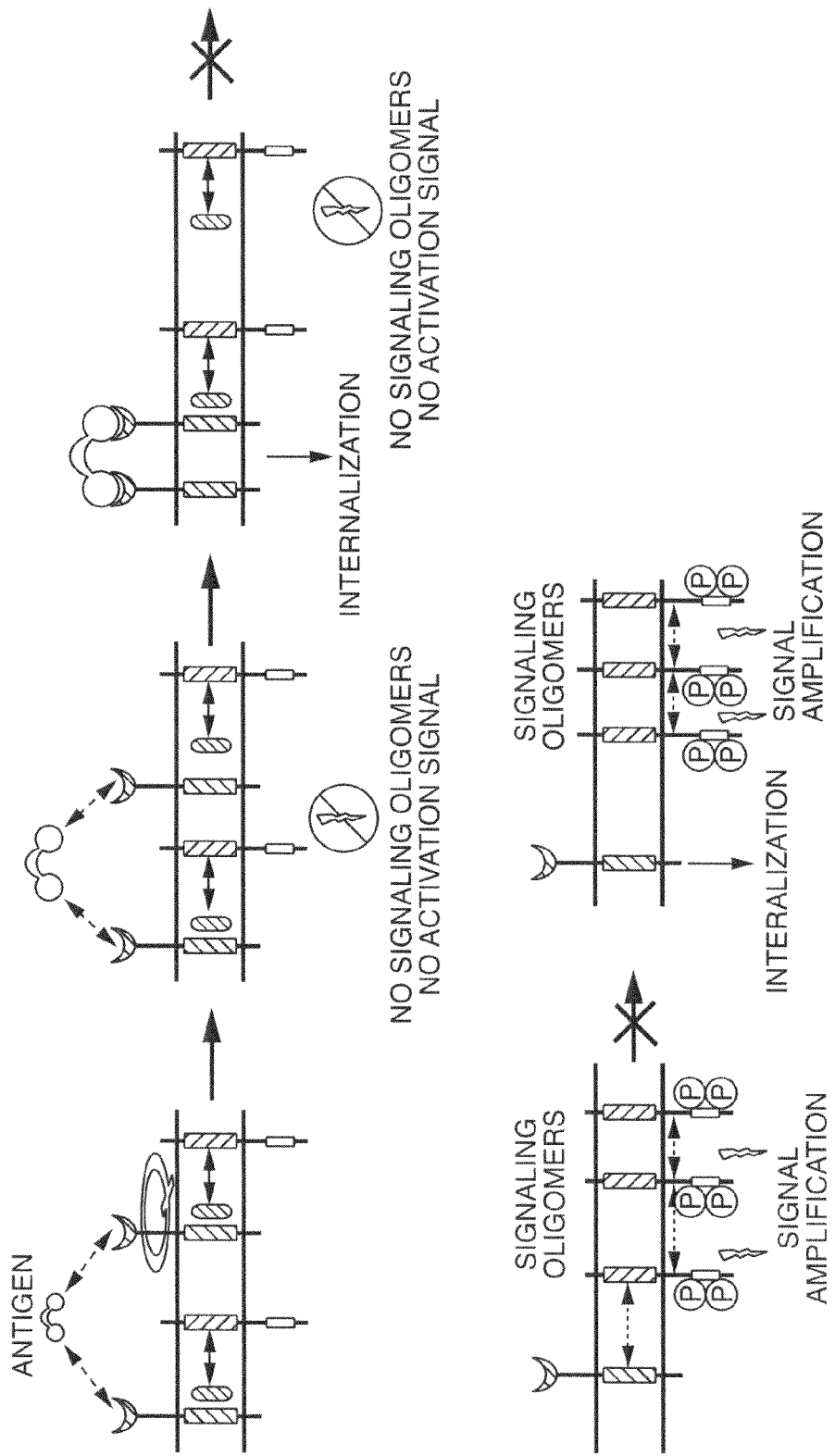
FIGS. 9A and 9B present one embodiment wherein a specific blockade of transmembrane interactions by an antigen between recognition and signaling subunits results in 'pre-dissociation' of the receptor complex representing a first point of intervention (i.e., Target 1), thereby preventing the formation of signaling oligomers and inhibiting antigen-dependent immune cell activation. By contrast, antibody crosslinking of the 'pre-dissociated' MIRRs do not affect receptor triggering and cell activation.
Figure 9B:
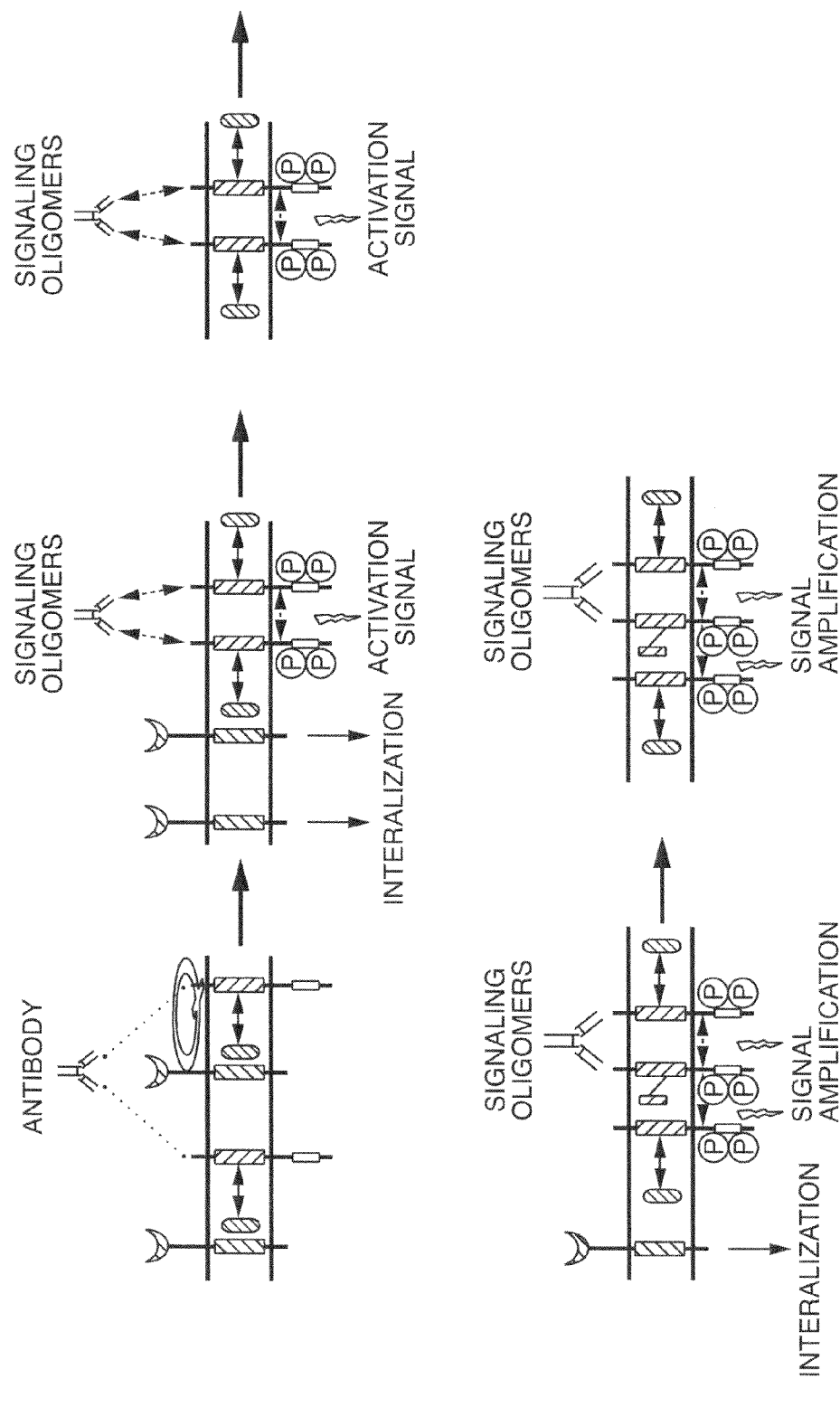

A specific blockade or disruption of the transmembrane interactions between MIRR recognition and signaling subunits may cause a physical and functional disconnection of the subunits in accordance with the SCHOOL model (Target 1). Antigen stimulation of these 'pre-dissociated' receptors leads to clustering of recognition subunits, but not signaling subunits. As a result, signaling oligomers are not formed, thereby preventing the phosphorlyation of ITAM Tyr residues and the initiation of the signaling cascade. FIGS. 9A and 9B. By contrast, this 'pre-dissociation' does not prevent the formation of signaling oligomers when signaling subunits are clustered by specific antibodies (e.g., anti-CD3 antibodies for TCRs, and anti-Igβ antibodies for B-cell receptors) that trigger cell activation. For this reason, these signaling-subunit-specific antibodies might be used in future therapeutic strategies to compensate for the immunosuppressive action of transmembrane targeted inhibitory agents.

Although it is not necessary to understand the mechanism of an invention, it is believed that the MIRR structure enables not only the blockade or disruption of the specific transmembrane interactions between receptor recognition and signaling subunits but also their modulation using a sequence-based approach. A strengthening, weakening, or selective disruption of the association between particular recognition and signaling subunits might enable modulation of the ligand-induced cell response. In addition, the ability to 'disconnect' particular signaling subunits selectively might provide a powerful tool with which to study MIRR functions. In one embodiment, the present invention contemplates a method of pharmacological intervention comprising modulating transmembrane interactions between recognition and signaling subunits.

For example, a T-cell receptor (TCR) core peptide (CP) is believed to comprise immunosuppressive action. Consequently, a TCR CP may provide effective treatment for conditions including, but not limited to, atopic dermatitis, psoriasis and lichen planus [29], by efficiently abrogating T-cell-mediated immune responses [25]. Although it is not necessary to understand the mechanism of an invention, it is believed that the proposed SCHOOL model predicts this therapeutic effect. [9,10]. Further, studies of the epidermal growth factor and ErbB2 receptors have shown that synthetic peptides encompassing the transmembrane domains of these receptors inhibit the autophosphorylation and signaling pathway of their cognate receptor. These peptides are thought to block or disrupt specific transmembrane interactions, thereby inhibiting receptor dimerization and activation. [32]. The sequence-based blockade of the inter-receptor transmembrane protein interactions provides indirect evidence of the clinical relevance of a MIRR transmembrane-targeted strategy.

b. Homointeractions Between the Cytoplasmic Domains of Signaling Subunits

Figure 9C:
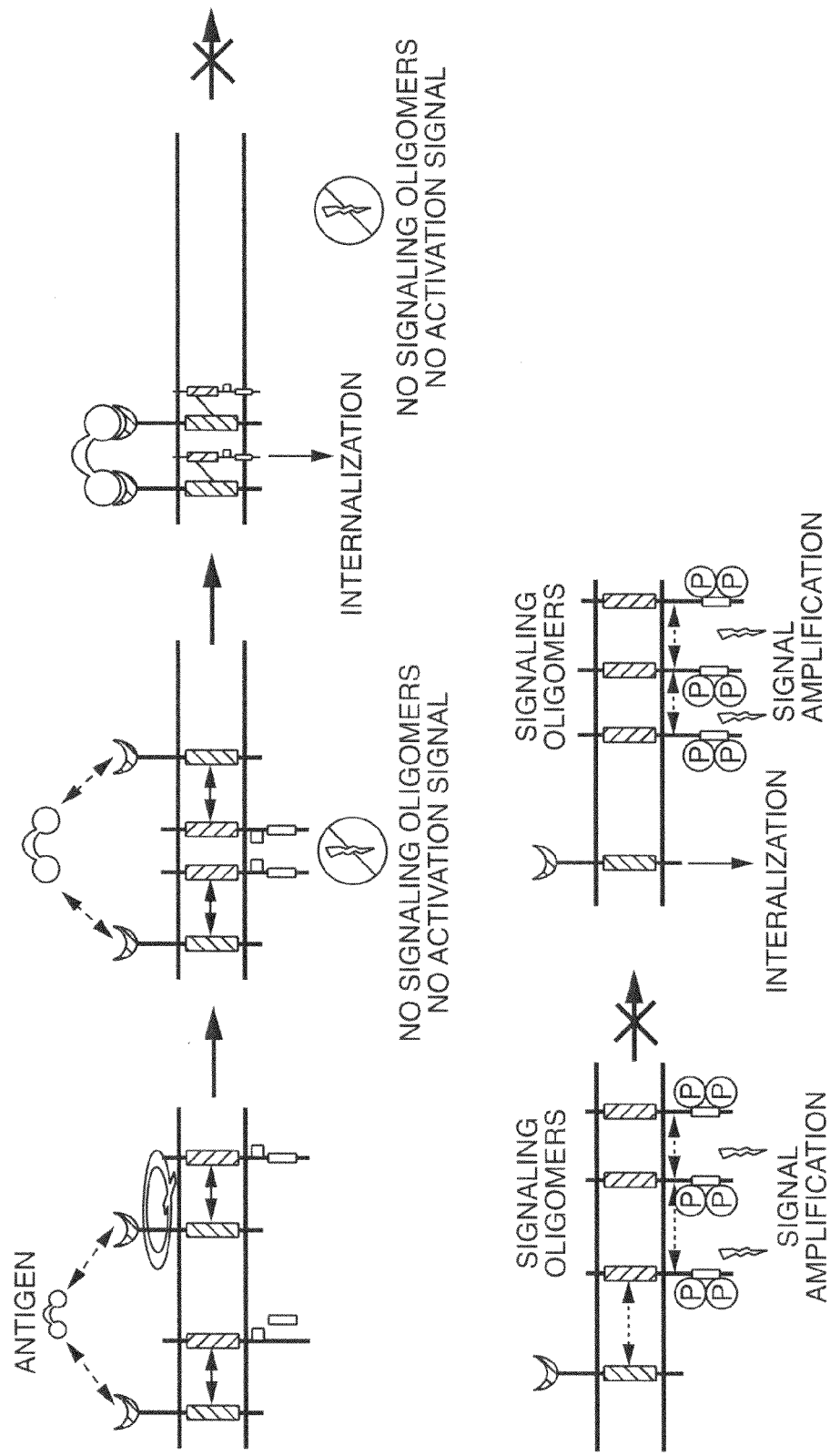
FIGS. 9C and 9D illustrate one embodiment of homointeractions between cytoplasmic domains of signaling subunits representing a second point of intervention (i.e., Target 2). Disruption of these interactions prevents the formation of signaling oligomers and inhibits cell activation following stimulation with either antigen or crosslinking antibody to signaling subunits.
Figure 9D:
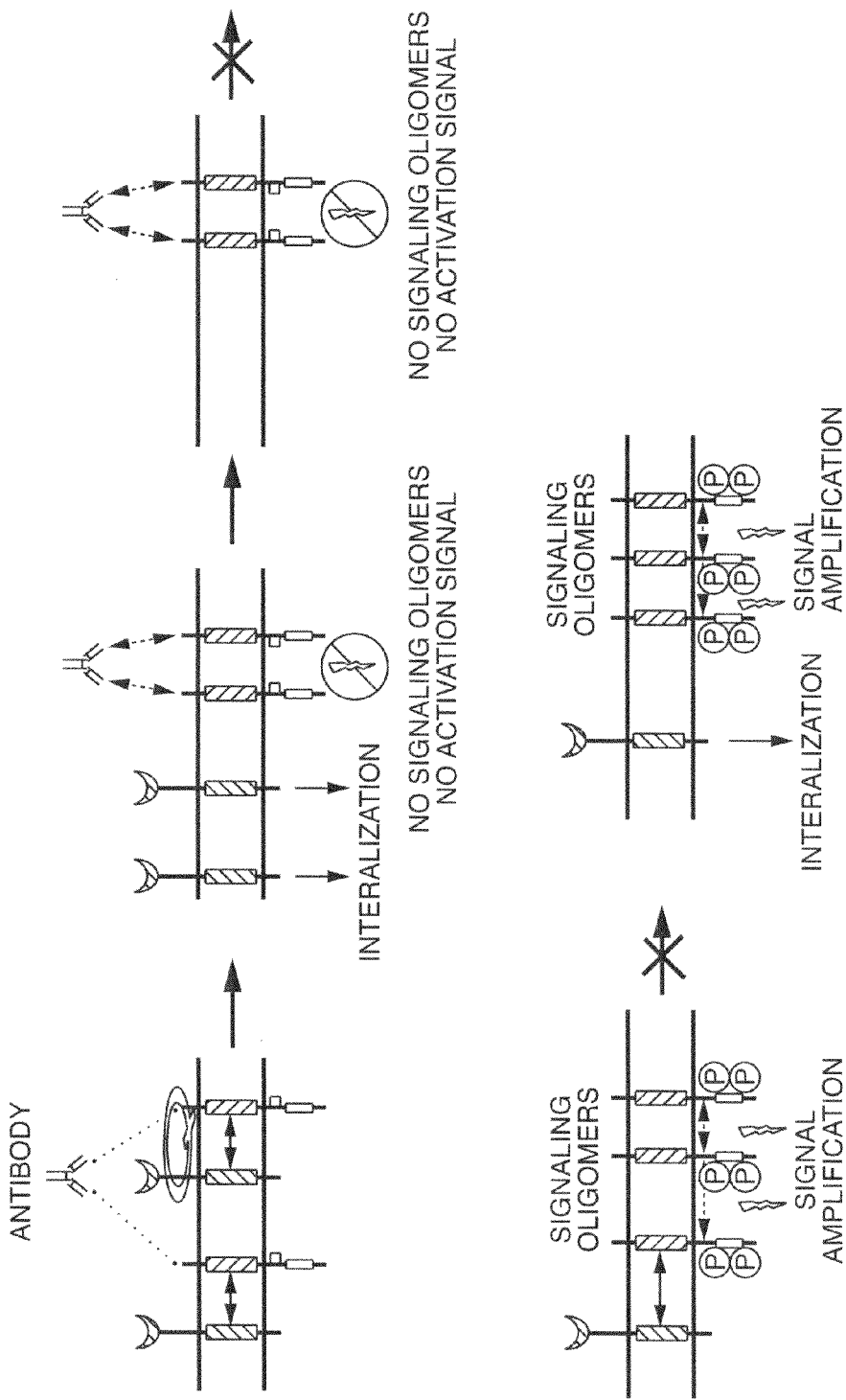

Although it is not necessary to understand the mechanism of an invention, it is believed that the SCHOOL model also predicts that a specific blockade of cytoplasmic domain homointeractions may be achieved by using cytoplasm-targeted agents or site-specific point mutations within the oligomerization interfaces, thereby preventing the formation of signaling oligomers and the initiation of a MIRR-mediated cell response (Target 2). See, FIGS. 9C and 9D. Similar to Target 1, modulation of the homointeractions between particular signaling cytoplasmic domains might enable modulation of a ligand-induced cell response. In addition, the ability to selectively prevent the formation of signaling oligomers of particular subunit(s) might provide a useful tool in functional studies of MIRRs.

Recently, the ligand-induced formation of surface receptor oligomers has been reported for the Fas receptor. [33]. This single-chain receptor has a cytoplasmic death domain (DD) that, upon ligand stimulation, binds to the homologous DD of the adaptor protein Fas-associated death domain protein (FADD) and homo-oligomerizes, thus initiating the caspase signaling cascade. A mutation in Fas cytoplasmic domain (T225K) was linked to an autoimmune lymphoproliferative syndrome that impairs receptor oligomerization and inhibits Fas mediated signaling but retains the ability to interact with FADD. This may be interpreted as the homointeractions between signaling cytoplasmic tails play a role in ligand-induced surface-receptor oligomerization and subsequent signaling. Thus, the proposed MIRR cytoplasm targeted strategy is consistent with these observations.

2. HIV Therapy

The HIV-1 gp41 fusion peptide (FP) in the N-terminus of the HIV envelope glycoprotein gp41 functions with other gp41 domains to fuse the virion with the host cell membrane. This peptide co-localizes with CD4 and TCR molecules, co-precipitates with the TCR and inhibits antigen-specific T-cell activation [24]. These effects are specific; T-cell activation through phorbol 12-myristate 13 acetate and ionomycin, or anti-CD3 antibodies is not affected by FP [24]. As with TCR CP, HIV FP has immunosuppressive activity in vivo [24].

Figure 10A:
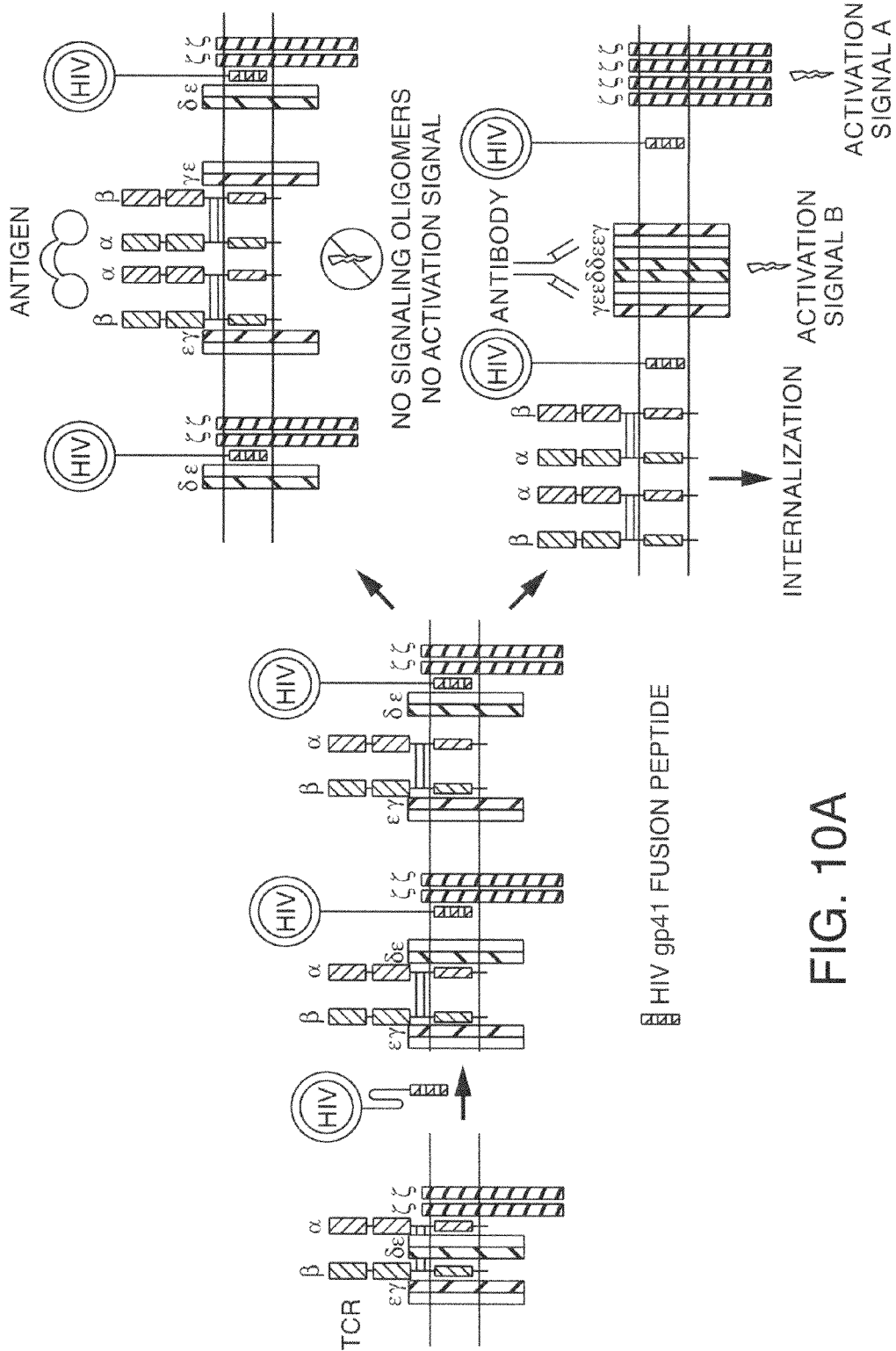
FIG. 10A illustrates a proposed molecular mechanism of action of the HIV-1 gp41 FP during its insertion into a target T-cell membrane. The peptide blocks transmembrane interactions between a recognition chain (TCRoE) and signaling subunits (CD3de heterodimer and zz homodimer), resulting in 'pre-dissociation' of the TCR complex, thus preventing the formation of signaling oligomers and inhibiting antigen-dependent T-cell activation. By contrast, stimulation of these 'pre-dissociated' TCRs with clinically relevant monoclonal antibodies specific for the CD3e chain of the TCR complex (OKT3) do affect receptor triggering and cell activation. Interchain homointeractions in signaling oligomers are not shown.

The SCHOOL model provides a molecular mechanism of action for HIV FP and explains the observed difference in the response of T cells. See, FIG. 10A; and [24]. The illustration demonstrates how this peptide may prevent the formation of signaling oligomers and, thus, inhibit antigen-dependent T-cell activation, acting similarly in this respect to TCR CP [25]. However, stimulation with anti-CD3 antibodies of these pre-dissociated TCRs still results in receptor triggering and cell activation. Thus, the model indicates that clinically relevant antibodies (e.g. OKT3) could be used to modulate the T-cell response during HIV infection. Recently, OKT3 antibodies have been used successfully in immune-activation HIV therapy [34]. The HIV-1 pathogenicity factor Nef increases viral replication in vivo. Notably, Nef lowers the threshold of T-cell activation [35,36]. Other studies have shown that Nef induces the transcription of an array of genes that is almost identical to that triggered upon exogenous stimulation of TCRs [37]. Thus, the extent of T-cell activation imprinted by Nef expression is controversial. Although Nef binds to the TCR z chain [38], the role of this interaction and the mechanism used by Nef to modulate T-cell activation remain unknown.

Figure 10B:
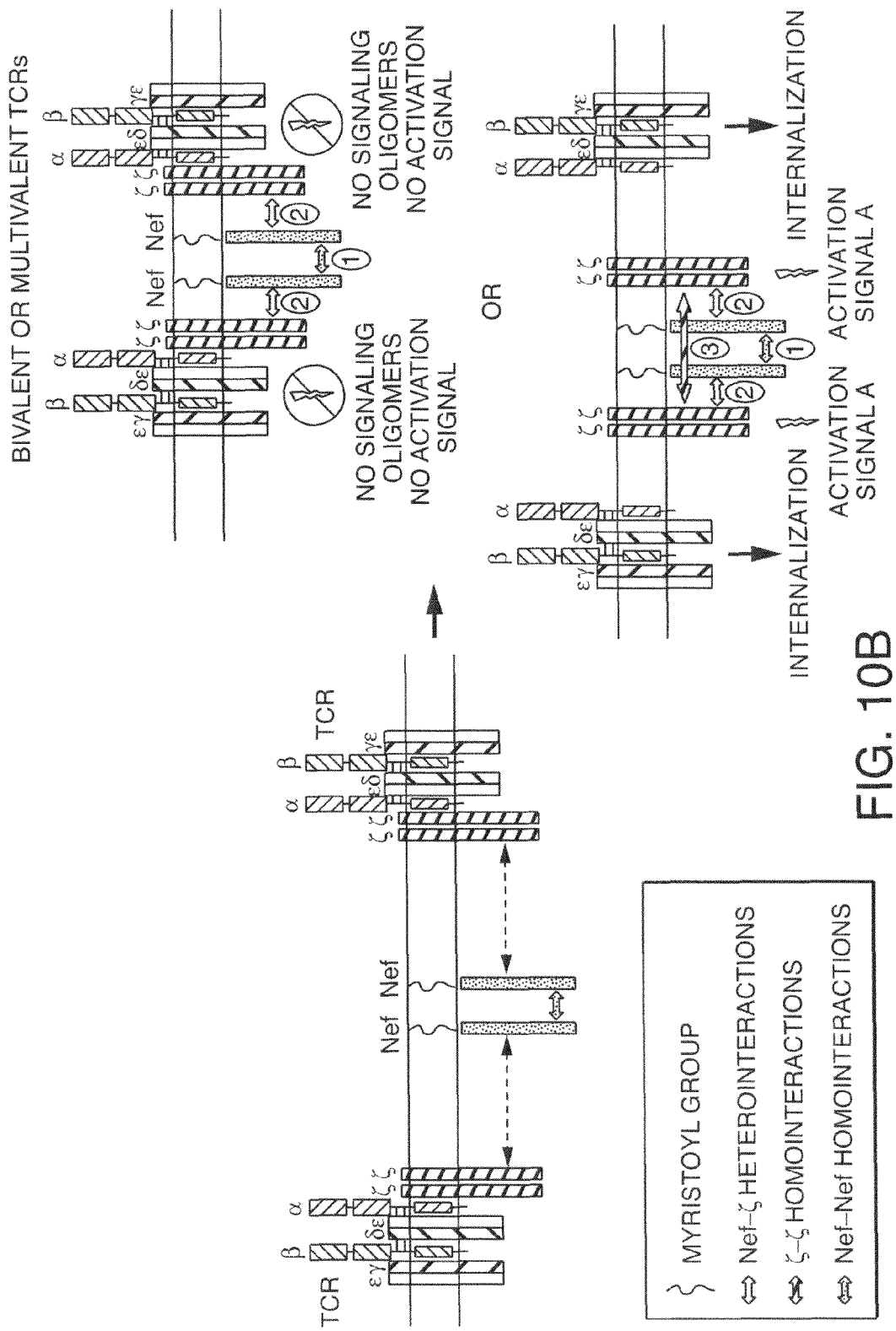
FIG. 10B illustrates a proposed mechanism of T-cell sensitization or activation mediated by the HIV-1 pathogenicity factor Nef. When expressed, natively dimeric or oligomeric Nef protein crosslinks z chains, clustering TCRs into bivalent or multivalent complexes and, thus, lowering the threshold of activation of HIV-1-infected T cells. Alternatively, Nef dimers might crosslink z chains, bringing them into sufficient proximity and proper orientation for homointeraction and the formation of signaling oligomers, thus generating an activation signal. Potential points of intervention are numbered.

Within the model, natively oligomeric Nef might crosslink homodimeric z chains, leading to the formation of multivalent TCR complexes that sense low concentrations of antigen [39]. Thus, this mechanism could explain the observed activation sensitization in T cells by Nef [35,36]. Alternatively, Nef dimers might crosslink z homodimers and form signaling z oligomers, thus generating an activation signal 'A' [9,10]. Both mechanisms might occur in vivo, and selection between these alternative pathways could depend on the type of cell infected and/or the cell-membrane lipid content. Thus, heterointeractions at the Nef-z interface, and homointeractions in Nef and z homo-oligomers might represent attractive targets for the design of antiviral agents. See, FIG. 10B.

3. Anti-Thrombotic Therapy

In one embodiment, the present invention contemplates a pharmaceutical composition comprising a GPVI peptide variant and/or a GPVI peptide variant conjugate. In one embodiment, the composition comprises an amount of the peptide variant effective to treat a platelet-mediated disorder. In some embodiments, the composition further comprises a pharmaceutically acceptable carrier, diluent, and/or excipient.

In some embodiment, the peptides and compositions contemplated in the present invention may be effectively used in antithrombotic therapy comprising a long-term usage of medications to prevent and treat platelet-mediated disorders (i.e., for example, coronary thrombosis). In one embodiment, a prolonged therapy using these derivatives and/or compounds may be effective substitutes for non-steroidal anti-inflammatory drugs (NSAIDs, i.e., for example, aspirin), thereby avoiding gastrointestinal and neurological related side effects of NSAIDs.

In one embodiment, the present invention contemplates a drug delivery platform comprising the peptides and derivatives thereof. In one embodiment, the peptide variants enter a cell membrane (i.e., for example, a platelet cell membrane), wherein said peptide variants comprise a therapeutic agent. Although it is not necessary to understand the mechanism of an invention, it is believed that peptide variants comprising a therapeutic agent could be used as "carriers" to intracellularly deliver the therapeutic agents. In one embodiment, the therapeutic agent is conjugated to the peptide variant.

In one embodiment, the present invention contemplates a method of treating a mammal exhibiting symptoms of a disorder in which platelets are involved or recruited. In one embodiment, the method comprises administering to the mammal a pharmacologically effective amount of the peptide variant and/or pharmaceutical composition comprising the peptide variant.

In some embodiments, the peptide variants and/or pharmaceutical compositions comprising the peptide variants may be administered by intradermal or intravenous injection, inhalation, parenteral, intraocular, transdermal as well as by any other appropriate routes.

In one embodiment, the present invention contemplates a method for reducing cardiovascular stent thrombosis and/or restenosis (i.e., for example, a recurring coronary artery blockage). In one embodiment, the method comprises treating a patient exhibiting symptoms of coronary artery disease, wherein said patient has undergone angioplasty procedures and cardiovascular stent placement. In one embodiment, the cardiovascular stents comprise a pharmacologically effective amount of the peptide variant and/or composition comprising the peptide variant. In one embodiment, the peptide variant is attached to the stent, wherein said attachment comprises, covalent and/or non-covalent boding, wherein the peptide variant is immobilized on a modified and/or unmodified stent surface. Although it is not necessary to understand the mechanism of an invention, it is believed that the peptide variants can be attached to a stent surface by many different methods. Suzuki et al., "Stent-based delivery of sirolimus reduces neointimal formation in a porcine coronary model" *Circulation* 104:1188-1193 (2001); Prunotto et al., "Stenting: biomaterials in mini-invasive cardiovascular applications" *Anal. Bioanal. Chem.* 381:531-533 (2005); Tsuji et al., "Biodegradable stents as a platform to drug loading" *Int. J. Cardiovasc. Intervent.* 5:13-16 (2003); Whelan et al., "Mechanisms of drug loading and release kinetics" *Semin. Interv. Cardiol.* 3:127-131 (1998); Austin et al., "Protective loading of stents" U.S. Pat. No. 7,096,554 (all references herein incorporated by reference).

In some embodiments, the present invention contemplates a method to prevent and/or treat disorders involving collagen-induced platelet functions such as platelet adhesion, aggregation, or activation, or in disorders wherein the platelets are involved and/or recruited, wherein the treatment comprises administering to a subject peptide variants and/or compositions comprising peptide variants contemplated by the present invention. Such disorders contemplated by the present invention include, but are not limited to, atherosclerosis, coronary artery disease, ischemic cerebrovascular disease (i.e., for example, focal cerebral ischemia, carotid artery atherothrombotic disease, or cerebral embolism), peripheral vascular disease, diabetes mellitus comprising symptoms of, for example, diabetic vascular disease or diabetic thrombocytopathy, renal disease (i.e., for example, glomerular disease), inflammatory diseases (i.e., for example, inflammatory bowel disease, asthma, cystic fibrosis, rheumatoid arthritis, skin diseases, or Kawasaki disease), tumor growth and metastasis, Alzheimer's disease, psychiatric disorders (i.e., for example, anxiety disorders, mood disorders, alcoholism, eating disorders, schizophrenia, or childhood developmental/psychiatric disorders), thrombocytopenia (i.e., for example, HIV-1-related thrombocytopenia, heparin- and/or drug-induced thrombocytopenia, thrombocytopenia in newborns), platelet function defects, von Willebrand disease, immune thrombocytopenia purpura, or inherited and acquired disorders of platelet function.

C. High-Throughput Screening Methods

Figure 5A:
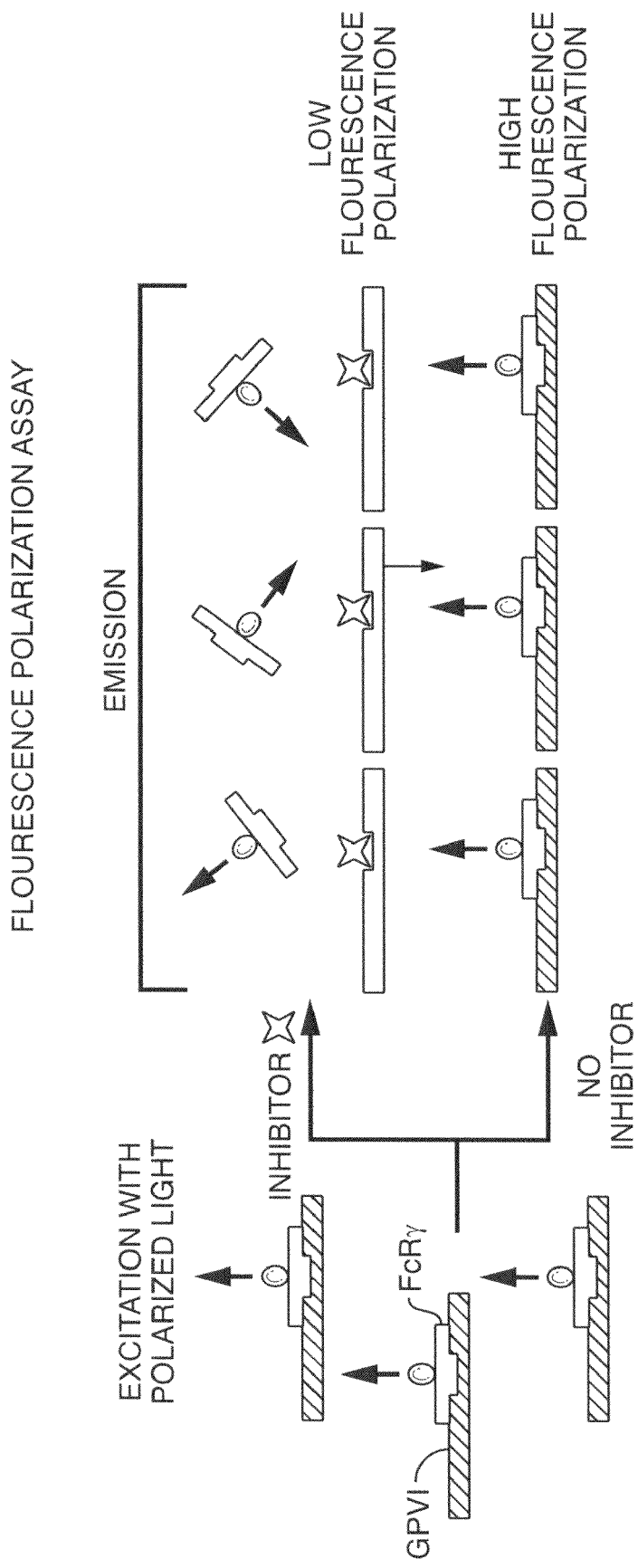
FIG. 5A shows one embodiment of a fluorescence polarization assay that could be used in high-throughput screening strategies to identify both peptide and nonpeptide inhibitors of protein-protein interaction between GPVI and FcRγ subunits of the GPVI-FcRγ signaling complex. Gray oval: fluorophore; Arrow: transition vector of fluorescence emission.

In one embodiment, the invention contemplates a method for screening an effective nonpeptide small-molecule inhibitors that blocks/inhibits/prevents/disrupts a protein-protein interaction of GPVI and FcRγ subunits of the GPVI-FcRγ signaling complex. These molecules may be discovered using any one of several high-throughput screening methods for protein-protein interaction inhibitors. Stockwell, B. R., "Exploring biology with small organic molecules" *Nature* 432:846-854 (2004); Kay et al., "High-throughput screening strategies to identify inhibitors of protein-protein interactions" *Mol. Diversity.* 1:139-140 (1996); Pfleger et al., "Extended bioluminescence resonance energy transfer (eBRET) for monitoring prolonged protein-protein interactions in live cells" *Cell Signaling* 18:1664-1670 (2006); Jung et al., "Surface plasmon resonance imaging-based protein arrays for high-throughput screening of protein-protein interaction inhibitors" *Proteomics* 5: 4427-4431 (2005); Nieuwenhuijsen et al., "A dual luciferase multiplexed high-throughput screening platform for protein-protein interactions" *J. Biomol. Screen* 8:676-684 (2003); and Berg, T., "Modulation of protein-protein interactions with small organic molecules" *Angew. Chem. Int. Ed. Engl.* 42:2462-2481 (2003). These assays are compatible with high-throughput screening strategies used to identify both peptide and nonpeptide inhibitors of protein-protein interaction between GPVI and FcRγ subunits of the GPVI-FcRγ signaling complex. See, FIGS. 5A, 5B, & 5C.

EXPERIMENTAL

The following non-limiting Examples are put forth so as to provide those of ordinary skill in the art with illustrative embodiments as to how the compounds, compositions, articles, devices, and/or methods claimed herein are made and evaluated. The Examples are intended to be purely exemplary of the invention and are not intended to limit the scope of what the inventor regard as his invention. Efforts have been made to ensure accuracy with respect to numbers (e.g., amounts, temperature, etc.) but some errors and deviations should be accounted for. Unless indicated otherwise, parts are parts by weight, temperature is in ° C., or is at ambient temperature, and pressure is at or near atmospheric.

Example 1

Synthesis of Peptides

This example demonstrates one embodiment of a synthesized GPVI related peptide.

The first step was to synthesize the short hydrophobic peptide corresponding to a portion of a GPVI transmembrane domain sequence. Although it is not necessary to understand the mechanism of an invention, it is believed that this peptide is involved in GPVI-FcRγ receptor assembly and may interact with a FcRγ protein in a competitive fashion.

The synthesis of peptides may involve the use of protecting groups. Peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

In one embodiment, the amino acid sequence of a competitive peptide comprises $NH_2$-Gly-Asn-Leu-Val-Arg-Ile-Cys-Leu-Gly-Ala-Val-OH (i.e., GNLVRICLGAV; SEQ ID NO:9), hereafter referred to as "core peptide" or "CP". In another embodiment, the amino acid sequence of a competitive peptide comprises $NH_2$-Gly-Asn-Leu-Val-Ala-Ile-Cys-Leu-Gly-Ala-Val-OH (i.e., GNLVAICLGAV; SEQ ID NO: 34) wherein, $Arg^5$ of CP substituted with $Ala^5$, hereafter referred to as "core peptide-A" or "CP-A".

Although it is not necessary to understand the mechanism of an invention, it is believed that the positively charged $Arg^5$ in the CP transmembrane domain of GPVI forms a salt bridge to an aspartic acid residue in the transmembrane domain of the FcRγ-chain. Moroi et al., "Platelet glycoprotein VI: its structure and function" *Thromb. Res.* 114:221-233 (2004). Thus, CP-A may be considered a "control peptide" because of the $Ala^5$ substitution.

Unprotected peptides were purchased from Sigma-Genosys (Woodlands, Tex., USA) with greater than 95% purity for CP and 90% purity for CP-A as assessed by HPLC. Peptide molecular mass was checked by matrix-assisted laser desorption ionization mass spectrometry.

Example 2

Solubility

This example demonstrates that the hydrophobic properties of GPVI core peptides may be overcome without risking cell toxicity.

The CP and CP-A peptides were noted to be hydrophobic and insoluble in aqueous solutions. A variety of solvents and carriers were tested to improve their solubility. Solvents and/or carriers that improve solubility of CP and CP-A included, but were not limited to, ethanol, dimethylsulphoxide (DMSO), dimethyl formamide (DMF), and trifluoracetic acid (TFA). When using DMSO as a solvent, the final concentration used in the platelet function experiments ranged from 0.063%-0.250%. DMSO concentrations greater than 1% were observed toxic to cells. Stock solutions of CP and CP-A were prepared in DMSO and used at a 1:2000, 1:1000, or 1:400 dilution.

Example 3

Whole Blood Samples

Peripheral blood was drawn from healthy, nonsmoking adult volunteers (IRB-approved written informed consent) who had not received any platelet inhibitory drugs in the preceding 2 weeks. After discarding the first 2 mL, blood was drawn into a 3.2% sodium citrate Vacutainer® (Becton Dickinson, Franklin Lakes. N.J., USA).

Example 4

Effect of Glycoprotein VI Core Peptide on Collagen-Induced Platelet Activation Using Whole Blood Flow Cytometry Flow cytometric analysis may be used to evaluate platelet function, and/or the assessment of platelet activation. Michelson, A. D., "Evaluation of platelet function by flow cytometry" *Pathophysiol. Haemost. Thromb.* 35:67-82 (2006). In the absence of an added exogenous platelet agonist, whole blood flow cytometry can determine the activation state of circulating platelets, as judged by the binding of an activation-dependent monoclonal antibody. In addition to this assessment of platelet function in vivo, inclusion of an exogenous agonist in the assay enables analysis of the reactivity of circulating platelets in vitro. In the latter application, whole blood flow cytometry is a physiological assay of platelet function in that an agonist results in a specific functional response by the platelets: a change in the surface expression of a physiological receptor (or other antigen or bound ligand), as determined by a change in the binding of a monoclonal antibody.

Markers of platelet activation include activation-dependent changes in the glycoprotein IIb/IIIa complex and exposure of granule membrane proteins. The platelet glycoprotein IIb/IIa complex is believed involved with biochemical events leading to activation, and may express an activation dependent epitope recognized by monoclonal antibody PAC-1. Shattil et al., "Changes in the platelet membrane glycoprotein IIb/IIIa complex during platelet activation" *J. Biol. Chem.* 260:11107-11114 (1985). P-Selectin (GMP-140, PADGEM, CD-62P) is now known to be a component of the alpha-granule membrane and is therefore exposed on the surface of the platelet upon activation, due to the fusing of the vesicle with the outer membrane. These two markers of platelet activation were used to study the effect of peptide on collagen-induced platelet activation using whole blood flow cytometry.

Materials

The final concentration of a peptide used in incubation (i.e., for example, the GPVI CP) was 100 µM. The following antibodies (and appropriately matched isotype control antibodies) were used for flow cytometry analysis: fluorescein isothiocyanate (FITC)-conjugated PAC-1 monoclonal antibody which recognizes the activated conformation of glycoprotein (GP) IIb/IIIa; phycoerythrin (PE)-conjugated anti-CD62P monoclonal antibody directed against P-Selectin; and PECy7-conjugated anti-CD41 monoclonal antibody which recognizes the α-subunit of the CD41/CD61 complex (GPIIb-IIIa) (BD-Pharmingen, San-Diego, Calif., USA; and/ or DAKO, Carpinteria, Calif., USA).

Prior to flow cytometric experiments, PE-conjugated anti-CD62P and anti-CD41 antibodies were mixed at a ratio of 1:2.5 (volume/volume) and diluted at a ratio of 1:9 (volume/volume) with 10 mmol/L HEPES, 0.15 mol/L NaCl, pH 7.4, containing 1% bovine serum albumin (BSA) and 15 mmol/L sodium azide. Collagen was purchased from Chronolog Corp (Havertown, Pa., USA). The stock 1 mg/mL collagen solution was diluted at a ratio of 1:10 (volume/volume) with 10 mmol/L HEPES, 0.15 mol/L NaCl, pH 7.4. Stock solutions of GPVI core peptide in DMSO (or pure DMSO as a "vehicle" control) were diluted at a ratio of 1:10 (volume/volume) with 10 mmol/L HEPES, 0.15 mol/L NaCl, pH 7.4, immediately before the addition of blood samples.

Method

Flow cytometric analysis: aliquots of citrated whole blood were incubated at 37° C. for 60 min with vehicle (DMSO; in a final concentrations of 0.063, 0.125 or 0.250%) or a preliminarily diluted GPVI core peptide in a final concentration of 100 µM. Then, the aliquoted samples were stimulated with 20 µg/mL collagen for 5 minutes at 37° C. in the presence of monoclonal antibody FITC-PAC-1. After stimulation, the samples were fixed by the addition of 1% formaldehyde in 10 mmol/L HEPES, 0.15 mol/L NaCl, pH 7.4. After a 20 minute fixation period, the samples were diluted with 1% BSA in 10 mmol/L HEPES, 0.15 mol/L NaCl, pH 7.4, 0.15 mol/L NaCle, pH 7.4, and stained with preliminarily mixed monoclonal antibodies CD41-PE (as a platelet identifier) and CD62P-PE (P-selectin specific). Sample analysis was performed in a Becton Dickinson FACS-Calibur flow cytometer with CellQuest® software (Becton Dickinson). Barnard et al., "Effects of platelet binding on whole blood flow cytometry assays of monocyte and neutrophil procoagulant activity" *J. Thromb. Haemost.* 3:2563-2570 (2005). Positive analysis regions for P-selectin were set with appropriate non-specific controls. PAC-1 was analyzed by mean fluorescence intensity. The data are reported as mean fluorescence intensity (MFI) as percentage of the control sample and percentage of positive as determined by antigen-specific antibody binding above that of the isotypic control antibody. Results reported are mean±SD from triplicate samples.

Results

Figure 6A:
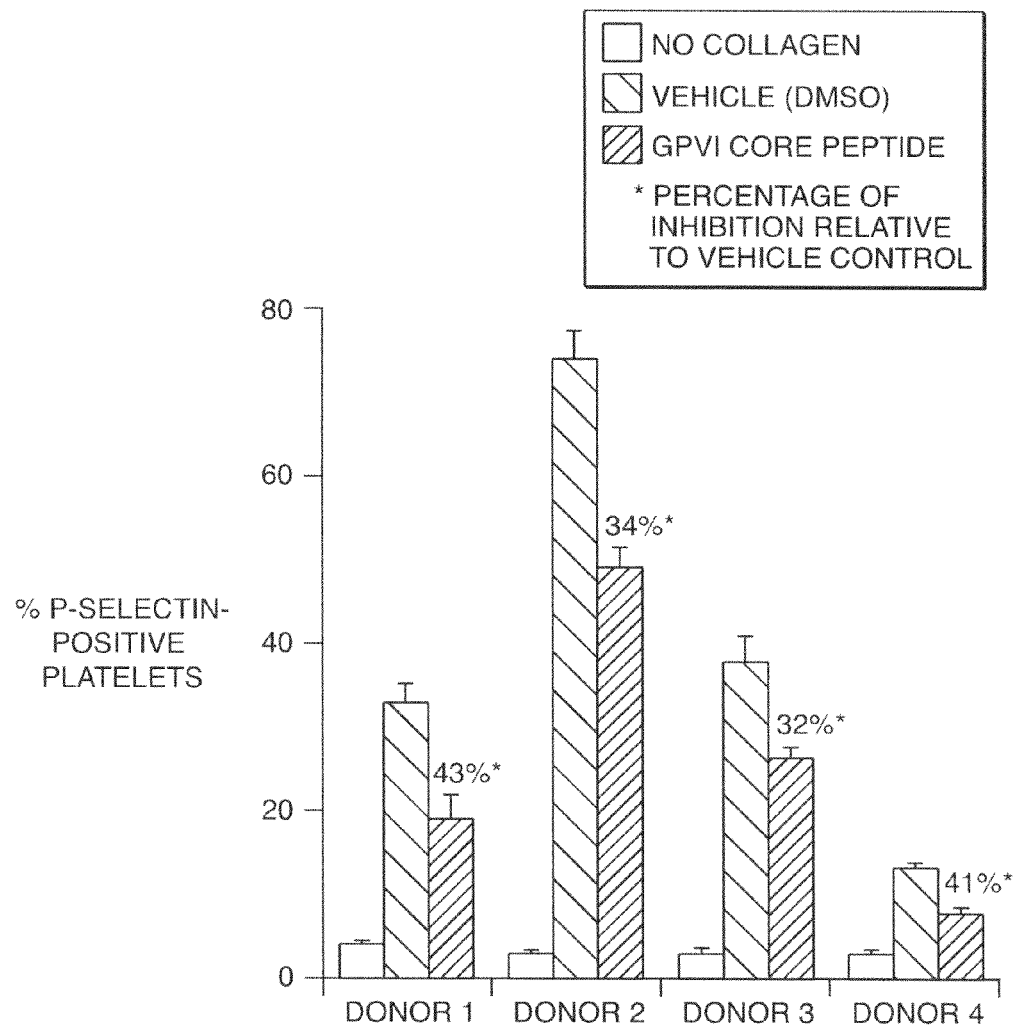
FIG. 6A presents exemplary data showing an effect of glycoprotein VI core peptide (GPVI-CP) on collagen-mediated platelet activation as measured as percentage of P-Selectin-positive platelets. Mean±standard error (n=3). GPVI-CP peptide was 100 μM.
Figure 6B:
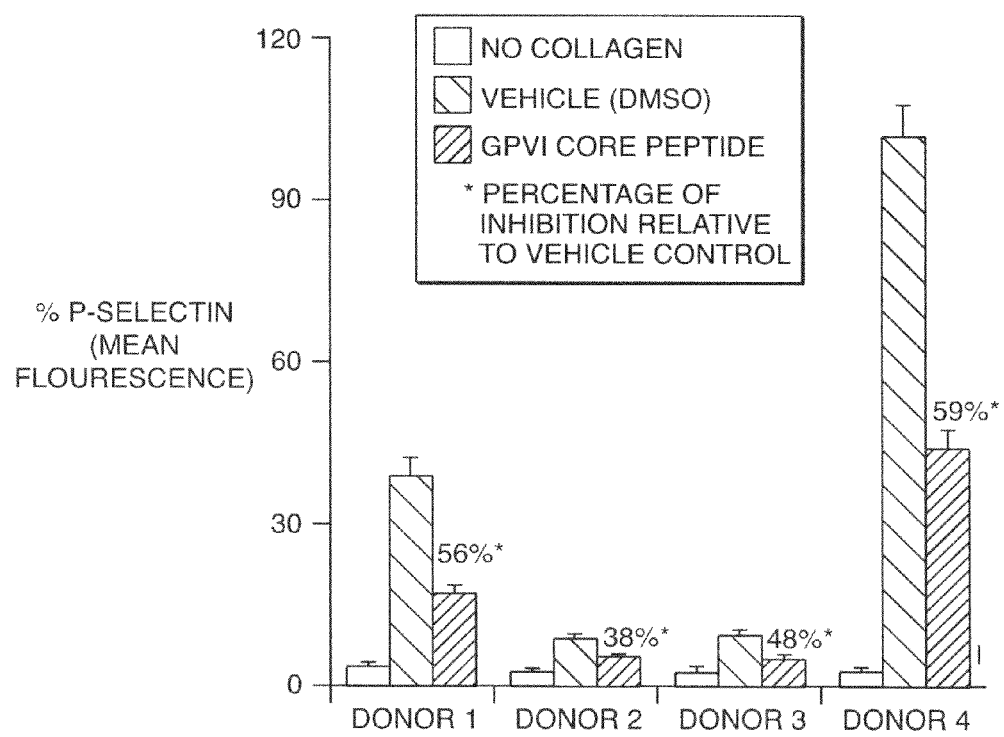
FIG. 6B presents exemplary data showing an effect of glycoprotein VI core peptide (GPVI-CP) on collagen-mediated platelet activation as measured by P-Selectin mean fluorescence surface expression intensity. Mean±standard error (n=3). GPVI-CP peptide was 100 μM.
Figure 6C:
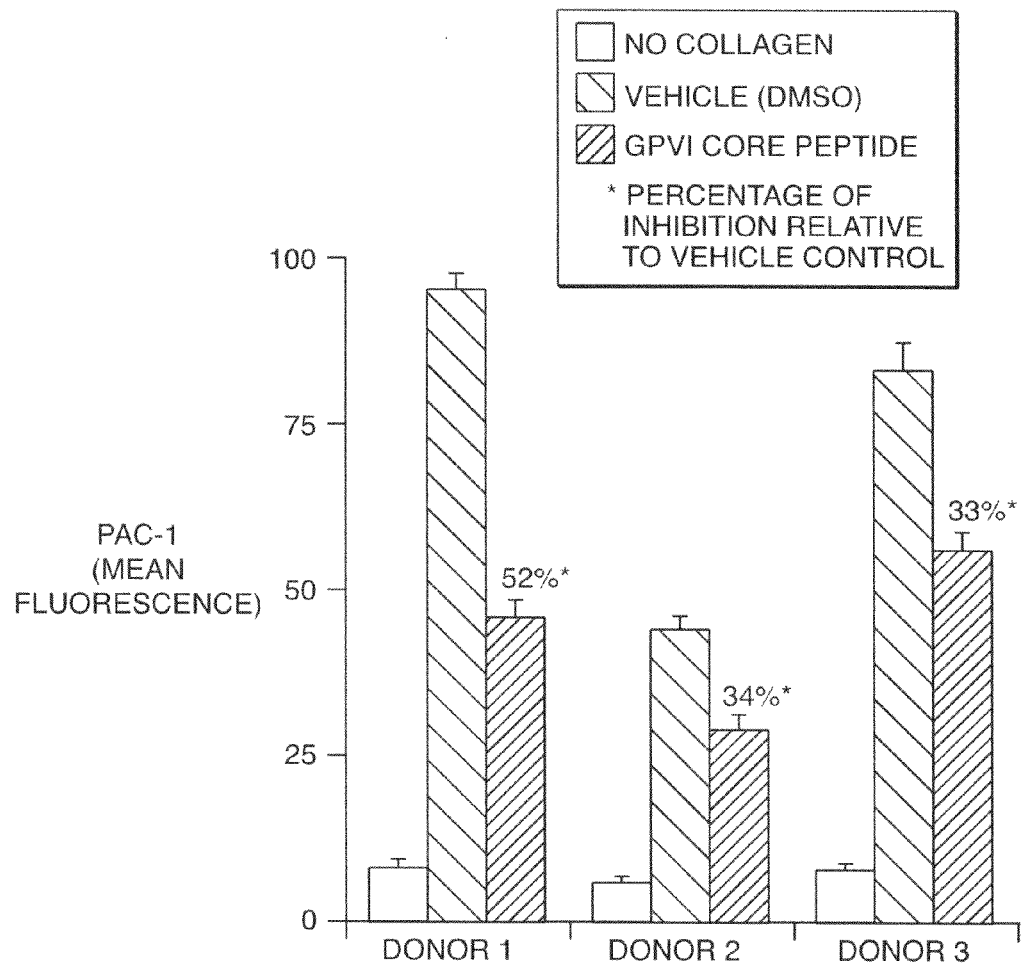
FIG. 6C presents exemplary data showing an effect of glycoprotein VI core peptide (GPVI-CP) on collagen-mediated platelet activation as measured by PAC-1 mean fluorescence surface expression intensity. Mean±standard error (n=3). GPVI-CP peptide was 100 μM.

In experiments where collagen (antigen) was omitted, there were no P-Selectin-positive platelets and significant P-Selectin or PAC-1 surface expression. See, FIG. 6A-C, "No Collagen" bars. Addition of 20 µg/mL collagen in the presence of vehicle (DMSO) resulted in platelet activation measured as percentage of P-Selectin-positive platelets as well as P-Selectin and PAC-1 mean fluorescence surface expression intensities. See, FIGS. 6A-C, "Vehicle" bars. Preincubation of whole blood samples with GPVI core peptide in the final concentration of 100 µM prior to addition of collagen lead to a 32%-59% reduction in the expression of the platelet activation markers compared to vehicle control. See, FIG. 6A-C, "GPVI Core Peptide" bars.

Example 5

Concentration Effect of Glycoprotein VI Core Peptide on Collagen-Induced Platelet Activation Using Whole Blood Flow Cytometry Materials To examine the concentration-dependent effect of GPVI core peptide on collagen-induced platelet activation, the final concentration of the peptide used in incubation was varied from 50 to 200 µM, namely, 50, 100 or 200 µM. Other materials and procedures were as described in Example 4.

Method

As described in Example 4.

Results

Figure 7:
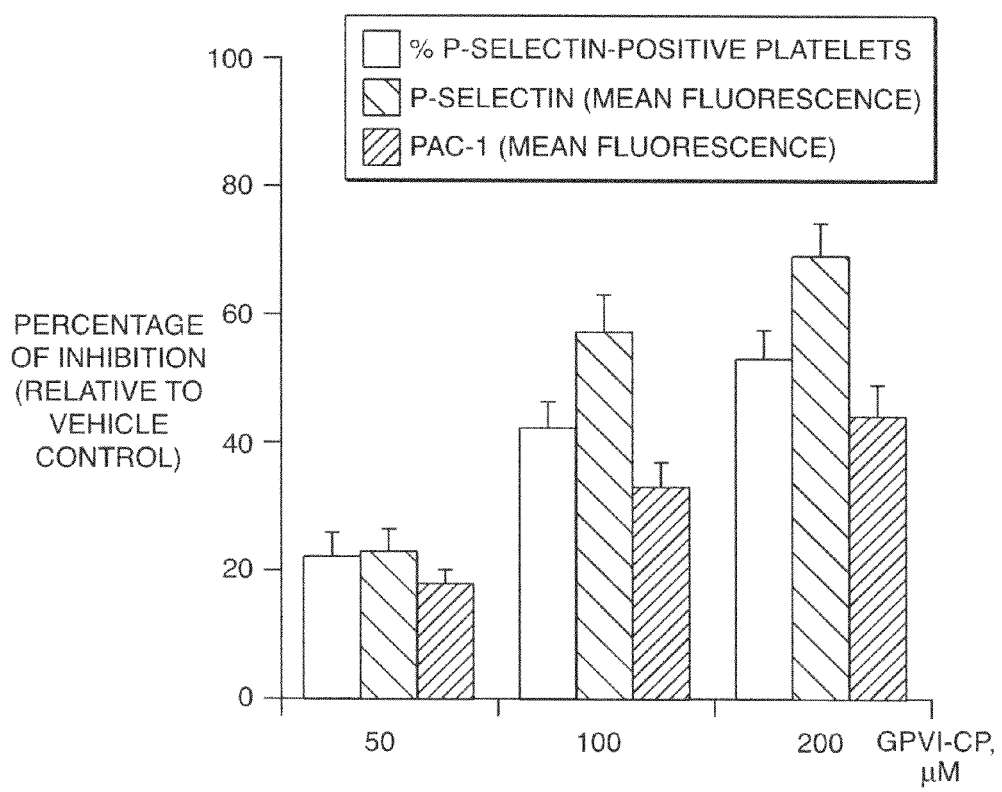
FIG. 7 presents exemplary data showing a concentration-dependent effect of glycoprotein VI core peptide (GPVI-CP) on collagen-mediated platelet activation as measured by a percentage of P-Selectin-positive platelets, as well as by P-Selectin and PAC-1 mean fluorescence surface expression intensities. Mean±standard error (n=3). GPVI-CP peptide was 50, 100, and 200 μM.

Measurements of the expression of the platelet activation markers such as percentage of P-Selectin-positive platelets as well as P-Selectin and PAC-1 mean fluorescence intensities at different concentrations of GPVI core peptide (50, 100 or 200 µM) clearly indicated that the peptide inhibited platelet activation in a concentration-dependent manner. See, FIG. 7.

Example 6

Effect of Glycoprotein VI Core Peptide with Arg Substituted with Ala on Collagen-Induced Platelet Activation Using Whole Blood Flow Cytometry Materials A final concentration of 100 µM GPVI-A CP was used in the incubation, wherein the GPVI core peptide's $Arg^5$ was substituted with $Ala^5$. Other materials and procedures were as described in Example 4.

Method

As described in Example 4.

Results

Figure 8A:
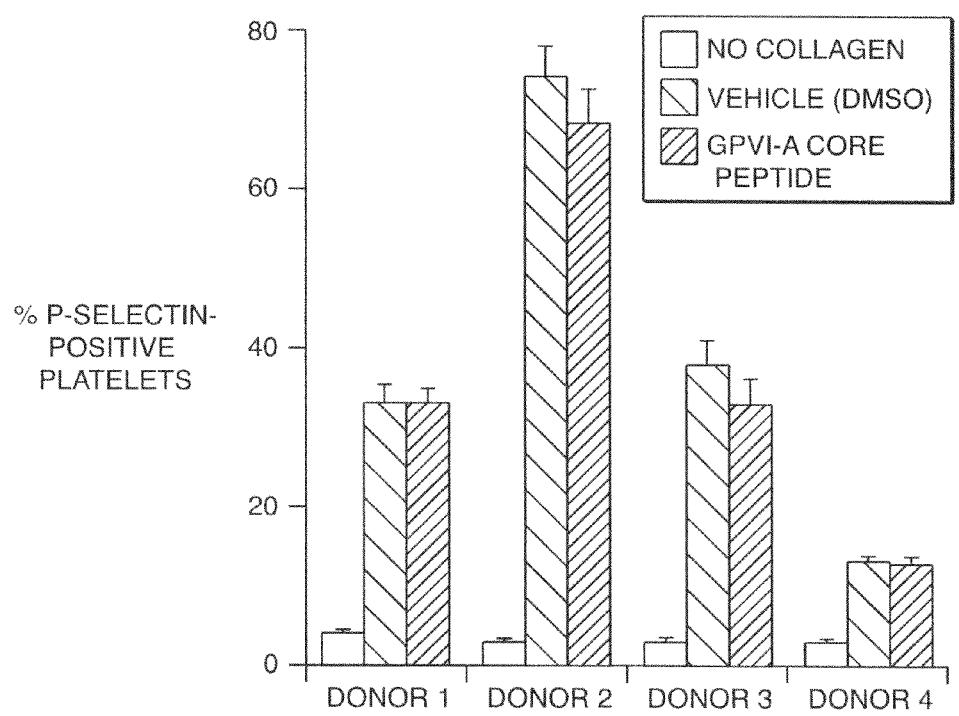
FIG. 8A presents exemplary data showing an absence of effect by glycoprotein VI core peptide with $Arg^5$ substituted with $Ala^5$ (GPVI-A CP) on collagen-mediated platelet activation as measured by a percentage of P-Selectin-positive platelets. Mean±standard error (n=3). GPVI-A CP peptide was 100 μM.
Figure 8B:
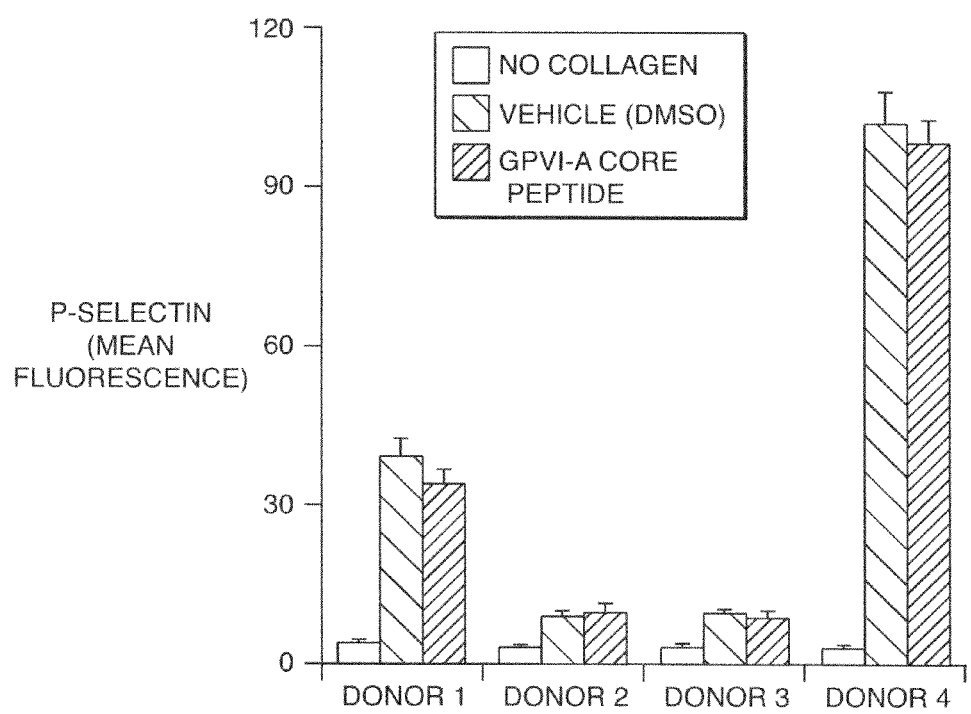
FIG. 8B presents exemplary data showing an absence of effect by glycoprotein VI core peptide with $Arg^5$ substituted with $Ala^5$ (GPVI-A CP) on collagen-mediated platelet activation as measured by P-Selectin mean fluorescence surface expression intensity. Mean±standard error (n=3). GPVI-A CP peptide was 100 μM.
Figure 8C:
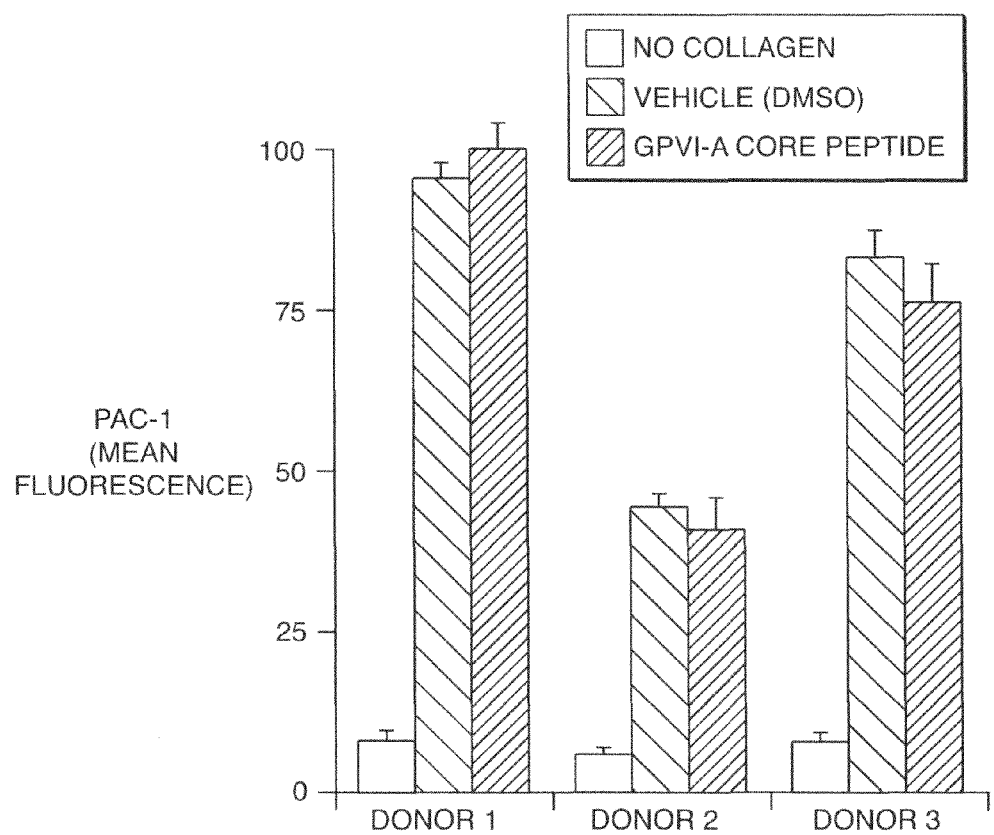
FIG. 8C presents exemplary data showing an absence of effect by glycoprotein VI core peptide with $Arg^5$ substituted with $Ala^5$ (GPVI-A CP) on collagen-mediated platelet activation as measured by PAC-1 mean fluorescence surface expression intensity. Means±standard error (n=3). GPVI-A CP peptide was 100 μM.

In experiments where collagen was omitted there were no P-Selectin-positive platelets nor P-Selectin or PAC-1 fluorescence surface expression intensities. See, FIG. 8A-C, "No Collagen" bars. Addition of 20 μg/mL collagen in the presence of vehicle (DMSO) resulted in platelet activation measured as percentage of P-Selectin-positive platelets as well as P-Selectin and PAC-1 mean fluorescence surface expression intensities. See, FIG. 8A-C, "Vehicle" bars. Preincubation of whole blood samples with GPVI-A CP before the addition of collagen did not lead to any significant differences in the expression of the platelet activation markers as compared to vehicle control. See, FIG. 8A-C, "GPVI-A Core Peptide" bars.

Example 7

Platelet Collection and Isolation

A. Blood, Plasma and Platelet Preparation

Platelet aggregation/activation studies can be performed using whole blood, platelet-rich plasma (PRP) or washed platelets. These samples can be prepared using the following standard protocols:

B. Whole Blood Preparation

Blood is collected from healthy human volunteers after full informed consent according to the Helsinki declaration. Blood is drawn by venipuncture either in 1/10 volume of 129 mmol/L trisodium citrate, or in 40 mmol/L D-Phe-L-Pro-L-Arg chloromethyl ketone (PPACK). The first 2.0-2.5 ml of drawn blood are discarded.

C. Platelet-Rich Plasma (PRP) Preparation

Citrated or PPACK-anticoagulated blood obtained as described above, is centrifuged at 130-260 g for 15 min to obtain PRP, and twice at 870-1500 g for 10-15 min for platelet-poor plasma (PPP). PRP is normalized to $1.5$-$2.5 \times 10^8$ platelets/ml with autologous PPP.

D. Platelet Isolation

Platelets are obtained from PRP by centrifugation at 1100 g for 20 min, following incubation for 10 min with 20 ng/mL prostaglandin $E_1$ ($PGE_1$), and washed three times using modified Tyrode's buffer (5 mM HEPES buffer, pH 7.4, 134 mM NaCl, 3 mM KCl, 0.3 mM $NaH_2PO_4$, 2 mM $MgCl_2$, 5 mM glucose, 12 mM $NaHCO_3$, 1 mM EGTA, 3.5 mg/mL bovine serum albumin, 20 n/mL $PGE_1$, 20 ng/mL apyrase). Finally, washed platelets are resuspended in modified Tyrode's buffer, substituting 2 mM $CaCl_2$ for 1 mM EGTA. The number of platelets is counted using a hematocytometer.

Example 8

Bleeding Time

Virtually all "anti-platelet" drugs prolong the bleeding time (i.e., are anti-coagulant drugs). For example, in mice, a soluble dimeric form of GPVI (GPVI-Fc) has been shown to inhibit GPVI-mediated platelet function and induce a moderate prolongation of tail bleeding times vs. control animals.

Bleeding time measurements can be easily performed demonstrating that a platelet "inhibitor" is effective in inducing a moderate prolongation of tail bleeding times.

1. Wild-type C57BL6/J mice are anesthetized by intraperitoneal injection of a solution of midazolame (5 mg/kg body weight), medetomidine (0.5 mg/kg body weight), and fentanyl (0.05 mg/kg body weight).

2. A platelet "inhibitor" (or vehicle) in various doses is administered (i.e., for example, intravenously).

3. Tail bleeding time is assessed 1 hr after injection of "inhibitor" or vehicle.

4. The tails of anesthetized mice are prewarmed for 5 min at 37° C. in a water bath and a 3-5-mm segment is amputated with a razor blade.

5. The tail is immersed immediately in 10 ml 37° C. prewarmed saline, and the time required to stop spontaneous bleeding is determined.

6. To evaluate rebleeding, after bleeding had stopped, the tail is submerged for another 60 min in 10 ml prewarmed (37° C.) saline containing 0.01 mM trisodium citrate.

7. The number of red blood cells and the amount of hemoglobin released from the tail wound during this 60-min period are determined.

Example 9

Platelet Aggregation

Platelet aggregation studies can be performed using either PRP or whole blood. When platelet aggregation studies are performed using PRP, unaggregated platelets suspended in plasma create a turbid solution that absorbs light. An agent (i.e., for example, a CP peptide or a functional derivative thereof) is added to the PRP that activates the platelets and induces aggregation. The aggregated platelets clump together and fall to the bottom of the tube. This results in an increase in light transmittance through the sample. The platelets show different aggregation responses based upon the strength of the activating stimulus.

With collagen, a potent platelet aggregation agonist, the platelets undergo a rapid and extensive aggregation with one "phase" for the complete aggregation response. Platelet aggregation can be also induced by the glycoprotein VI agonist convulxin. Convulxin, like a collagen, is commercially available.

Similar effects on platelet aggregation can be achieved using collagen-related peptides: collagen-related triple-helical peptide (CRP) and GKP*(GPP*) 10GKP*G (single letter amino acid code: P*=hydroxyproline). Both peptides can be synthesized using standard Fmoc solid-phase chemistry and are potent collagen-like stimulants of platelet activation.

Platelet aggregation measurements can be easily performed demonstrating that the "inhibitor" is effective in inhibiting collagen-induced platelet aggregation using, for example, one of the several protocols described below:

Protocol 1:

1. PRP or washed platelets are incubated in the absence or presence of various doses of "inhibitor" for 10-60 min at 37° C. in a 96-well flat-bottom plate in 50 mm Tris HCl, pH 7.4, containing 150 mm NaCl.

2. Platelet aggregation is initiated by addition of 2.0-5.0 mg/mL collagen, 4-8 nM convulxin, or 0.25 mg/mL CRP as platelet activators.

3. The reaction mixture is stirred continuously at 37° C. for 10 min.

4. Platelet aggregation is monitored by light transmittance using a microplate reader.

Protocol 2:

1. PRP is incubated in the absence or presence of various doses of "inhibitor" for 10-60 min at 37° C.

2. Platelet aggregation is started by addition of 2.0-5.0 mg/mL collagen, 4-8 nM convulxin, or 0.25 mg/mL CRP as platelet activators.

3. Platelet aggregation is monitored by light transmittance in the aggregometer with continuous stirring at 37° C.

Protocol 3:
1. Whole blood diluted 1:1 with 0.85% (w/v) saline is incubated in the absence or presence of various doses of "inhibitor" for 10-60 min at 37° C.
2. Then, the samples are supplemented with 2-10 mg/mL collagen, convulxin and/or CRP, and the impedance value reflecting the extent of platelet aggregation is read after additional 6 min (Whole Blood Aggregometer Chrono-Log 592, Chrono-Log Corp.).
3. For healthy donors, the values of impedance of 14 and 22 W can be accepted as the lower and upper normal limits, respectively, for collagen-induced whole blood platelet aggregation.

Example 10

Platelet Secretion Measured by Luciferase

Platelet secretion studies are performed with a "lumiaggregometer," which measures platelet release simultaneously with platelet aggregation. When performing platelet secretion (i.e., for example, release) studies, a standard curve using known amounts of ATP is constructed as a comparison to a patient's platelet release kinetics.

Platelet secretion measurements can be performed demonstrating that the "inhibitor" is effective in inhibiting collagen-induced platelet activation.

Platelet preparations are made in accordance with Example 7, except that firefly luciferase (FFE) is added to monitor ATP release simultaneously with platelet aggregation. The data obtained using the patient platelet preparations are compared to a standard curve. The standard curve is established using patient platelet rich plasma (PRP) and known amounts of adenosine triphosphate (ATP). To run the curve, set up the instrument as for an aggregation, then:
1. Add FFE to the reaction cuvette.
2. Establish a baseline reading and then add 1 nM ATP to the cuvette. Repeat this step using 0.5 and 0.25 nM ATP. Each concentration should be run in duplicate.
3. Measure the number of chart units that the lumi-pen deflects (pen deflections) for each concentration, average the values, and plot on standard arithmetic graph paper or use a computer graphics program with the x-axis as mM ATP and the y-axis as chart units.
4. Incubate PRP samples in the absence or presence of various doses of "inhibitor" for 10-60 min at 37° C.
5. After incubation, add the PRP samples and FFE to a reaction cuvette, establish a baseline, and add agonist (collagen, convulxin or collagen-related peptide).
6. Measure chart units on the lumi-channel.
7. Read from the standard curve.

Example 11

Platelet Dense Granule Secretion Measured by $^{14}C$-Serotonin

When the platelets aggregate, the released serotonin feeds back on the platelets to amplify the aggregation process. Serotonin release experiments can be performed demonstrating that the "inhibitor" is effective in inhibiting collagen-induced platelet activation and aggregation.
1. Platelets in plasma are loaded with $^{14}C$-serotonin (2 mCi/ml) in the absence or presence of various doses of "inhibitor" at 37° C. for 1 hr.
2. Platelets are then gel-filtered or washed and the count adjusted to $2.5 \times 10^8$/ml with test buffer.
3. Optionally, 1 mM imipramine is added to inhibit serotonin reuptake.
4. An aliquot of platelet suspension, which will represent 100% total serotonin, is set aside for scintillation counting.
5. After a test has been carried out, such as addition of agonist (collagen, convulxin or collagen-related peptide), a final of 1% formalin and 5 mM EDTA are added, the suspension is centrifuged at 15,000 g for 10 min, and the supernatant is measured for $^{14}C$-serotonin.
6. The percentage of release is determined by the ratio of the measured released serotonin to the total serotonin from an equivalent volume of platelets×100.

Example 12

Alpha-Granule Protein Release

Beta-thromboglobulin (β-TG) and platelet factor 4 (PF4) are specific platelet alpha-granule proteins that are released upon platelet activation. Release of either protein can be measured by ELISA using commercially available kits and used demonstrating that the "inhibitor" is effective in inhibiting collagen-induced platelet activation and aggregation.
1. Platelets may first be measured for aggregation according to Example 9. Subsequently, the aggregated platelets are centrifuged at 400×g for 15 minutes at 4° C.
2. The supernatants are used for subsequent measurements of βTG and PF4.
3. Using commercially available enzyme-linked immunosorbent assay (ELISA) kits according to the manufacturer's instructions (Asserachrom, Diagnostica Stago SA, Asnieres, France) the β-TG and/or PF4 is measured using aliquots of the supernatant.

Example 13

Platelet Adhesion

The injured arterial wall exposes collagen to the blood and recruits platelets to the injured site. In the physiological state, in which shearing has an important role, GPVI is involved in recruitment and subsequent platelet aggregation and thrombi formation. In humans, platelets from GPVI-deficient patients can attach to collagen but nonetheless do not form aggregates.

Platelet adhesion experiments can be performed demonstrating that the "inhibitor" slightly inhibits or does not inhibit adhesion of platelets to immobilized soluble collagen.
1. Microtiter plates are coated with collagen (2.0 mg/well) in 5 mM acetic acid for 1 h at room temperature, followed by addition of 1% bovine serum albumin for 1 h at room temperature to block the nonspecific binding of platelets to the wells.
2. After blocking, wells are washed three times with Hepes-buffered saline, 20 mM HEPES, pH 7.4 containing 0.14 M NaCl and 2 mM $MgCl_2$.
3. Washed platelets ($3.0 \times 10^5$ cells) are incubated in the absence or presence of various doses of "inhibitor" in Tyrode's buffer containing 2 mM $CaCl_2$ and 100 ng/mL $PGE_1$, for 0.5-1 h at room temperature and then transferred into wells.
4. After 45 min incubation, wells are washed three times with HEPES-buffered saline again.
5. The number of platelets adhering to immobilized collagen is determined using Micro BCA Protein Assay Kits (Pierce Biotechnology). The percentage of specifically adherent platelets was calculated on the basis of a standard curve obtained with known numbers of platelets.

Example 14

Phosphorylation of FcRγ Chain of the GPVI-FcRγ Complex

To confirm that the "inhibitor" is a specific inhibitor of collagen-induced platelet aggregation mediated by GPVI, the effect of "inhibitor" on phosphorylation of the FcRγ chain can be easily examined by immunoprecipitation, because binding of GPVI to collagen causes tyrosine phosphorylation of the FcRγ chain, which is coupled to GPVI.

In the absence of "inhibitor", tyrosine phosphorylation of FcRγ chain of platelets stimulated by collagen, convulxin or CRP should be detectable. In contrast, in the presence of "inhibitor" phosphorylation of FcRγ chain should be at least partially absent, or in some cases, completely absent.

1. Washed platelets ($1 \times 10^9$ cells) are incubated in the absence or presence of various doses of "inhibitor" at 37° C. for 30-60 min.
2. After incubation, platelets are stimulated by 10 mg/mL collagen at 37° C. for 10 min and then lysed with an equal volume of ice-cold lysis buffer, 20 mm Tris, 300 mM NaCl, 2 mM EDTA, 2% Nonident P-40, 1% deoxycholate, 0.1% SDS, 1 mM phenylmethylsulfonyl fluoride, 2 mM sodium orthovanadate, 10 mg/mL leupeptin and 10 mg/mL aprotinin.
3. Non-lysed cells and debris are removed by centrifugation.
4. Platelet lysate is incubated with 1 mg/mL anti-FcRγ chain antiserum at 4° C.
5. After overnight incubation, protein A-Sepharose beads are added to the mixture and washed three times with 10 mM Tris, 160 mM NaCl and 0.1% Tween 20.
6. The protein bound to beads is eluted with Laemmli buffer and applied to SDS-PAGE and western blot analysis.

Example 15

Platelet Function Analysis with PFA-100® Analyzer

The PFA-100® (Dade Behring) is an in vitro bench-top platelet function analyzer containing disposable collagen test cartridges (i.e., for example, coated with epinephrine or adenosine diphosphate (ADP)) that stimulate high shear platelet function, platelet adhesion, and platelet aggregation. The presence of the platelet activators and the high shear rates (5000-6000 s$^{-1}$) under the standardized conditions result in platelet adhesion, platelet activation, and platelet aggregation resulting in formation of a platelet plug within an aperture of the analyzer. Platelet function is thus measured as a function of the time it takes to occlude the aperture. The test is simple to perform, rapid (with maximal closure times (CT) of 300 s) and can test relatively small volumes (0.8 mL/cartridge) of citrated blood up to 4 h from sampling.

The PFA-100® is sensitive to many variables that influence platelet function including abnormalities in platelet number, haematocrit, drug and dietary effects, platelet receptor defects, VWF defects, release and granular defects.

Platelet function analysis with the PFA-100® analyzer can be easily performed demonstrating that the "inhibitor" is effective in inhibiting collagen-induced platelet function: adhesion, activation and aggregation. For example, the procedure may be performed as follows:

1. Citrated blood samples are incubated in the absence or presence of various doses of "inhibitor" for 30-60 min at room temperature.
2. After incubation, the sample (~0.8 ml/cartridge) is aspirated under constant negative pressure from the sample reservoir through a capillary and a microscopic aperture (147 mm) cut into a membrane coated with either collagen/epinephrine (CEPI) or collagen/ADP (CADP).
3. Platelet function is measured as a function of the time it takes to occlude the aperture.
4. Results are expressed as "closure time", i.e., the time it takes for the aperture of the cartridge to become congested as a result of blood clotting.
5. The aperture closing time is recorded in seconds.

Example 16

Thrombus Formation Stimulated by Human Atherosclerotic Lessons

Cell-free homogenates from human lesions/plaques promote platelet adhesion and aggregate formation under high-shear flow conditions. Exposure of platelets to procoagulant phosphatidylserine (PS) also results in adhesion and/or aggregation. Blocking of the glycoprotein VI (GPVI) collagen receptor may abolish this lesion/plaque homogenate and/or PS induced platelet aggregation.

Thrombus formation stimulated by human atherosclerotic lessons (atheromatous plaques), as well as exposure of procoagulant phosphatidylserine (PS) on platelets can be used as an in vitro system to demonstrate efficacy and specificity of a GPVI "inhibitor".

Preparation of Plaque Tissues

1. Atherosclerotic plaques are collected at autopsy from carotid artery and used in compliance with institutional guidelines and medical ethics committee regulations.
2. After resection, the atherosclerotic specimens are divided into adjacent parts of 5 mm for histological analysis or experimental use.
3. Specimens for histology are fixed in formalin (10% in PBS), routinely processed and embedded in paraffin.
4. Sections of 4 mm are cut, stained with hematoxylin and eosin, and classified for type of lesion according to the morphological criteria.
5. Other sections are stained for collagen types I and III or tissue factor (TF). Thereafter, they are deparaffinized in xylene and rehydrated in ethanol. For collagen I and III staining, this is followed by 15-min treatment with methanol plus 1% hydrogen peroxide to block endogenous peroxidase activity.
6. Sections are incubated for 30 min at room temperature with antibody against collagen I (1:10) or collagen III (1:10), or overnight at 4° C. with anti-TF antibody.
7. After a wash using Tris-buffered saline (TBS; in: NaCl 136.9 mM, Trizma® base 5.0 mM, 1% BSA and 0.1% Tween®, pH 7.6), sections are treated with secondary biotin-labeled antibody (1:1000 for 30 min) for collagen types I and III, or with secondary poly-AP for TF, and again washed in TBS.
8. Streptavidin-biotin complex with horseradish peroxidase (streptavidin-ABC-HRP) (1:500) is incubated for 30 min, and diaminobenzidine (DAB) is added for chromogenic development of collagen I and III staining.
9. TF is visualized with an alkaline phosphatase substrate kit.

10. Serial sections treated with secondary antibodies alone do not show staining (control).
11. Total collagen content of plaque material is determined by staining sections with 0.1% Sirius red in saturated picric acid for 90 min.
12. Plaque parts destined for experimental use are immediately frozen into liquid nitrogen and stored at −80° C.
13. After thawing tissues are homogenized in PBS pH 7.4 using a potter.
14. The homogenates are centrifuged three times at 2240 g for 10 min.
15. Pellets are resuspended in sterile saline at a concentration of 160 mg tissue wet weight/ml.

Example 17

Flow Measurement of Thrombus Formation Using Phosphatidylserine

1. Flow experiments over collagen are performed at room temperature using PPACK-anticoagulated blood.
2. Collagen (35 mg/cm$^2$) or plaque materials (170 mg wet weight/cm$^2$) are spread on cleaned glass coverslips.
3. Coverslips are blocked with HEPES buffer pH 7.45, (NaCl 136 mM, glucose 10 mM, HEPES 5 mM, KCl 2.7 mM, MgCl$_2$ 2 mM, CaCl$_2$ 2 mM, and 1% BSA), and kept wet.
4. Blood samples are incubated in the absence or presence of various doses of "inhibitor" for 10-60 min at room temperature.
5. Blood is perfused over coated coverslips through a transparent, parallel-plate perfusion chamber at a moderately highwall-shear rate of 1000 s$^{-1}$ for 4 min.
6. High-resolution transmission and fluorescent images are recorded in real-time with two different cameras equipped with a Visitech® digital imaging system (Sunderland, UK).
7. PS exposing platelets are detected by post-perfusion with HEPES buffer pH 7.45 containing 1 U/ml heparin and 0.5 mg/ml OG488-annexin A5.
8. Phase-contrast and fluorescent images are captured from at least ten different plaque/collagen-containing microscopic fields, which are arbitrarily chosen.
9. Images with background fluorescence that is not attributed to platelets are excluded from analysis.
10. Area coverage from phase-contrast and fluorescent images is analyzed off-line.

Example 18

Thrombin Generation Measurement

1. Platelet Rich Plasma (PRP) samples are incubated in the absence or presence of various doses of "inhibitor" for 10-60 min at 37° C.
2. Thrombin generation is continuously measured in PRP with a well-plate reader (Molecular Devices, Sunnyvale, Calif., USA) using the thrombogram method.
3. Final assay concentrations are: 1 pmol/l TF, 66% plasma with 1.0×10$^8$ platelets/mL and 2.5 mM Z-Gly-Gly-Arg aminomethyl coumarin (Z-GGR-AMC).
4. First-derivative curves of accumulation of fluorescence are converted into curves of nanomolar thrombin using human thrombin calibrator and thrombinoscope software.
5. Thrombin generation measurements are started at 10 min after addition of collagen or plaque material.

6. Collagen samples are dialyzed against 10 mM acetic acid (overnight 4° C.) before use.
7. Plaque material, dissolved in saline, is added at 0.28 mg wet weight/ml.
8. Controls are run with vehicle media.
9. TF activity is determined in homogenates that are diluted in 25 mM HEPES and 175 mM NaCl (pH 7.7) and incubated at 37° C. for 20 min.
10. Reactions are started by addition of factor VIIa (0.72 nM, f.c.), factor X (60 nM), CaCl$_2$ (3 mM) and phospholipid vesicles (7.2 mM, phosphatidylcholine (PC):PS, 80:20).
11. Factor Xa activity is kinetically measured using the chromogenic substrate S2765.

Example 19

The Cone and Plate(let) Analyzer (CPA)

The cone and plate(let) analyzer (CPA) tests platelet function under close-to-physiological conditions. This method is based upon the adhesion of platelets to the extracellular matrix (ECM) using whole blood exposed to high shear. The original CPA system tests whole blood platelet adhesion and aggregation on an ECM-coated plate, under physiological arterial flow conditions. The ECM-coated plates can be replaced by simple polystyrene (PS) plates, with no coating additives.

Platelet function experiments using the CPA system can be performed demonstrating that the "inhibitor" is effective in inhibiting platelet aggregation.

1. A 200-mL aliquot of whole blood in a sodium citrate 0.38% solution (or another anticoagulant such as heparin 2.5 U/mL) is incubated in the absence or presence of various doses of "inhibitor" for 10-60 min at room temperature.
2. After incubation, the 200-mL citrated blood sample is placed on ECM and a defined shear rate is applied for 2 minutes using a cone and plate device.
3. This is followed by staining and measuring the percentage of ECM surface covered (SC) by the stained objects and the average size (AS) of the objects using an image analyzer.
4. Under these test conditions only platelets, but not other blood cells, adhere to the ECM.
5. When normal blood is analyzed, platelet deposition is a shear and time dependent process, reaching maximal levels within 2 minutes at high shear rate (1300 s$^{-1}$), of about 20% SC and 40-50 mm$^2$ AS. These two parameters are positively correlated with platelet count and hematocrit, demonstrating the important role of red blood cells (RBCs) in primary hemostasis.

Example 20

Flow Cytometry Platelet Function Experiments

Flow cytometry, a remarkably versatile tool for the study of platelet function, encompasses multiple assays for multiple purposes, as listed in Table 3 below.

TABLE 3

Platelet function tests measured by flow cytometry.

| Flow cytometric platelet function test | Examples |
|---|---|
| Diagnosis of platelet disorders | Glanzmann's thrombasthenia, Bernard Soulier syndrome, Storage Pool Disease, HIT, Scott syndrome |
| Quantification of receptor density | Platelet receptor defects, Influence of receptor polymorphisms |
| Detection of activated platelets | CD62p, CD63, CD40L, Gp IIb/IIIa conformation, PS exposure, platelet-leukocyte conjugates, microparticles, platelet aggregates |
| Monitoring platelet responses to agonists | Using classical agonists in combination with activation markers |
| Monitoring anti-platelet drugs | GpIIb/IIIa antagonists, Clopidogrel, aspirin |
| Platelet production in thrombocytopenia | Reticulated platelets |
| Accurate platelet counting | New reference method - PLT/RBC ratio |
| Platelet associated IgG | Immune thrombocytopenia detection of alloantibodies |
| Platelet survival | Biotinylation studies |
| Signal transduction | Calcium measurement intracellular phosphorylation |

Flow cytometry platelet function tests can be performed demonstrating that the "inhibitor" is effective in inhibiting collagen-induced platelet activation and aggregation. Different platelet activation-dependent monoclonal antibodies, i.e. antibodies that bind to activated, but not resting, platelets can be used in these tests. See, Table 4.

TABLE 4

Platelet Activation-Dependent Monoclonal Antibodies

| Activation-Dependent Platelet Surface Change | Prototypic Antibodies |
|---|---|
| Conformational changes in integrin aIIbb3 | |
| Activation-induced conformational change in $a_{IIb}\beta_3$ resulting in exposure of the fibrinogen binding site* | PAC1 |
| Ligand-induced conformational change in $a_{IIb}\beta_3$ | PM 1.1, LIBS1, LIBS6 |
| Receptor-induced conformational change in bound ligand (fibrinogen) | 2G5, 9F9, F26 |
| Exposure of granule membrane proteins | |
| P-selectin (a-granules)* | S12, AC1.2, 1E3 |
| CD63 (lysosomes) | CLB-gran/12 |
| LAMP-1 (lysosomes) | H5G11 |
| LAMP-2 (lysosomes) | H4B4 |
| CD40L | TRAP1 |
| Lectin-like oxidized LDL receptor-1 (LOX-1) | JTX68 |
| Platelet surface binding of secreted platelet proteins | |
| Thrombospondin | P8, TSP-1 |
| Multimerin | JS-1 |
| Development of a procoagulant surface** | |
| Factor V/Va binding | V237 |
| Factor X/Xa binding | 5224 |
| Factor VIII binding | 1B3 |

*Monoclonal antibodies directed against the fibrinogen binding site exposed by a conformational change in $a_{IIb}\beta_3$ of activated platelets, PAC1, and against granule membrane protein, P-selectin-specific antibodies, were successfully used to demonstrate that the GPVI core peptide is effective in inhibiting collagen-induced platelet activation and aggregation (See Examples).
**Development of a procoagulant platelet surface can also be detected by the binding of annexin V to phosphatidylserine.

A typical scheme of sample preparation for analysis of platelets by whole blood flow cytometry includes:

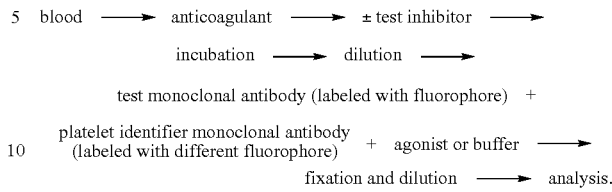

Platelet rich plasma (PRP) as well as isolated washed platelets can also be used in flow cytometry experiments.
P-Selectin
 1. Blood samples, 1 hour after venipuncture, are incubated in the absence or presence of various doses of "inhibitor" for 10-60 min at room temperature.
 2. After incubation, samples are diluted 1 in 8 with phosphate buffered saline (PBS) and stimulated with 10.0 mg/mL collagen, 4-8 nM convulxin, or 0.2 mg/mL CRP as platelet activators.
 3. After stimulation, samples are incubated with phycoerythrin conjugated CD62P antibody (anti-CD62PPE) (Becton Dickinson, Oxford, UK (BD)) and fluorescein isothiocyanate conjugated CD61 antibody (anti-GPIIIa-FITC) (BD) for 15 min at room temperature.
 4. Samples are fixed using CellFIX® (BD) and analysed using a BD FACScan® flow cytometer and the CellQuest® software program for data acquisition and analysis.
 5. Usually, the flow cytometer is calibrated weekly using Calibrite® beads in conjunction with FACScomp® software (BD).
 6. An isotype matched control (BD) for nonspecific binding is prepared for each subject. It is used to set the marker positions on the dot plots for each sample.
 7. CD61 positive events are identified and gated (R1) using FL1 vs. FL2.
 8. R1 is then applied to the forward vs. side scatter dot plot to allow identification and gating (R2) of the platelet population.
 9. R2 is then applied to FL1 vs. FL2 containing the marker positions that are set using the isotype matched control.
 10. CD62P positive populations are identified by fluorescence.
 11. 100,000 total events are analyzed per sample, and the percentage of CD62P positive (% CD62P+) platelets and the geometric mean channel fluorescence (MCF) of the CD62P positive platelets are quantified.

Example 21

Folts Model of Cyclic Platelet-Dependent Thrombosis for Evaluating Anti-Platelet Agents The Folts anti-platelet model evaluates the in vivo antithrombotic properties of pharmacologic agents that inhibit in vitro platelet function. In this model, blood flow in the circumflex artery of dogs is measured continuously using a flow meter probe. A plastic cylinder is placed around the vessel, producing approximately 70% stenosis, and intimal damage is induced by compressing the artery. Blood flow falls to zero as platelets accumulate to produce an occlusive thrombus. Depending on the degree of stenosis and extent of intimal damage, the thrombus will dislodge either spontaneously or by shaking the constrictor, temporarily restoring flow until platelets re-accumulate again to occlude the vessel. These cyclic flow reductions (CFRs) are repetitive and unchanging over hours, permitting the testing of one or more doses of antithrombotic agents, using each animal as its own internal control. Detailed technical protocols for this method using coronary or carotid arteries in dogs, pigs, monkeys, and rabbits have been published elsewhere and are available to those having ordinary skill in the art.

The Folts model of cyclic platelet-dependent thrombosis can be used to demonstrate that the "inhibitor" is effective in abolishing CFRs and inhibiting coronary thrombosis. Zoldhelyi et al., "Inhibition of coronary thrombosis and local inflammation by a noncarbohydrate selectin inhibitor" *Am J Physiol Heart Circ Physiol* 279:H3065-75 (2000)(herein incorporated by reference in its entirety).

Example 22

Stent-Based Delivery of a GPVI Inhibitor

Interventions such as endovascular stents, which increase vascular lumen size above that achieved with balloon angioplasty have frequent thrombotic and restenotic side effects. The porcine coronary models using injuries caused by stenting are now accepted standards by which potential restenosis therapies are studied, in large part because the stages of neointimal growth described in the porcine model follow those now known in humans. See, Table 5.

TABLE 5

Time Course Comparison: Porcine versus Human Coronary Stenting

| | Porcine Coronary Model | Human Stent Implantation |
|---|---|---|
| Thrombus | 0-14 days | 0-30 days |
| Inflammation | 1-14 days | 0-30 days |
| Endothelialization and granulation tissue | 4-16 days | 14-90 days |
| Smooth muscle cells and matrix formation | 14-28 days | 2-6 months |

The vascular response to "inhibitor"-coated steel stents can be evaluated in porcine animal model demonstrating that the "inhibitor" is effective in reducing thrombosis and restenosis after stenting.

Polymeric systems used to delivery drugs include, but are not limited to:

1) a thin layer of a poly-n-butyl methacrylate and polyethylene-vinyl acetate copolymer to immobilize drug for following elution (See, Protocol 1);

2) the BiodivYsio® (Biocompatibles, U.K.) DD phosphorycholine (PC) stent system is a balloon-expandable 316 L stainless steel stent coated with a PC polymer. Phosphorycholine is expressed naturally in over 90% of the outer red cell membrane lipid bilayers and therefore confers hemocompatibility. The polymer can also act as drug reservoir and is capable of controlled release (See, Protocol 2).

Recently, this system was successfully used to deliver angiopeptin, a synthetic cyclic octapeptide analogue of somatostatin, a naturally occurring human hormone.

Protocol 1:
1. Stainless steel balloon-expandable tubular stents (Cordis Co), 18 mm long, are coated with a thin layer of a poly-n-butyl methacrylate and polyethylene-vinyl acetate copolymer containing the relevant amount of the "inhibitor".
2. The total drug and polymer weight as well as ratio of "inhibitor" to polymer are determined based on the results of pharmacokinetics studies.
3. All stents are individually packaged, coded with a serial number on the packaging label, and sterilized with ethylene oxide.

Protocol 2:
1. Solution of "inhibitor" in an appropriate solvent (aqueous solutions, ethanol, DMSO, etc.) are prepared and filtered through a 0.22 nm filter into a 1 ml syringe.
2. The BiodivYsio® DD PC-coated stent is then immersed in the "inhibitor" solution for 5 min and then dried at room temperature for 5 min. The low-dose stent is then ready for implantation.
3. Using a microliter pipette, additional amount of "inhibitor" solution is applied directly onto the stent and dried for 10 min, giving a loading of high dose of "inhibitor" per stent. Exact dosages are chosen and optimized depending on the feasibility of loading these amounts onto the stents. The amount of drug that could be loaded onto the stent is dependent on the concentration of the drug solution.

Example 23

In vivo Pharmacokinetics of "Inhibitor"-Coated Stents

1. Stents are coated with "inhibitor" (Protocol 1 or 2 according to Example 22) and mounted on 3.5-mm-diameter angioplasty balloons.
2. The stents are deployed in the coronary arteries of pigs (1 stent per pig) in the left anterior descending, proximal, or distal left circumflex coronary artery. The guiding catheter is used as a reference to obtain a 1.2:1 to 1.4:1 stent-to-artery ratio compared with the baseline vessel diameter.
3. Blood samples are obtained at 10 minutes; 1, 6, 24, and 48 hours; and 3, 30, 60, 90 and 180 days to determine systemic "inhibitor" levels.
4. The animals are euthanized and vessels harvested at 180 days after stent implantation.
5. Stents are removed from freshly isolated arterial segments, and all tissue is frozen in liquid nitrogen.
6. "Inhibitor" levels in whole blood, arterial wall, and the stent are determined by high-performance liquid chromatography.

Example 24

Efficacy of "Inhibitor"-Coated Stents

1. Juvenile swine (25 to 35 kg) are underwent placement of "inhibitor"-coated and control, non-coated stents in the left anterior descending, circumflex, or right coronary artery.
2. The guiding catheter is used as a reference to obtain a 1.2:1 to 1.4:1 stent-to-artery ratio compared with the baseline vessel diameter.
3. Animals are allowed to recover and are returned to care facilities, where they receive a normal diet.
4. Arteriotomy of the left femoral artery is performed, and a 7-F sheath is introduced for control angiography of the right and left coronary vessels.

5. Next, an intravascular ultrasound (IVUS) catheter is introduced into the treated left coronary arteries for image capture using an automatic pullback device at a speed of 0.5 mm/s.
6. IVUS images are recorded on s-VHS videotapes for offline qualitative and quantitative analyses.
7. Subsequently, the animals are sacrificed at 3, 30, 90 and 180 days with 40 mL of saturated KCl plus 40 mL of thiopental after completion of coronary angiography and IVUS imaging for quantitative analysis.
8. The hearts are explanted, and the coronary arteries are flushed with approximately 300 mL of saline before pressure fixation in situ (about 100 to 110 mmHg) with 500 mL of 7.5% buffered formaldehyde.
9. The coronary arteries are then dissected from the epicardial surface.
10. The distal edge of the stented artery is labeled, and the entire specimen is fixed in 2% buffered formalin for 24 hours, embedded in Technovit 9100 (Heraeus-Kulzer, Armonk, N.Y., USA), and cut with a hard metal knife (Leica Microsystems GmbH, Vienna, Austria) to obtain 4 to 6-mm sections representing a single cell layer.

Example 25

Macroscopic Evaluation of Neointimal Proliferation

1. All IVUS records made in accordance with Example 24 are analyzed in offline mode with a computer-based IVUS analysis system (EchoPlaque 2®; INDEC Systems Inc., Mountain View, Calif., USA).
2. After 3-dimensional (3D) reconstruction of the vessel, volume measurements are made automatically within the stented part of the artery.
3. The lumen volume is defined as the volume within the stent limited by the endothelium.
4. The vessel volume is that limited by the external elastic membrane, and the stent volume as the volume confined by the stent struts.
5. The neointimal volume is the stent volume minus the lumen volume, and the outward plaque volume is the vessel volume minus the stent volume.
6. The net volume obstruction is calculated as the intimal volume divided by the stent volume.

Example 26

Histological Examinations

1. Sections from the most diseased stent segments determined by IVUS (in accordance with Example 24) and from the adjacent proximal and distal vessel are stained with hematoxylin-eosin and van Gieson elastin stains.
2. Qualitative histopathological parameters, such as fibrin deposition around the stent struts, necrosis, inflammation, injury score, and the degree of re-endothelialization, are evaluated on a scoring system ranging from 0 (minimal) to 3 (maximal).
3. Histomorphometric parameters, such as lumen area, neointimal area (within the internal elastic lamina [IEL]), the maximal percentage area stenosis (intimal area/stent area), the outward plaque area (between the stent struts and the external elastic lamina [EEL]), and the EEL area (inside the EEL) are recorded for each section.

Tissue Factor Staining:

1. Eight-mm sections from the proximal, middle, and distal part of the stent are cut from the coronary artery specimens.
2. The Technovit is removed by incubation with xylol for 40 minutes and 2-mercaptoethylamine (2-MEA) for 20 minutes.
3. Sections are fixed with cold acetone (48° C.). To inhibit endogenous peroxidase (POX), POX blockade is performed with periodic acid.
4. After incubation with normal goat serum (dilution 1:100; Dako, Glostrup, Denmark), a polyclonal anti-tissue factor (TF) antibody (R&D Systems, Minneapolis, Minn., USA) at a concentration of 10 mg/mL is added, and the sections are incubated for 1 hour at room temperature.
5. Thereafter, a biotinylated antibody (dilution 1:100; Dako) is added for 1 hour.
6. After rinsing with phosphate buffered saline (PBS), the sections are incubated with a streptavidin-POX complex (dilution 1:100; Dako) for 30 minutes at room temperature.
7. TF is visualized by addition of DAB (diaminobenzidine; Dako) for 20 minutes.
8. Counterstaining is performed with hematoxylin.

Example 27

Scanning Electron Microscopy

1. Parts of the stented arteries from pigs that experience acute stent thrombosis are fixed at room temperature in 2% glutaraldehyde in 0.1 M sodium cacodylate buffer to which 0.1 M sucrose is added with 3 mM $CaCl_2$ (pH 7.4).
2. After fixation, the arteries are rinsed and stored in 0.15 M sodium cacodylate buffer supplemented with 3 mM $CaCl_2$ (pH 7.4) in a refrigerator until further processing.
3. The arteries are mounted on an aluminum stub and coated with 15-nm-thick platinum (Polaron, Watford, UK). The specimens are analyzed in a scanning electron microscope, and the digital images are captured.

Example 28

Preparation of Small Unilamellar Vesicles

Model membranes composed of zwitterionic and anionic phospholipids and their mixtures in proportion similar to that found in vertebrate cell membranes are produced.
1. Dimyristoyl-L-α-phosphatidylcholine (DMPC) and dimyristoyl-L-α-phosphatidyl-DL-glycerol (DMPG) are dissolved in dry chloroform and chloroform/methanol (2:1), respectively, to give 10 mg/ml solutions.
2. These are evaporated under reduced pressure and the resulting lipid films are vacuum-dried overnight.
3. Lipids are hydrated by resuspending in HEPES buffer for 60 min at 34° C. to give 0.5 mM concentration in respect of phospholipids.
4. The solution is sonicated in an ultrasonic bath for 20 min.
5. Eight cycles of freeze/thawing are followed by extrusion through polycarbonate filters, first 100 nm (21 times), then 50-nm pore diameters (21 times), using a Lipofast apparatus (Avestin, Ottawa, Canada) and the small unilamellar vesicles (SUVs) are used immediately.

Example 29

Surface Plasmon Resonance (SPR) Analysis of Lipid Binding Activity

1. SPR is carried out on a BIAcore® 2000 instrument using Pioneer Sensor Chip L1 and HEPES (HBS-N, Biacore) as running buffer.
2. The chip surface is cleaned with 40 mM octyl glycoside (30 mL, 10 mL/min) followed by running buffer (100 mL, 10 mL/min).
3. Liposomes (small unilamellar vesicles, SUVs), made in accordance to Example 28, are injected (100 mL, 5 mL/min) giving a response of about 8000 RU.
4. 10 mM NaOH (40 mL, 10 mL/min) removes any multilamellar vesicles from the surface that is followed by 10 mM glycine, pH 2.2 (10 mL, 10 mL/min), before injecting a peptide or peptide analogue inhibitor (100 mL, 5 mL/min), such as one exemplified in Table 5.
5. After peptide injection the dissociation stage is 1200 s.
6. Regeneration of the sensor chip is achieved with 40 mM octyl glycoside (30 mL, 10 mL/min).
7. All SPR experiments are run at 25° C. and all analyses are performed using BIAevaluation software (Biacore).
8. For the comparative binding of a peptide and/or peptide analogue, a determination of percentage binding is expressed as a percentage of the wild-type peptide binding.
9. The values are representative of three injections under identical conditions for each peptide.
10. To study the effect of interaction time on the wild-type peptide binding the "variable contact times" injection command is utilized on the Biacore® 2000 instrument. This is achieved by switching additional flow cells into the flow path as the injection proceeds; thus the injections end at the same time.

Example 30

Preparation of Sucrose-Loaded Vesicles

This example describes the preparation of sucrose-loaded large unilamellar vesicles for use in a sucrose-loaded vesicle binding assay.
1. The corresponding lipid, the zwitterionic lipid 1-palmitoyl-2-oleoyl-sn-glycero-3-phosphocholine (POPC) or the acidic lipid 1-palmitoyl-2-oleoyl-sn-glycero-3-phosphoglycerol (POPG), or lipid mixtures in $CHCl_3$ are evaporated under argon and then vacuum-dried for 3 h at 20° C.
2. The dried lipid is resuspended in 176 mM sucrose and 1 mM MOPS at pH 7.0; the air is displaced with argon.
3. LUVs are made after five freeze-thaw cycles by extruding multilamellar vesicles 10 times through a stack of two polycarbonate filters (100-nm pore diameter) in an Avanti mini-extruder (Avanti Polar Lipids, Alabaster, Ala.).
4. The vesicle solution is diluted 5 times with 1 mM MOPS buffer, pH 7.0, containing 0.1 M KCl and osmotic to the internal sucrose buffer, and centrifuged at 100,000 g for 1 h at 25° C. using a table-top Beckman TL-100 ultracentrifuge equipped with a TLA-45 rotor.
5. The supernatant is removed, and the lipid pellet is resuspended in the same buffer solution.
6. The final concentration of the vesicle solution was determined using a phosphorous assay.

Example 31

Sucrose-Loaded Vesicle Binding Assay

1. In the membrane-binding assay, peptide or peptide analogue in a final concentration of 10 mM is mixed with the sucrose-loaded LUVs; [peptide]<<[lipid] so that the peptide does not bind a significant fraction of the lipid.
2. After 15 min of equilibration at room temperature (20° C.), vesicle-bound peptide or peptide analogue is separated by centrifugation (for 1 h at 100,000 g and 25° C.).
3. Ninety percent of the supernatant and pellet is evaluated for protein content using a fluorescamine assay.
4. The percentage of the protein bound at a given lipid concentration is calculated and corrected for the 1-3% lipid that remains in the supernatant.

Example 32

Circular Dicroism Spectroscopy Analysis of a Peptide Secondary Structure

1. Far-UV CD spectra are recorded on an Aviv 202 spectropolarimeter (AVIV Instruments, Lakewood, N.J.) with 0.01 mM peptide or peptide analogue in the absence or presence of SDS and/or lipids, or helicity inducers, such as TFE, in phosphate buffered saline buffer (PBS; 137 mM NaCl, 10 mM sodium phosphate, 2.7 mM KCl, pH 7.4) in 1.0 mm path-length cells.
2. Data are collected at 25° C. every nanometer from 260 to 190 nm with 1.0 s averaging per point and a 1 nm bandwidth.
3. The CD spectra of at least six scans are signal averaged, baseline corrected by subtracting an averaged buffer spectrum, and normalized to molar residue ellipticity.

References
1. Manolios, N. et al. (1990) Transmembrane helical interactions and the assembly of the T cell receptor complex. Science 249, 274-277.
2. Call, M. E. et al. (2002) The organizing principle in the formation of the T cell receptor-CD3 complex. Cell 111, 967-979.
3. Michnoff, C. H. et al. (1994) Mutations within the NH2-terminal transmembrane domain of membrane immunoglobulin (Ig) M alters Iga and Igb association and signal transduction. J. Biol. Chem. 269, 24237-24244.
4. Daeron, M. (1997) Fc receptor biology. Annu. Rev. Immunol. 15, 203-234.
5. Borrego, F. et al. (2002) Structure and function of major histocompatibility complex (MHC) class I specific receptors expressed on human natural killer (NK) cells. Mol. Immunol. 38, 637-660.
6. Biassoni, R. et al. (2000) Human natural killer cell activating receptors. Mol. Immunol. 37, 1015-1024.
7. Moroi, M. and Jung, S. M. (2004) Platelet glycoprotein VI: its structure and function. Thromb. Res. 114, 221-233.
8. Sigalov, A. et al. (2004) Homooligomerization of the cytoplasmic domain of the T cell receptor z chain and of other proteins containing the immunoreceptor tyrosine-based activation motif. Biochemistry 43, 2049-2061.
9. Sigalov, A. B. (2004) Multichain immune recognition receptor signaling: different players, same game? Trends Immunol. 25, 583-589.
10. Sigalov, A. (2005) Multi-chain immune recognition receptors: spatial organization and signal transduction. Semin. Immunol. 17, 51-64.

11. Arkin, M. (2005) Protein-protein interactions and cancer: small molecules going in for the kill. Curr. Opin. Chem. Biol. 9, 317-324.
12. Pecht, I. et al. (1991) Rotational dynamics of the Fce receptor on mast cells monitored by specific monoclonal antibodies and IgE. Biochemistry 30, 3450-3458.
13. Rudolph, M. G. and Wilson, I. A. (2002) The specificity of TCR/pMHC interaction. Curr. Opin. Immunol. 14, 52-65.
14. Posner, R. G. et al. (2004) Interaction of a monoclonal IgE-specific antibody with cell-surface IgE-FceRI: characterization of equilibrium binding and secretory response. Biochemistry 43, 11352-11360.
15. Patrick, S. M. et al. (2000) Dependence of T cell activation on area of contact and density of a ligand-coated surface. J. Immunol. Methods 241, 97-108.
16. Pitcher, L. A. et al. (2005) The CD3 ge/de signaling module provides normal T cell functions in the absence of the TCR z immunoreceptor tyrosine-based activation motifs. Eur. J. Immunol. 35, 3643-3654.
17. Wilson, B. S. et al. (1995) Distinct functions of the FceR1 g and b subunits in the control of FceR1-mediated tyrosine kinase activation and signaling responses in RBL-2H3 mast cells. J. Biol. Chem. 270, 4013-4022
18. La Gruta, N. L. et al. (2004) Architectural changes in the TCR:CD3 complex induced by MHC:peptide ligation. J. Immunol. 172, 3662-3669.
19. Kim, J. H. et al. (2005) Independent trafficking of Ig-a/Ig-b and m-heavy chain is facilitated by dissociation of the B cell antigen receptor complex. J. Immunol. 175, 147-154.
20. Asai, K. et al. (2000) Distinct aggregation of b- and g-chains of the highaffinity IgE receptor on cross-linking. J. Histochem. Cytochem. 48, 1705-1716
21. Risueno, R. M. et al. (2005) Ligand-induced conformational change in the T-cell receptor associated with productive immune synapses. Blood 106, 601-608
22. Dustin, M. L. (2005) A dynamic view of the immunological synapse. Semin. Immunol. 17, 400-410.
23. Krummel, M. F. et al. (2000) Differential clustering of CD4 and CD3z during T cell recognition. Science 289, 1349-1352.
24. Quintana, F. J. et al. (2005) HIV-1 fusion peptide targets the TCR and inhibits antigen-specific T cell activation. J. Clin. Invest. 115, 2149-2158.
25. Wang, X. M. et al. (2002) T-cell antigen receptor peptides inhibit signal transduction within the membrane bilayer. Clin. Immunol. 105, 199-207.
26. Yamasaki, S. et al. (2006) Mechanistic basis of pre-T cell receptormediated autonomous signaling critical for thymocyte development. Nat. Immunol. 7, 67-75.
27. Draberova, L. et al. (2004) Signaling assemblies formed in mast cells activated via Fce receptor I dimers. Eur. J. Immunol. 34, 2209-2219.
28. Loregian, A. and Palu, G. (2005) Disruption of protein-protein interactions: towards new targets for chemotherapy. J. Cell. Physiol. 204, 750-762.
29. Enk, A. H. and Knop, J. (2000) T cell receptor mimic peptides and their potential application in T-cell-mediated disease. Int. Arch. Allergy Immunol. 123, 275-281.
30. Ali, M. et al. (2005) Hydrophobic transmembrane-peptide lipid conjugations enhance membrane binding and functional activity in T-cells. Bioconjug. Chem. 16, 1556-1563.
31. Amon, M. A. et al. Lipidation and glycosylation of a T cell antigen receptor (TCR) transmembrane hydrophobic peptide dramatically enhances in vitro and in vivo function. Biochim. Biophys. Acta. 1763:879-888 (2006).
32. Bennasroune, A. et al. (2004) Transmembrane peptides as inhibitors of ErbB receptor signaling. Mol. Biol. Cell 15, 3464-3474.
33. Siegel, R. M. et al. (2004) SPOTS: signaling protein oligomeric transduction structures are early mediators of death receptor-induced apoptosis at the plasma membrane. J. Cell Biol. 167, 735-744.
34. van Praag, R. M. et al. (2001) OKT3 and IL-2 treatment for purging of the latent HIV-1 reservoir in vivo results in selective long-lasting CD4+ T cell depletion. J. Clin. Immunol. 21, 218-226.
35. Schrager, J. A. and Marsh, J. W. (1999) HIV-1 Nef increases T cell activation in a stimulus-dependent manner. Proc. Natl. Acad. Sci. U.S.A. 96, 8167-8172
36. Keppler, O. T. et al. (2006) Modulation of specific surface receptors and activation sensitization in primary resting CD4+ T lymphocytes by the Nef protein of HIV-1. J. Leukoc. Biol. 79, 616-627.
37. Simmons, A. et al. (2001) Nef triggers a transcriptional program in T cells imitating single-signal T cell activation and inducing HIV virulence mediators. Immunity 14, 763-777.
38. Swigut, T. et al. (2003) Cooperative interactions of simian immunodeficiency virus Nef, AP-2, and CD3-z mediate the selective induction of T-cell receptor-CD3 endocytosis. J. Virol. 77, 8116-8126.
39. Schamel, W. W. et al. (2005) Coexistence of multivalent and monovalent TCRs explains high sensitivity and wide range of response. J. Exp. Med. 202, 493-503.

I claim:

1. A peptide comprising an amino acid sequence consisting of G-N-L-V-R-I-$X_1$-$X_2$-$X_3$-A-$X_4$-$X_5$-$X_6$-$X_7$-I (SEQ ID NO:1), wherein $X_1$ is selected from the group consisting of C, L or G; $X_2$ is selected from the group consisting of L or A; $X_3$ is selected from the group consisting of G or R; $X_4$ is selected from the group consisting of V or I; $X_5$ is selected from the group consisting of I, L or R; $X_6$ is selected from the group consisting of I or L; and $X_7$ is selected from the group consisting of I or L and further comprising an N-terminal sugar conjugate and a C-terminal lipid conjugate wherein said sugar conjugate is 1-amino-glucose succinate and said lipid conjugate is selected from the group consisting of Gly-Tris-monopalmitate, Gly-Tris-dipalmitate, Gly-Tris-tripalmitate, 2-aminododecanoate, and myristoylate conjugates.

2. The peptide of claim 1, wherein said amino acid sequence further comprises at least one amino acid selected from the group consisting of an L-amino acid and a D-amino acid.

* * * * *

SEQUENCE LISTING

<160> NUMBER OF SEQ ID NOS: 34

<210> SEQ ID NO 1
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: X can be Cys, Leu, or Gly.
<220> FEATURE:
<221> NAME/KEY: MISC_FEATURE
<222> LOCATION: (8)..(8)
<223> OTHER INFORMATION: X can be Leu or Ala.
<220> FEATURE:

```
<221> NAME/KEY: MISC_FEATURE
<222> LOCATION: (9)..(9)
<223> OTHER INFORMATION: X can be Gly or Arg.
<220> FEATURE:
<221> NAME/KEY: MISC_FEATURE
<222> LOCATION: (11)..(11)
<223> OTHER INFORMATION: X can be Val or Ile.
<220> FEATURE:
<221> NAME/KEY: MISC_FEATURE
<222> LOCATION: (12)..(12)
<223> OTHER INFORMATION: X can be Ile, Leu, or Arg.
<220> FEATURE:
<221> NAME/KEY: MISC_FEATURE
<222> LOCATION: (13)..(13)
<223> OTHER INFORMATION: X can be Ile or Leu.
<220> FEATURE:
<221> NAME/KEY: MISC_FEATURE
<222> LOCATION: (14)..(14)
<223> OTHER INFORMATION: X can be Ile or Leu.

<400> SEQUENCE: 1

Gly Asn Leu Val Arg Ile Xaa Xaa Xaa Ala Xaa Xaa Xaa Xaa Ile
1               5                   10                  15

<210> SEQ ID NO 2
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X may be Gly or may be missing.
<220> FEATURE:
<221> NAME/KEY: MISC_FEATURE
<222> LOCATION: (2)..(5)
<223> OTHER INFORMATION: X may be Lys or Arg or may be missing.
<220> FEATURE:
<221> NAME/KEY: MISC_FEATURE
<222> LOCATION: (20)..(22)
<223> OTHER INFORMATION: X may be Lys or Arg or may be missing.

<400> SEQUENCE: 2

Xaa Xaa Xaa Xaa Xaa Tyr Ala Arg Ala Leu Leu Tyr Gly Leu Arg Ala
1               5                   10                  15

Val Gly Tyr Xaa Xaa Xaa
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X may be Gly or may be missing.
<220> FEATURE:
<221> NAME/KEY: MISC_FEATURE
<222> LOCATION: (2)..(4)
<223> OTHER INFORMATION: X may be Lys or Arg or may be missing.
<220> FEATURE:
<221> NAME/KEY: MISC_FEATURE
<222> LOCATION: (21)..(22)
<223> OTHER INFORMATION: X may be Lys or Arg or may be missing.

<400> SEQUENCE: 3

Xaa Xaa Xaa Xaa Gly Leu Val Lys Ile Leu Leu Arg Ile Leu Arg Val
1               5                   10                  15

Leu Leu Pro Gly Xaa Xaa
            20
```

```
<210> SEQ ID NO 4
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: X may be Lys or Arg or may be missing.
<220> FEATURE:
<221> NAME/KEY: MISC_FEATURE
<222> LOCATION: (14)..(14)
<223> OTHER INFORMATION: X may be Ile or Arg.
<220> FEATURE:
<221> NAME/KEY: MISC_FEATURE
<222> LOCATION: (22)..(24)
<223> OTHER INFORMATION: X may Lys or Arg or may be missing.

<400> SEQUENCE: 4

Xaa Xaa Cys Gly Leu Val Arg Ile Ile Leu Gly Ala Val Xaa Gly Ile
1               5                   10                  15

Leu Ile Ile Leu Cys Xaa Xaa Xaa
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X may be Gly or may be missing.
<220> FEATURE:
<221> NAME/KEY: MISC_FEATURE
<222> LOCATION: (2)..(4)
<223> OTHER INFORMATION: X may be Lys or Arg or may be missing.
<220> FEATURE:
<221> NAME/KEY: MISC_FEATURE
<222> LOCATION: (21)..(22)
<223> OTHER INFORMATION: X may be Lys or Arg or may be missing.

<400> SEQUENCE: 5

Xaa Xaa Xaa Xaa Tyr Thr Ile Leu Arg Phe Ile Leu Gly Leu Ala Lys
1               5                   10                  15

Val Ala Leu Ile Xaa Xaa
            20

<210> SEQ ID NO 6
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: X can be Lys or Arg.

<400> SEQUENCE: 6

Tyr Glu Ala Leu Xaa Ile Leu Arg Arg Ile Leu Arg Val Ile Leu Ala
1               5                   10                  15

Gly Gly

<210> SEQ ID NO 7
<211> LENGTH: 20
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(20)
<223> OTHER INFORMATION: X can be Lys or may be missing.

<400> SEQUENCE: 7

Asn Ala Leu Arg Ala Val Ala Gly Ala Ala Leu Ala Ala Val Ala Ala
1               5                   10                  15

Gly Xaa Xaa Xaa
            20

<210> SEQ ID NO 8
<211> LENGTH: 21
<212> TYPE: PRT
<213> ORGANISM: Homo sapiens

<400> SEQUENCE: 8

Gly Asn Leu Val Arg Ile Cys Leu Gly Ala Val Ile Leu Ile Ile Leu
1               5                   10                  15

Ala Gly Phe Leu Ala
            20

<210> SEQ ID NO 9
<211> LENGTH: 11
<212> TYPE: PRT
<213> ORGANISM: Homo sapiens

<400> SEQUENCE: 9

Gly Asn Leu Val Arg Ile Cys Leu Gly Ala Val
1               5                   10

<210> SEQ ID NO 10
<211> LENGTH: 21
<212> TYPE: PRT
<213> ORGANISM: Artificial Sequence
<220> FEATURE:
<223> OTHER INFORMATION: Synthetic

<400> SEQUENCE: 10

Gly Asn Leu Val Arg Ile Cys Leu Arg Ala Val Ile Leu Ile Ile Leu
1               5                   10                  15

Ala Gly Phe Leu Ala
            20

<210> SEQ ID NO 11
<211> LENGTH: 21
<212> TYPE: PRT
<213> ORGANISM: Artificial Sequence
<220> FEATURE:
<223> OTHER INFORMATION: Synthetic

<400> SEQUENCE: 11

Gly Asn Leu Val Arg Ile Gly Leu Arg Ala Val Ile Leu Ile Ile Leu
1               5                   10                  15

Ala Gly Phe Leu Ala
            20

<210> SEQ ID NO 12
<211> LENGTH: 21
<212> TYPE: PRT
<213> ORGANISM: Artificial Sequence
<220> FEATURE:
<223> OTHER INFORMATION: Synthetic
```

```
<400> SEQUENCE: 12

Gly Asn Leu Val Arg Ile Cys Leu Arg Ala Val Arg Leu Ile Ile Leu
1               5                   10                  15

Ala Gly Phe Leu Ala
            20

<210> SEQ ID NO 13
<211> LENGTH: 21
<212> TYPE: PRT
<213> ORGANISM: Artificial Sequence
<220> FEATURE:
<223> OTHER INFORMATION: Synthetic

<400> SEQUENCE: 13

Arg Arg Lys Lys Tyr Ala Arg Ala Leu Leu Tyr Gly Leu Arg Ala Val
1               5                   10                  15

Gly Tyr Arg Lys Lys
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic

<400> SEQUENCE: 14

Gly Arg Arg Lys Lys Tyr Ala Arg Ala Leu Leu Tyr Gly Leu Arg Ala
1               5                   10                  15

Val Gly Tyr Arg Lys Lys
            20

<210> SEQ ID NO 15
<211> LENGTH: 21
<212> TYPE: PRT
<213> ORGANISM: Artificial Sequence
<220> FEATURE:
<223> OTHER INFORMATION: Synthetic

<400> SEQUENCE: 15

Lys Lys Arg Gly Leu Val Lys Ile Leu Leu Arg Ile Leu Arg Val Leu
1               5                   10                  15

Leu Pro Gly Lys Arg
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic

<400> SEQUENCE: 16

Gly Lys Lys Arg Gly Leu Val Lys Ile Leu Leu Arg Ile Leu Arg Val
1               5                   10                  15

Leu Leu Pro Gly Lys Arg
            20

<210> SEQ ID NO 17
<211> LENGTH: 21
<212> TYPE: PRT
<213> ORGANISM: Artificial Sequence
<220> FEATURE:
<223> OTHER INFORMATION: Synthetic
```

```
<400> SEQUENCE: 17

Cys Gly Leu Val Arg Ile Ile Leu Gly Ala Val Ile Gly Ile Leu Ile
1               5                   10                  15

Ile Leu Lys Lys Lys
            20

<210> SEQ ID NO 18
<211> LENGTH: 21
<212> TYPE: PRT
<213> ORGANISM: Artificial Sequence
<220> FEATURE:
<223> OTHER INFORMATION: Synthetic

<400> SEQUENCE: 18

Cys Gly Leu Val Arg Ile Ile Leu Gly Ala Val Ile Gly Ile Leu Ile
1               5                   10                  15

Ile Leu Lys Lys Lys
            20

<210> SEQ ID NO 19
<211> LENGTH: 24
<212> TYPE: PRT
<213> ORGANISM: Artificial Sequence
<220> FEATURE:
<223> OTHER INFORMATION: Synthetic

<400> SEQUENCE: 19

Arg Lys Cys Gly Leu Val Arg Ile Ile Leu Gly Ala Val Arg Gly Ile
1               5                   10                  15

Leu Ile Ile Leu Cys Lys Lys Lys
            20

<210> SEQ ID NO 20
<211> LENGTH: 24
<212> TYPE: PRT
<213> ORGANISM: Artificial Sequence
<220> FEATURE:
<223> OTHER INFORMATION: Synthetic

<400> SEQUENCE: 20

Arg Lys Cys Gly Leu Val Arg Ile Ile Leu Gly Ala Val Arg Gly Ile
1               5                   10                  15

Leu Ile Ile Leu Cys Lys Lys Lys
            20

<210> SEQ ID NO 21
<211> LENGTH: 16
<212> TYPE: PRT
<213> ORGANISM: Artificial Sequence
<220> FEATURE:
<223> OTHER INFORMATION: Synthetic

<400> SEQUENCE: 21

Tyr Thr Ile Leu Arg Phe Ile Leu Gly Leu Ala Lys Val Ala Leu Ile
1               5                   10                  15

<210> SEQ ID NO 22
<211> LENGTH: 21
<212> TYPE: PRT
<213> ORGANISM: Artificial Sequence
<220> FEATURE:
<223> OTHER INFORMATION: Synthetic

<400> SEQUENCE: 22
```

```
Lys Arg Lys Tyr Thr Ile Leu Arg Phe Ile Leu Gly Leu Ala Lys Val
1               5                   10                  15

Ala Leu Ile Lys Arg
            20

<210> SEQ ID NO 23
<211> LENGTH: 22
<212> TYPE: PRT
<213> ORGANISM: Artificial Sequence
<220> FEATURE:
<223> OTHER INFORMATION: Synthetic

<400> SEQUENCE: 23

Gly Lys Arg Lys Tyr Thr Ile Leu Arg Phe Ile Leu Gly Leu Ala Lys
1               5                   10                  15

Val Ala Leu Ile Lys Arg
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic

<400> SEQUENCE: 24

Gly Asn Leu Val Arg Ile Leu Ala Arg Ala Ile Leu Ile Leu Ile Lys
1               5                   10                  15

Ile Leu Ala Gly
            20

<210> SEQ ID NO 25
<211> LENGTH: 24
<212> TYPE: PRT
<213> ORGANISM: Artificial Sequence
<220> FEATURE:
<223> OTHER INFORMATION: Synthetic

<400> SEQUENCE: 25

Lys Lys Gly Asn Leu Val Arg Ile Leu Ala Arg Ala Ile Leu Ile Leu
1               5                   10                  15

Ile Lys Ile Leu Ala Gly Lys Lys
            20

<210> SEQ ID NO 26
<211> LENGTH: 18
<212> TYPE: PRT
<213> ORGANISM: Artificial Sequence
<220> FEATURE:
<223> OTHER INFORMATION: Synthetic

<400> SEQUENCE: 26

Tyr Glu Ala Leu Lys Ile Leu Arg Arg Ile Leu Arg Val Ile Leu Ala
1               5                   10                  15

Gly Gly

<210> SEQ ID NO 27
<211> LENGTH: 17
<212> TYPE: PRT
<213> ORGANISM: Artificial Sequence
<220> FEATURE:
<223> OTHER INFORMATION: Synthetic

<400> SEQUENCE: 27

Asn Ala Leu Arg Ala Val Ala Gly Ala Ala Leu Ala Ala Val Ala Ala
```

```
1               5                   10                  15
Gly

<210> SEQ ID NO 28
<211> LENGTH: 20
<212> TYPE: PRT
<213> ORGANISM: Artificial Sequence
<220> FEATURE:
<223> OTHER INFORMATION: Synthetic

<400> SEQUENCE: 28

Asn Ala Leu Arg Ala Val Ala Gly Ala Ala Leu Ala Ala Val Ala Ala
1               5                   10                  15

Gly Lys Lys Lys
            20

<210> SEQ ID NO 29
<211> LENGTH: 21
<212> TYPE: PRT
<213> ORGANISM: Artificial Sequence
<220> FEATURE:
<223> OTHER INFORMATION: Synthetic

<400> SEQUENCE: 29

Leu Cys Tyr Ile Leu Asp Ala Ile Leu Phe Leu Tyr Gly Ile Val Leu
1               5                   10                  15

Thr Leu Leu Tyr Cys
            20

<210> SEQ ID NO 30
<211> LENGTH: 21
<212> TYPE: PRT
<213> ORGANISM: Artificial Sequence
<220> FEATURE:
<223> OTHER INFORMATION: Synthetic

<400> SEQUENCE: 30

Gly Asn Leu Val Arg Ile Cys Leu Gly Ala Thr Ile Ile Ile Ile Leu
1               5                   10                  15

Leu Gly Leu Leu Ala
            20

<210> SEQ ID NO 31
<211> LENGTH: 21
<212> TYPE: PRT
<213> ORGANISM: Artificial Sequence
<220> FEATURE:
<223> OTHER INFORMATION: Synthetic

<400> SEQUENCE: 31

Leu Cys Tyr Ile Leu Asp Ala Val Leu Phe Leu Tyr Gly Ile Val Leu
1               5                   10                  15

Thr Leu Leu Tyr Cys
            20

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Gly Asn Leu Val Arg Ile Cys Leu Gly Ala
1               5                   10
```

```
<210> SEQ ID NO 33
<211> LENGTH: 18
<212> TYPE: PRT
<213> ORGANISM: Artificial Sequence
<220> FEATURE:
<223> OTHER INFORMATION: Synthetic

<400> SEQUENCE: 33

Val Val Ala Gly Arg Cys Cys Ile Ser Ser Leu Leu Leu Lys Lys Lys
1               5                   10                  15

Pro Pro

<210> SEQ ID NO 34
<211> LENGTH: 11
<212> TYPE: PRT
<213> ORGANISM: Artificial Sequence
<220> FEATURE:
<223> OTHER INFORMATION: Synthetic

<400> SEQUENCE: 34

Gly Asn Leu Val Ala Ile Cys Leu Gly Ala Val
1               5                   10
```